United States Patent
Bermudes et al.

(10) Patent No.: US 10,676,723 B2
(45) Date of Patent: Jun. 9, 2020

(54) CHIMERIC PROTEIN TOXINS FOR EXPRESSION BY THERAPEUTIC BACTERIA

(71) Applicants: David Gordon Bermudes, Woodland Hills, CA (US); David Quintero, Northridge, CA (US)

(72) Inventors: David Gordon Bermudes, Woodland Hills, CA (US); David Quintero, Northridge, CA (US)

(*) Notice: Subject to any disclaimer, the term of this patent is extended or adjusted under 35 U.S.C. 154(b) by 701 days.

(21) Appl. No.: 15/151,194

(22) Filed: May 10, 2016

(65) Prior Publication Data

US 2017/0051260 A1 Feb. 23, 2017

Related U.S. Application Data

(60) Provisional application No. 62/159,645, filed on May 11, 2015.

(51) Int. Cl.
| | |
|---|---|
| *A61K 35/74* | (2015.01) |
| *C07K 14/21* | (2006.01) |
| *A61K 38/45* | (2006.01) |
| *C12N 9/10* | (2006.01) |
| *C12N 15/74* | (2006.01) |
| *C07K 14/005* | (2006.01) |
| *C07K 14/245* | (2006.01) |
| *C07K 14/415* | (2006.01) |
| *A61K 38/00* | (2006.01) |
| *A61K 35/00* | (2006.01) |

(52) U.S. Cl.
CPC ............ *C12N 9/1077* (2013.01); *A61K 35/74* (2013.01); *C07K 14/005* (2013.01); *C07K 14/245* (2013.01); *C07K 14/415* (2013.01); *C12Y 204/02036* (2013.01); *A61K 38/00* (2013.01); *A61K 2035/11* (2013.01); *C07K 2319/00* (2013.01); *C07K 2319/55* (2013.01); *C12N 2750/10022* (2013.01); *C12N 2750/10033* (2013.01)

(58) Field of Classification Search
None
See application file for complete search history.

(56) References Cited

U.S. PATENT DOCUMENTS

| | | | |
|---|---|---|---|
| 3,511,187 A | 5/1970 | Hanna et al. | |
| 3,511,295 A | 5/1970 | Kilmarx et al. | |
| 4,436,727 A | 3/1984 | Ribi | |
| 5,021,234 A | 6/1991 | Ehrenfeld | |
| 5,143,830 A | 9/1992 | Holland et al. | |
| 5,344,762 A | 9/1994 | Karapetian | |
| 5,501,979 A | 3/1996 | Geller et al. | |
| 5,824,538 A | 10/1998 | Branstrom et al. | |
| 5,877,159 A | 3/1999 | Powell et al. | |
| 5,997,881 A | 12/1999 | Powell et al. | |
| 6,080,849 A | 6/2000 | Bermudes et al. | |
| 6,190,657 B1 | 2/2001 | Pawelek et al. | |
| 6,207,648 B1 | 3/2001 | Waxman et al. | |
| 6,251,406 B1 | 6/2001 | Haefliger et al. | |
| 6,447,784 B1 | 9/2002 | Bermudes et al. | |
| 6,475,482 B1 | 11/2002 | Bermudes et al. | |
| 6,548,287 B1 | 4/2003 | Powell et al. | |
| 6,667,038 B1 | 12/2003 | Donta et al. | |
| 6,685,935 B1 | 2/2004 | Pawelek et al. | |
| 6,825,325 B1 | 11/2004 | Fischer et al. | |
| 6,841,535 B2 | 1/2005 | Divita et al. | |
| 6,863,894 B2 | 3/2005 | Bermudes et al. | |
| 6,923,972 B2 | 8/2005 | Bermudes et al. | |
| 6,962,696 B1 | 11/2005 | Bermudes et al. | |
| 7,015,027 B1 | 3/2006 | Redshaw | |
| 7,128,916 B2 | 10/2006 | March | |
| 7,183,105 B2 | 2/2007 | Sabbadini et al. | |
| 7,247,296 B2 | 7/2007 | Redshaw | |
| 7,282,476 B2 | 10/2007 | Denmeade et al. | |
| 7,354,592 B2 | 4/2008 | Bermudes et al. | |
| 7,390,646 B2 | 6/2008 | Andino-Pavlovsky et al. | |
| 7,396,822 B2 | 7/2008 | Sabbadini et al. | |
| RE40,493 E | 9/2008 | Straub et al. | |
| 7,452,531 B2 | 11/2008 | Bermudes et al. | |
| 7,514,089 B2 | 4/2009 | Bermudes et al. | |
| 7,588,767 B2 | 9/2009 | Szalay et al. | |
| 7,588,771 B2 | 9/2009 | Szalay et al. | |
| 7,628,995 B2 | 12/2009 | Bos et al. | |
| 7,635,682 B2 | 12/2009 | Denmeade et al. | |
| 7,662,398 B2 | 2/2010 | Szalay et al. | |
| 7,732,131 B2 | 6/2010 | Moretta et al. | |
| 7,740,835 B2 | 6/2010 | Fujimori et al. | |
| 7,745,395 B2 | 6/2010 | Denmeade et al. | |

(Continued)

OTHER PUBLICATIONS

Baban et al, Bacteria as vectors for gene therapy of cancer, Bioengineered Bugs, 2010, pp. 385-394.*

Goldufsky et al, Pseudomonas aeruginosa exotoxin T induces potent cytotoxicity against a variety of murine and human cancer cell lines, Journal of Medical Microbiology (2015), 64, 164-173.*

Shafikhani and Engel, Pseudomonas aeruginosa type III-secreted toxin ExoT inhibits host-cell division by targeting cytokinesis at multiple steps, PNAS, 2006, pp. 15605-15610.*

(Continued)

Primary Examiner — Maria Marvich

(74) Attorney, Agent, or Firm — Steven M. Hoffberg; Tully Rinckey PLLC

(57) ABSTRACT

Bacteria with tumor-targeting capability express, surface displayed, secreted and/or released modified chimeric therapeutic proteins with enhanced therapeutic activity against a neoplastic tissue including solid tumors, lymphomas and leukemias. The bacteria may be attenuated, non-pathogenic, low pathogenic or a probiotic. The chimeric proteins may be protease sensitive and may optionally be further accompanied by co-expression of a secreted protease inhibitor as a separate molecule or as a fusion.

5 Claims, 15 Drawing Sheets
Specification includes a Sequence Listing.

(56) References Cited

U.S. PATENT DOCUMENTS

| | | |
|---|---|---|
| 7,754,221 B2 | 7/2010 | Szalay et al. |
| 7,763,420 B2 | 7/2010 | Stritzker et al. |
| 7,820,184 B2 | 10/2010 | Stritzker et al. |
| 7,838,266 B2 | 11/2010 | Denmeade et al. |
| 7,872,105 B2 | 1/2011 | Mackenzie et al. |
| 7,893,252 B2 | 2/2011 | Platt et al. |
| 7,910,110 B2 | 3/2011 | March et al. |
| 7,915,381 B2 | 3/2011 | Aderem et al. |
| 7,915,382 B2 | 3/2011 | Qiu |
| 7,935,505 B2 | 5/2011 | Blattner et al. |
| 7,998,461 B2 | 8/2011 | Forbes et al. |
| 8,003,613 B2 | 8/2011 | Cance et al. |
| 8,021,653 B2 | 9/2011 | Kano et al. |
| 8,021,662 B2 | 9/2011 | Szalay et al. |
| 8,029,807 B2 | 10/2011 | Bos et al. |
| 8,052,968 B2 | 11/2011 | Chen et al. |
| 8,066,984 B2 | 11/2011 | Szalay et al. |
| 8,101,396 B2 | 1/2012 | Sabbadini et al. |
| 8,105,602 B2 | 1/2012 | Parry et al. |
| 8,129,166 B2 | 3/2012 | Sabbadini et al. |
| 8,137,904 B2 | 3/2012 | Szalay et al. |
| 8,163,295 B2 | 4/2012 | Bos et al. |
| 8,221,739 B2 | 7/2012 | Leonard et al. |
| 8,221,769 B2 | 7/2012 | Szalay et al. |
| 8,241,623 B1 | 8/2012 | Bermudes |
| 8,309,077 B2 | 11/2012 | Murthy et al. |
| 8,323,959 B2 | 12/2012 | Szalay et al. |
| 8,337,861 B2 | 12/2012 | Paterson et al. |
| 8,343,509 B2 | 1/2013 | Stritzker et al. |
| 8,357,486 B2 | 1/2013 | Stritzker et al. |
| 8,440,207 B2 | 5/2013 | Bermudes |
| 8,465,931 B2 | 6/2013 | Moretta et al. |
| 8,524,220 B1 | 9/2013 | Bermudes |
| 8,524,484 B2 | 9/2013 | Sabbadini et al. |
| 8,568,707 B2 | 10/2013 | Szalay et al. |
| 8,586,022 B2 | 11/2013 | Szalay et al. |
| 8,613,928 B2 | 12/2013 | Solomon |
| 8,623,350 B1 | 1/2014 | Bermudes |
| 8,642,257 B2 | 2/2014 | Szalay et al. |
| 8,647,618 B2 | 2/2014 | Leonard et al. |
| 8,647,642 B2 | 2/2014 | Bermudes |
| 8,652,806 B2 | 2/2014 | Qiu |
| 8,663,916 B2 | 3/2014 | Qiu |
| 8,680,243 B2 | 3/2014 | Funahashi |
| 8,685,939 B2 | 4/2014 | Wei et al. |
| 8,697,640 B2 | 4/2014 | Qiu |
| 8,703,146 B2 | 4/2014 | Aderem et al. |
| 8,716,254 B2 | 5/2014 | Xiang et al. |
| 8,734,779 B2 | 5/2014 | Hamaji et al. |
| 8,771,669 B1 | 7/2014 | Bermudes |
| 8,784,836 B2 | 7/2014 | Szalay et al. |
| 8,815,503 B2 | 8/2014 | Hartmann et al. |
| 8,835,603 B2 | 9/2014 | Anderson et al. |
| 8,846,870 B2 | 9/2014 | Kawai et al. |
| 8,852,927 B2 | 10/2014 | Szalay et al. |
| 8,859,256 B2 | 10/2014 | Szalay et al. |
| 8,865,153 B2 | 10/2014 | Szalay et al. |
| 8,916,161 B2 | 12/2014 | Buckley |
| 8,956,859 B1 | 2/2015 | Bermudes |
| 9,005,602 B2 | 4/2015 | Szalay et al. |
| 9,017,986 B2 | 4/2015 | Sabbadini et al. |
| 9,068,187 B1 | 6/2015 | Bermudes |
| 9,085,616 B2 | 7/2015 | Aderem et al. |
| 9,102,759 B2 | 8/2015 | Pieczykolan et al. |
| 9,127,284 B2 | 9/2015 | Huang et al. |
| 9,139,647 B2 | 9/2015 | Aburatani et al. |
| 9,163,068 B2 | 10/2015 | Khurana et al. |
| 9,193,770 B2 | 11/2015 | Gaily et al. |
| 9,200,251 B1 | 12/2015 | Bermudes |
| 9,200,289 B1 | 12/2015 | Bermudes |
| 9,200,296 B2 | 12/2015 | Renninger et al. |
| 9,265,804 B2 | 2/2016 | Newman |
| 9,296,823 B2 | 3/2016 | Funahashi |
| 9,314,514 B2 | 4/2016 | Eisele |
| 9,315,817 B2 | 4/2016 | Bermudes |
| 9,322,011 B2 | 4/2016 | Luirink et al. |
| 9,358,308 B2 | 6/2016 | Primiano et al. |
| 9,365,625 B1 | 6/2016 | Bermudes |
| 2001/0006642 A1 | 7/2001 | Steidler et al. |
| 2002/0026655 A1 | 2/2002 | Bermudes et al. |
| 2003/0049689 A1 | 3/2003 | Edwards et al. |
| 2003/0059400 A1 | 3/2003 | Szalay |
| 2003/0109026 A1 | 6/2003 | Bermudes et al. |
| 2003/0113293 A1 | 6/2003 | Bermudes et al. |
| 2003/0170276 A1 | 9/2003 | Bermudes et al. |
| 2004/0219169 A1 | 11/2004 | Bermudes et al. |
| 2005/0036987 A1 | 2/2005 | Pawelek et al. |
| 2005/0118165 A1 | 6/2005 | Hay et al. |
| 2005/0249706 A1 | 11/2005 | Bermudes et al. |
| 2005/0255088 A1 | 11/2005 | Bermudes et al. |
| 2006/0003407 A1 | 1/2006 | Rennert et al. |
| 2007/0009489 A1 | 1/2007 | Bermudes et al. |
| 2007/0031449 A1 | 2/2007 | Bos et al. |
| 2008/0081346 A1 | 4/2008 | Morella et al. |
| 2008/0124355 A1 | 5/2008 | Bermudes |
| 2009/0169517 A1 | 7/2009 | Bermudes et al. |
| 2010/0047287 A1 | 2/2010 | Bos et al. |
| 2010/0111852 A1 | 5/2010 | Yoshida |
| 2010/0135961 A1 | 6/2010 | Bermudes |
| 2010/0136048 A1 | 6/2010 | Bermudes |
| 2010/0285531 A1 | 11/2010 | Morella et al. |
| 2011/0176995 A1 | 7/2011 | Funahashi |
| 2011/0223241 A1 | 9/2011 | Tardi et al. |
| 2011/0262929 A1 | 10/2011 | Kawai et al. |
| 2011/0293644 A1 | 12/2011 | Anderson et al. |
| 2012/0004117 A1 | 1/2012 | Aburatani et al. |
| 2012/0014870 A1 | 1/2012 | Aburatani et al. |
| 2012/0039942 A1 | 2/2012 | Bos et al. |
| 2012/0141501 A1 | 6/2012 | Yoshida et al. |
| 2012/0142080 A1 | 6/2012 | Bermudes |
| 2012/0189572 A1 | 7/2012 | Wei et al. |
| 2013/0315892 A1 | 11/2013 | Moretta et al. |
| 2014/0147383 A1 | 5/2014 | Funahashi |
| 2014/0205538 A1 | 7/2014 | Wei et al. |
| 2014/0220661 A1 | 8/2014 | Bermudes |
| 2014/0377781 A1 | 12/2014 | Yoshida |
| 2015/0017204 A1 | 1/2015 | Bermudes |
| 2015/0050303 A1 | 2/2015 | Anderson et al. |
| 2015/0118184 A1 | 4/2015 | Kawai |
| 2016/0017028 A1 | 1/2016 | Yoshida et al. |

OTHER PUBLICATIONS

Kreitman et al, Properties of Chimeric Toxins with Two Recognition Domains: Interleukin 6 and Transforming Growth Factor a at Different Locations in Pseudomonas Exotoxin, Bioconjugate Chem. 1992, 3, 63-68.*

Kreitman et al, Recombinant Immunotoxins Containing Truncated Bacterial Toxins for the Treatment of Hematologic MalignanciesBioDrugs. 2009 ; 23(1): 1-13.*

* cited by examiner

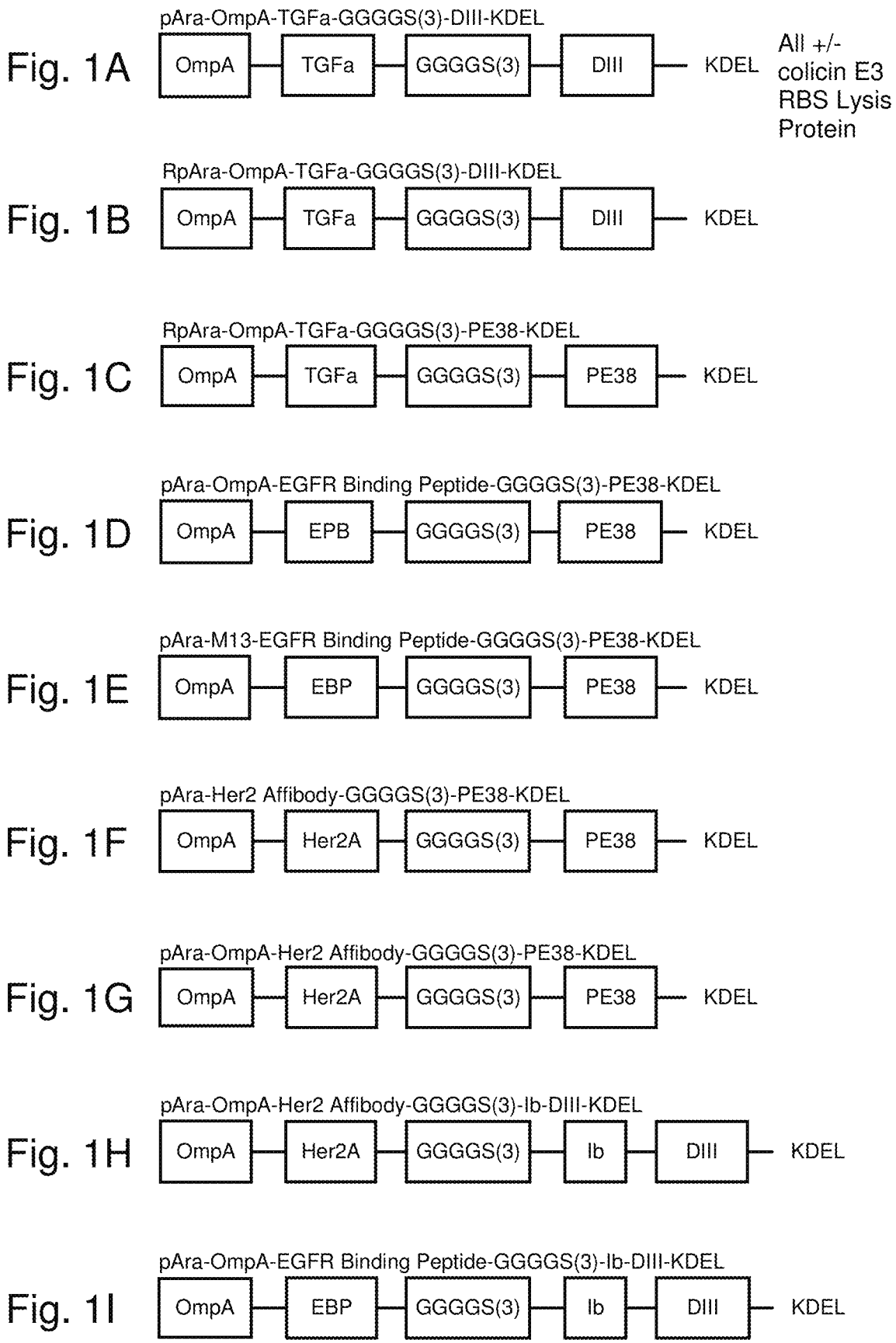

1 - 121
33 - 121
82 - 121
97 - 121
106 - 121
111 - 121
1-31;83-121
TAT - 121

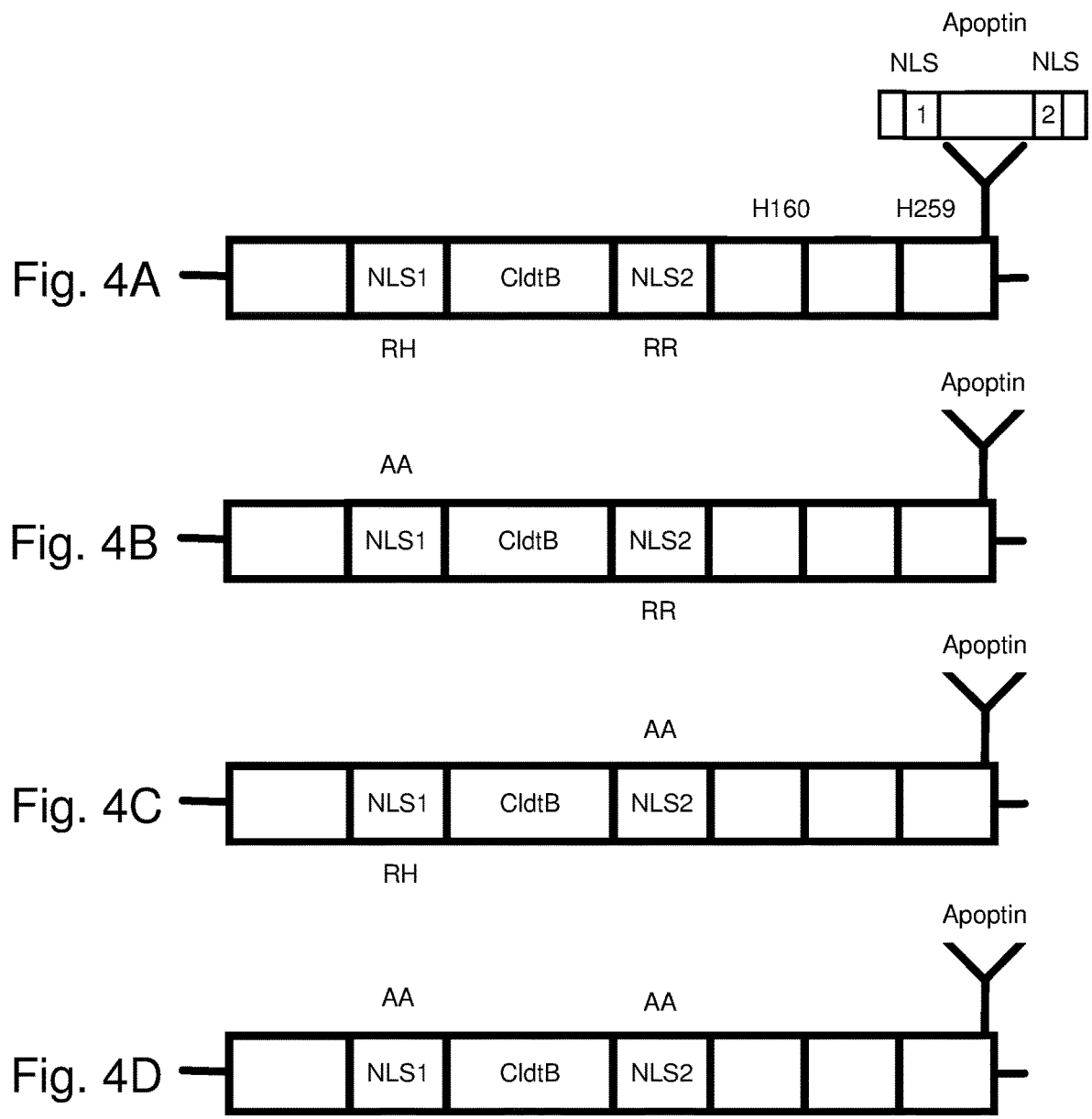

Fig. 5A
Fig. 5B
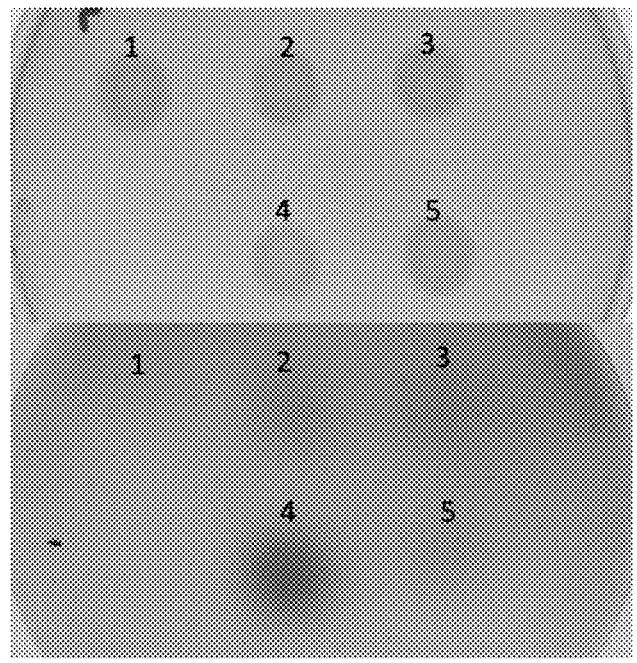
Fig. 5C
Fig. 5D
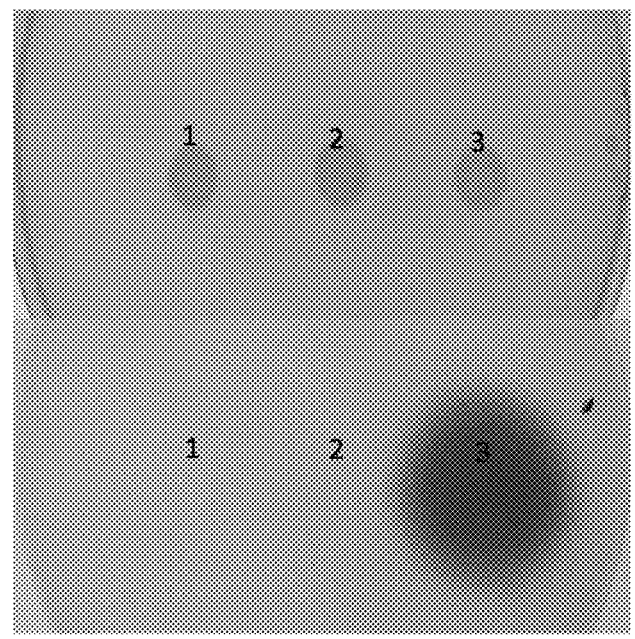

SEQUENCE LISTING

<160> NUMBER OF SEQ ID NOS: 23

<210> SEQ ID NO 1
<211> LENGTH: 3789
<212> TYPE: DNA
<213> ORGANISM: Artificial Sequence
<220> FEATURE:
<223> OTHER INFORMATION: Modified TGF-alpha-GIII-KDEL

<400> SEQUENCE: 1

```
gggggcggcc gcaagaaacc aattgtccat attgcatcag acattgccgt cactgcgtct      60
tttactggct cttctcgcta accaaaccgg taacccctgc tattaaaagc attctgtaac     120
aaagcgggac caaagccatg acaaaaacgc gtaacaaaag tgtctataat cacggcagaa     180
aagtccacat tgattatttg cacggcgtca cactttgcta tgccatagca ttttttatcca     240
taagattagc ggatcctacc tgacgctttt tatcgcaact ctctactgtt tctccatacc     300
cgttttttg ggctagcgaa ttcgagctcg gtacccagga ggaattcacc atggctaaaa     360
agacagctat cgcgattgca gtggcactgg ctggtttcgc taccgtagcg caggcagctg     420
tggtgagcca ttttaacgat tgcccggata gccataccca gttttgcttt catggcacct     480
gccgctttct ggtgcaggaa gataaaccgg cgtgcgtgtg ccatagcggt tatgtgggcg     540
ctcgctgcga acatgcggat ctgctggccc atcaactagt gggcggtggt ggcagtggtg     600
gcggcggctc tggtggtggc gggtcccggg gtctgacctg cccggtcgcc gccggtgaat     660
gcgcgggccc ggcggacagc ggcgacgccc tgctggagcg caactatccc actggcgcgg     720
agttcctcgg cgacggcggc gacgtcagct tcagcacccg cggcacgcag aactggacgg     780
tggagcggct gctccaggcg caccgccaac tggaggagcg cggctatgtg ttcgtcggct     840
accacggcac cttcctcgaa gcggcgcaaa gcatcgtctt cggcggggtg cgcgcgcgca     900
gccaggacct cgacgcgatc tggcgcgtt tctatatcgc cggcgatccg gcgctggcct     960
acggctacgc ccaggaccag gaacccgacg cacgcggccg gatccgcaac ggtgccctgc    1020
tgcgggtcta tgtgccgcgc tcgagcctgc cgggcttcta ccgcaccagc ctgacccctgg    1080
ccgcgccgga ggcggcgggc gaggtcgaac ggctgatcgg ccatccgctg ccgctgcgcc    1140
tggacgccat caccggcccc gaggaggaag gcgggcgcct ggagaccatt tcggctggc    1200
cgctggccga gcgcaccgtg gtgattccct cggcgatccc caccgacccg cgcaacgtcg    1260
gcggcgacct cgaccgtcc agcatccccg acaaggaaca ggcgatcagc gccctgccgg    1320
actacgccag ccagcccggc aaaccgccga agatgaact gtaactcgag tagatctgta    1380
ctctagagtc gacctgcagg catgcaagct tggctgtttt ggcggatgag agaagatttt    1440
cagcctgata cagattaaat cagaacgcag aagcggtctg ataaaacaga atttgcctgg    1500
cggcagtagc gcggtggtcc cacctgaccc catgccgaac tcagaagtga acgccgtag    1560
cgccgatggt agtgtgggt ctccccatgc gagagtaggg aactgccagg catcaaataa    1620
aacgaaaggc tcagtcgaaa gactgggcct ttcgttttat ctgttgtttg tcggtgaacg    1680
ctctcctgag taggacaaat ccgccgggag cggatttgaa cgttgcgaag caacggcccg    1740
gagggtggcg gcaggacgc ccgccataaa ctgccaggca tcaaattaag cagaaggcca    1800
tcctgacgga tggcctttt gcgtttctac aaactctttt gtttatttt ctaaatacca    1860
ttcaaatatg tatccgctca tgagacaata accctgataa atgcttcaat aatattgaaa    1920
aaggaagagt atgagtattc aacatttccg tgtcgccctt attcccttt ttgcggcatt    1980
ttgccttcct gttttgctc acccagaaac gctggtgaaa gtaaaagatg ctgaagatca    2040
```

-continued

```
gttgggtgca cgagtgggtt acatcgaact ggatctcaac agcggtaaga tccttgagag    2100
ttttcgcccc gaagaacgtt ttccaatgat gagcactttt aaagttctgc tatgtggcgc    2160
ggtattatcc cgtgttgacg ccgggcaaga gcaactcggt cgccgcatac actattctca    2220
gaatgacttg gttgagtact caccagtcac agaaaagcat cttacggatg gcatgacagt    2280
aagagaatta tgcagtgctg ccataaccat gagtgataac actgcggcca acttacttct    2340
gacaacgatc ggaggaccga aggagctaac cgcttttttg cacaacatgg gggatcatgt    2400
aactcgcctt gatcgttggg aaccggagct gaatgaagcc ataccaaacg acgagcgtga    2460
caccacgatg cctacagcaa tggcaacaac gttgcgcaaa ctattaactg gcgaactact    2520
tactctagct tcccggcaac aattaataga ctggatggag gcggataaag ttgcaggacc    2580
acttctgcgc tcggcccttc cggctggctg gtttattgct gataaatctg gagccggtga    2640
gcgtgggtct cgcggtatca ttgcagcact ggggccagat ggtaagccct cccgtatcgt    2700
agttatctac acgacgggga gtcaggcaac tatggatgaa cgaaatagac agatcgctga    2760
gataggtgcc tcactgatta agcattggta actgtcagac caagtttact catatatact    2820
ttagattgat ttaaaacttc attttttaatt taaaaggatc taggtgaaga tcctttttga    2880
taatctcatg accaaaatcc cttaacgtga gttttcgttc cactgagcgt cagacccgt     2940 agaaaagatc aaaggatctt cttgagatcc tttttttctg cgcgtaatct gctgcttgca    3000
aacaaaaaaa ccaccgctac cagcggtggt ttgtttgccg gatcaagagc taccaactct    3060 tttttccgaag gtaactggct tcagcagagc gcagatacca atactgtcc ttctagtgta    3120 gccgtagtta ggccaccact tcaagaactc tgtagcaccg cctacatacc tcgctctgct    3180
aatcctgtta ccagtggctg ctgccagtgg cgataagtcg tgtcttaccg ggttggactc    3240
aagacgatag ttaccggata aggcgcagcg gtcgggctga acggggggtt cgtgcacaca    3300
gcccagcttg gagcgaacga cctacaccga actgagatac ctacagcgtg agctatgaga    3360
aagcgccacg cttcccgaag ggagaaaggc ggacaggtat ccggtaagcg cagggtcgg     3420 aacaggagag cgcacgaggg agcttccagg gggaaacgcc tggtatcttt atagtcctgt    3480
cgggtttcgc cacctctgac ttgagcgtcg attttgtga tgctcgtcag gggggcggag     3540
cctatggaaa aacgccagca acgcggcctt tttacggttc ctggccttt gctggccttt    3600 tgctcacatg ttctttcctg cgttatcccc tgattctgtg gataaccgta ttaccgcctt    3660
tgagtgagct gataccgctc gccgcagccg aacgaccgag cgcagcgagt cagtgagcga    3720
ggaagcggaa gagcgcctga tgcggtattt tctccttacg catctgtgcg gtatttcaca    3780
ccgcatatg                                                            3789
```

<210> SEQ ID NO 2
<211> LENGTH: 3938
<212> TYPE: DNA
<213> ORGANISM: Artificial Sequence
<220> FEATURE:
<223> OTHER INFORMATION: Modified TGF-alpha-GIII-KDEL

<400> SEQUENCE: 2

```
gggggcggcc gcaagaaacc aattgtccat attgcatcag acattgccgt cactgcgtct     60
tttactggct cttctcgcta accaaaccgg taaccccgct tattaaaagc attctgtaac    120
aaagcgggac caaagccatg acaaaaacgc gtaacaaaag tgtctataat cacggcagaa    180
aagtccacat tgattatttg cacggcgtca cactttgcta tgccatagca tttttatcca    240
```

-continued

| | |
|---|---|
| taagattagc ggatcctacc tgacgctttt tatcgcaact ctctactgtt tctccatacc | 300 |
| cgttttttg ggctagcgaa ttcgagctcg gtacccagga ggaattcacc atggctaaaa | 360 |
| agacagctat cgcgattgca gtggcactgg ctggtttcgc taccgtagcg caggcagctg | 420 |
| tggtgagcca ttttaacgat tgcccggata gccataccca gttttgcttt catggcacct | 480 |
| gccgctttct ggtgcaggaa gataaaccgg cgtgcgtgtg ccatagcggt tatgtgggcg | 540 |
| ctcgctgcga acatgcggat ctgctggccc atcaactagt gggcggtggt ggcagtggtg | 600 |
| gcggcggctc tggtggtggc gggtcccggg gtctgacctg cccggtcgcc gccggtgaat | 660 |
| gcgcgggccc ggcggacagc ggcgacgccc tgctggagcg caactatccc actggcgcgg | 720 |
| agttcctcgg cgacggcggc gacgtcagct tcagcacccg cggcacgcag aactggacgg | 780 |
| tggagcggct gctccaggcg caccgccaac tggaggagcg cggctatgtg ttcgtcggct | 840 |
| accacggcac cttcctcgaa gcggcgcaaa gcatcgtctt cggcggggtg cgcgcgcgca | 900 |
| gccaggacct cgacgcgatc tggcgcggtt tctatatcgc cggcgatccg gcgctggcct | 960 |
| acggctacgc ccaggaccag gaacccgacg cacgcggccg gatccgcaac ggtgccctgc | 1020 |
| tgcgggtcta tgtgccgcgc tcgagcctgc cgggcttcta ccgcaccagc ctgaccctgg | 1080 |
| ccgcgccgga ggcggcgggc gaggtcgaac ggctgatcgg ccatccgctg ccgctgcgcc | 1140 |
| tggacgccat caccggcccc gaggaggaag gcgggcgcct ggagaccatt ctcggctggc | 1200 |
| cgctggccga gcgcaccgtg gtgattccct cggcgatccc caccgacccg cgcaacgtcg | 1260 |
| gcggcgacct cgacccgtcc agcatccccg acaaggaaca ggcgatcagc gccctgccgg | 1320 |
| actacgccag ccagcccggc aaaccgccga agatgaact gtaactcgag tagatctgta | 1380 |
| ctctagaaag gagtcgttat gaaaaaaata cagggatta ttttattgct tcttgcagtc | 1440 |
| attattctgt ctgcatgtca ggcaaactat atccggatg ttcagggcgg daccgtatct | 1500 |
| ccgtcatcaa cagctgaagt gaccggatta gcaacgcagt aactgcaggc atgcaagctt | 1560 |
| ggctgttttg gcggatgaga aagattttc agcctgatac agattaaatc agaacgcaga | 1620 |
| agcggtctga taaaacagaa tttgcctggc ggcagtagcg cggtggtccc acctgacccc | 1680 |
| atgccgaact cagaagtgaa acgccgtagc gccgatggta gtgtgggtc tccccatgcg | 1740 |
| agagtaggga actgccaggc atcaaataaa acgaaaggct cagtcgaaag actgggcctt | 1800 |
| tcgttttatc tgttgtttgt cggtgaacgc tctcctgagt aggacaaatc cgccgggagc | 1860 |
| ggatttgaac gttgcgaagc aacggcccgg agggtggcgg gcaggacgcc cgccataaac | 1920 |
| tgccaggcat caaattaagc agaaggccat cctgacggat ggccttttg cgtttctaca | 1980 |
| aactctttt gtttatttt ctaaatacat tcaaatatgt atccgctcat gagacaataa | 2040 |
| ccctgataaa tgcttcaata atattgaaaa aggaagagta tgagtattca acatttccgt | 2100 |
| gtcgcctta ttccctttt tgcggcattt tgccttcctg tttttgctca cccagaaacg | 2160 |
| ctggtgaaag taaagatgc tgaagatcag ttgggtgcac gagtgggtta catcgaactg | 2220 |
| gatctcaaca gcggtaagat ccttgagagt tttcgccccg aagaacgttt tccaatgatg | 2280 |
| agcacttta aagttctgct atgtggcgcg gtattatccc gtgttgacgc cgggcaagag | 2340 |
| caactcggtc gccgcataca ctattctcag aatgacttgg ttgagtactc accagtcaca | 2400 |
| gaaaagcatc ttacggatgg catgacagta agagaattat gcagtgctgc cataaccatg | 2460 |
| agtgataaca ctgcggccaa cttacttctg acaacgatcg gaggaccgaa ggagctaacc | 2520 |
| gcttttttgc acaacatggg ggatcatgta actcgccttg atcgttggga accggagctg | 2580 |
| aatgaagcca taccaaacga cgagcgtgac accacgatgc ctacagcaat ggcaacaacg | 2640 |

| | |
|---|---|
| ttgcgcaaac tattaactgg cgaactactt actctagctt cccggcaaca attaatagac | 2700 |
| tggatggagg cggataaagt tgcaggacca cttctgcgct cggcccttcc ggctggctgg | 2760 |
| tttattgctg ataaatctgg agccggtgag cgtgggtctc gcggtatcat tgcagcactg | 2820 |
| gggccagatg gtaagccctc ccgtatcgta gttatctaca cgacggggag tcaggcaact | 2880 |
| atggatgaac gaaatagaca gatcgctgag ataggtgcct cactgattaa gcattggtaa | 2940 |
| ctgtcagacc aagtttactc atatatactt tagattgatt taaaacttca ttttttaattt | 3000 |
| aaaaggatct aggtgaagat cctttttgat aatctcatga ccaaaatccc ttaacgtgag | 3060 |
| ttttcgttcc actgagcgtc agaccccgta gaaaagatca aggatcttc ttgagatcct | 3120 |
| ttttttctgc gcgtaatctg ctgcttgcaa acaaaaaaac caccgctacc agcggtggtt | 3180 |
| tgtttgccgg atcaagagct accaactctt tttccgaagg taactggctt cagcagagcg | 3240 |
| cagataccaa atactgtcct tctagtgtag ccgtagttag gccaccactt caagaactct | 3300 |
| gtagcaccgc ctacatacct cgctctgcta atcctgttac cagtggctgc tgccagtggc | 3360 |
| gataagtcgt gtcttaccgg gttggactca agacgatagt taccggataa ggcgcagcgg | 3420 |
| tcgggctgaa cggggggttc gtgcacacag cccagcttgg agcgaacgac ctacaccgaa | 3480 |
| ctgagatacc tacagcgtga gctatgagaa agcgccacgc ttcccgaagg gagaaaggcg | 3540 |
| gacaggtatc cggtaagcgg cagggtcgga acaggagagc gcacgaggga gcttccaggg | 3600 |
| ggaaacgcct ggtatcttta tagtcctgtc gggtttcgcc acctctgact tgagcgtcga | 3660 |
| ttttgtgat gctcgtcagg gggcggagc ctatggaaaa acgccagcaa cgcggccttt | 3720 |
| ttacggttcc tggccttttg ctggcctttt gctcacatgt tctttcctgc gttatcccct | 3780 |
| gattctgtgg ataaccgtat taccgccttt gagtgagctg ataccgctcg ccgcagccga | 3840 |
| acgaccgagc gcagcgagtc agtgagcgag gaagcggaag agcgcctgat gcggtatttt | 3900 |
| ctccttacgc atctgtgcgg tatttcacac cgcatatg | 3938 |

<210> SEQ ID NO 3
<211> LENGTH: 3938
<212> TYPE: DNA
<213> ORGANISM: Artificial Sequence
<220> FEATURE:
<223> OTHER INFORMATION: arabinose inducible plasmid, with start codon
      at 351, stop codon at 1364, and the colicin E3 lysis protein from
      1399 to 1542

<400> SEQUENCE: 3

| | |
|---|---|
| gggggcggcc gcaagaaacc aattgtccat attgcatcag acattgccgt cactgcgtct | 60 |
| tttactggct cttctcgcta accaaaccgg taaccccgct tattaaaagc attctgtaac | 120 |
| aaagcgggac caaagccatg acaaaaacgc gtaacaaaag tgtctataat cacggcagaa | 180 |
| aagtccacat tgattatttg cacggcgtca cactttgcta tgccatagca ttttttatcca | 240 |
| taagattagc ggatcctacc tgacgctttt tatcgcaact ctctactgtt tctccatacc | 300 |
| cgttttttg ggctagcgaa ttcgagctcg gtacccagga ggaattcacc atggctaaaa | 360 |
| agacagctat cgcgattgca gtggcactgg ctggtttcgc taccgtagcg caggcagctg | 420 |
| tggtgagcca ttttaacgat tgcccggata gccatacca gttttgcttt catggcacct | 480 |
| gccgctttct ggtgcaggaa gataaaccgg cgtgcgtgtg ccatagcggt tatgtgggcg | 540 |
| ctcgctgcga acatgcggat ctgctggccc atcaactagt gggcggtggt ggcagtggtg | 600 |
| gcggcggctc tggtggtggc gggtcccggg gtctgacctg cccggtcgcc gccggtgaat | 660 |

```
gcgcgggccc ggcggacagc ggcgacgccc tgctggagcg caactatccc actggcgcgg    720
agttcctcgg cgacggcggc gacgtcagct tcagcacccg cggcacgcag aactggacgg    780
tggagcggct gctccaggcg caccgccaac tggaggagcg cggctatgtg ttcgtcggct    840
accacggcac cttcctcgaa gcggcgcaaa gcatcgtctt cggcggggtg cgcgcgcgca    900
gccaggacct cgacgcgatc tggcgcggtt tctatatcgc cggcgatccg gcgctggcct    960
acggctacgc ccaggaccag gaacccgacg cacgcggccg gatccgcaac ggtgccctgc    1020
tgcgggtcta tgtgccgcgc tcgagcctgc cgggcttcta ccgcaccagc ctgaccctgg    1080
ccgcgccgga ggcggcgggc gaggtcgaac ggctgatcgg ccatccgctg ccgctgcgcc    1140
tggacgccat caccggcccc gaggaggaag gcgggcgcct ggagaccatt ctcggctggc    1200
cgctggccga gcgcaccgtg gtgattccct cggcgatccc caccgacccg cgcaacgtcg    1260
gcggcgacct cgacccgtcc agcatccccg acaaggaaca ggcgatcagc gccctgccgg    1320
actacgccag ccagcccggc aaaccgccga agatgaact gtaactcgag tagatctgta    1380
ctctagaaag gagtcgttat gaaaaaaata cagggatta ttttattgct tcttgcagtc    1440
attattctgt ctgcatgtca ggcaaactat atccgggatg ttcagggcgg gaccgtatct    1500
ccgtcatcaa cagctgaagt gaccggatta gcaacgcagt aactgcaggc atgcaagctt    1560
ggctgttttg gcggatgaga gaagattttc agcctgatac agattaaatc agaacgcaga    1620
agcggtctga taaaacagaa tttgcctggc ggcagtagcg cggtggtccc acctgacccc    1680
atgccgaact cagaagtgaa acgccgtagc gccgatggta gtgtggggtc tccccatgcg    1740
agagtaggga actgccaggc atcaaataaa acgaaaggct cagtcgaaag actgggcctt    1800
tcgttttatc tgttgtttgt cggtgaacgc tctcctgagt aggacaaatc cgccgggagc    1860
ggatttgaac gttgcgaagc aacgcccgg agggtggcgg gcaggacgcc cgccataaac    1920
tgccaggcat caaattaagc agaaggccat cctgacggat ggcctttttg cgtttctaca    1980
aactcttttt gttatttttt ctaaatacat tcaaatatgt atccgctcat gagacaataa    2040
ccctgataaa tgcttcaata atattgaaaa aggaagagta tgagtattca acatttccgt    2100
gtcgccctta ttcccttttt tgcggcattt tgccttcctg ttttgctca cccagaaacg    2160 ctggtgaaag taaaagatgc tgaagatcag ttgggtgcac gagtgggtta catcgaactg    2220
gatctcaaca gcggtaagat ccttgagagt tttcgccccg aagaacgttt tccaatgatg    2280 agcacttta aagttctgct atgtggcgcg gtattatccc gtgttgacgc cgggcaagag    2340
caactcggtc gccgcataca ctattctcag aatgacttgg ttgagtactc accagtcaca    2400
gaaaagcatc ttacggatgg catgacagta agagaattat gcagtgctgc cataaccatg    2460
agtgataaca ctgcggccaa cttacttctg acaacgatcg gaggaccgaa ggagctaacc    2520
gcttttttgc acaacatggg ggatcatgta actcgccttg atcgttggga accggagctg    2580
aatgaagcca taccaaacga cgagcgtgac accacgatgc ctacagcaat ggcaacaacg    2640
ttgcgcaaac tattaactgg cgaactactt actctagctt cccggcaaca attaatagac    2700
tggatggagg cggataaagt tgcaggacca cttctgcgct cggcccttcc ggctggctgg    2760
tttattgctg ataaatctgg agccggtgag cgtgggtctc gcggtatcat tgcagcactg    2820
gggccagatg gtaagccctc ccgtatcgta gttatctaca cgacggggag tcaggcaact    2880
atggatgaac gaaatagaca gatcgctgag ataggtgcct cactgattaa gcattggtaa    2940
ctgtcagacc aagtttactc atatatactt tagattgatt taaaacttca tttttaattt    3000
aaaaggatct aggtgaagat cctttttgat aatctcatga ccaaaatccc ttaacgtgag    3060
```

-continued

```
ttttcgttcc actgagcgtc agacccgta gaaaagatca aaggatcttc ttgagatcct    3120 tttttctgc gcgtaatctg ctgcttgcaa acaaaaaaac caccgctacc agcggtggtt    3180
tgtttgccgg atcaagagct accaactctt tttccgaagg taactggctt cagcagagcg    3240
cagataccaa atactgtcct tctagtgtag ccgtagttag gccaccactt caagaactct    3300
gtagcaccgc ctacatacct cgctctgcta atcctgttac cagtggctgc tgccagtggc    3360
gataagtcgt gtcttaccgg gttggactca agacgatagt taccggataa ggcgcagcgg    3420
tcgggctgaa cggggggttc gtgcacacag cccagcttgg agcgaacgac ctacaccgaa    3480
ctgagatacc tacagcgtga gctatgagaa agcgccacgc ttcccgaagg agaaaggcg    3540 gacaggtatc cggtaagcgg cagggtcgga acaggagagc gcacgaggga gcttccaggg    3600
ggaaacgcct ggtatcttta tagtcctgtc gggtttcgcc acctctgact tgagcgtcga    3660
tttttgtgat gctcgtcagg ggggcggagc ctatggaaaa acgccagcaa cgcggccttt    3720
ttacggttcc tggccttttg ctggccttttt gctcacatgt tctttcctgc gttatcccct    3780
gattctgtgg ataaccgtat taccgccttt gagtgagctg ataccgctcg ccgcagccga    3840
acgaccgagc gcagcgagtc agtgagcgag gaagcggaag agcgcctgat gcggtatttt    3900
ctccttacgc atctgtgcgg tatttcacac cgcatatg                           3938
```

<210> SEQ ID NO 4
<211> LENGTH: 3711
<212> TYPE: DNA
<213> ORGANISM: Artificial Sequence
<220> FEATURE:
<223> OTHER INFORMATION: Modified TGF-alpha-GIII-KDEL

<400> SEQUENCE: 4

```
gggggcggcc gcaagaaacc aattgtccat attgcatcag acattgccgt cactgcgtct    60
tttactggct cttctcgcta accaaaccgg taaccccgct tattaaaagc attctgtaac    120
aaagcgggac caaagccatg acaaaaacgc gtaacaaaag tgtctataat cacggcagaa    180
aagtccacat tgattatttg cacggcgtca cactttgcta tgccatagca ttttttatcca    240 taagattagc ggatcctacc tgacgctttt tatcgcaact ctctactgtt tctccatacc    300 cgttttttg gctagcgaa ttcgagctcg gtacccagga ggaattcacc atggctaaaa    360
agacagctat cgcgattgca gtggcactgg ctggtttcgc taccgtagcg caggcagctg    420
tggtgagcca ttttaacgat tgcccggata gccataccca gttttgcttt catggcacct    480
gccgctttct ggtgcaggaa gataaaccgg cgtgcgtgtg ccatagcggt tatgtgggcg    540
ctcgctgcga acatgcggat ctgctggccc atcaactagt gggcggtggt ggcagtggtg    600
gcggcggctc tggtggtggc gggtcccggg gtactgcgcg ggagttcctc ggcgacggcg    660
gcgacgtcag cttcagcacc cgcggcacgc agaactggac ggtggagcgg ctgctccagg    720
cgcaccgcca actggaggag cgcggctatg tgttcgtcgg ctaccacggc accttcctcg    780
aagcggcgca aagcatcgtc ttcggcgggg tgcgcgcgcg cagccaggac ctcgacgcga    840
tctggcgcgg tttctatatc gccggcgatc cggcgctggc ctacggctac gcccaggacc    900
aggaacccga cgcacgcggc cggatccgca acggtgccct gctgcgggtc tatgtgccgc    960
gctcgagcct gccgggcttc taccgcacca gcctgaccct ggccgcgccg gaggcggcgg    1020
gcgaggtcga acggctgatc ggccatccgc tgccgctgcg cctggacgcc atcaccggcc    1080
ccgaggagga aggcgggcgc ctggagacca ttctcggctg gccgctggcc gagcgcaccg    1140
```

```
tggtgattcc ctcggcgatc cccaccgacc cgcgcaacgt cggcggcgac ctcgacccgt    1200
ccagcatccc cgacaaggaa caggcgatca gcgccctgcc ggactacgcc agccagcccg    1260
gcaaaccgcc gaaagatgaa ctgtaactcg agtagatctg tactctagag tcgacctgca    1320
ggcatgcaag cttggctgtt ttggcggatg agagaagatt ttcagcctga tacagattaa    1380
atcagaacgc agaagcggtc tgataaaaca gaatttgcct ggcggcagta gcgcggtggt    1440
cccacctgac cccatgccga actcagaagt gaaacgccgt agcgccgatg gtagtgtggg    1500
gtctccccat gcgagagtag ggaactgcca ggcatcaaat aaaacgaaag gctcagtcga    1560
aagactgggc ctttcgtttt atctgttgtt tgtcggtgaa cgctctcctg agtaggacaa    1620
atccgccggg agcggatttg aacgttgcga agcaacggcc cggagggtgg cgggcaggac    1680
gcccgccata aactgccagg catcaaatta agcagaaggc catcctgacg gatggccttt    1740
ttgcgtttct acaaactctt tttgtttatt tttctaaata cattcaaata tgtatccgct    1800
catgagacaa taaccctgat aaatgcttca ataatattga aaaggaaga gtatgagtat    1860 tcaacatttc cgtgtcgccc ttattccctt ttttgcggca ttttgccttc ctgttttttgc    1920 tcacccagaa acgctggtga agtaaaaga tgctgaagat cagttgggtg cacgagtggg    1980
ttacatcgaa ctggatctca acagcggtaa gatccttgag agttttcgcc ccgaagaacg    2040
ttttccaatg atgagcactt ttaaagttct gctatgtggc gcggtattat cccgtgttga    2100
cgccgggcaa gagcaactcg gtcgccgcat acactattct cagaatgact tggttgagta    2160
ctcaccagtc acagaaaagc atcttacgga tggcatgaca gtaagagaat tatgcagtgc    2220
tgccataacc atgagtgata acactgcggc caacttactt ctgacaacga tcggaggacc    2280
gaaggagcta accgcttttt tgcacaacat gggggatcat gtaactcgcc ttgatcgttg    2340
ggaaccggag ctgaatgaag ccataccaaa cgacgagcgt gacaccacga tgcctacagc    2400
aatggcaaca acgttgcgca aactattaac tggcgaacta cttactctag cttcccggca    2460
acaattaata gactggatgg aggcggataa agttgcagga ccacttctgc gctcggccct    2520
tccggctggc tggtttattg ctgataaatc tggagccggt gagcgtgggt ctcgcggtat    2580
cattgcagca ctggggccag atggtaagcc ctcccgtatc gtagttatct acacgacggg    2640
gagtcaggca actatggatg aacgaaatag acagatcgct gagataggtg cctcactgat    2700
taagcattgg taactgtcag accaagttta ctcatatata ctttagattg atttaaaact    2760
tcatttttaa tttaaaagga tctaggtgaa gatcctttt gataatctca tgaccaaaat    2820
cccttaacgt gagttttcgt tccactgagc gtcagacccc gtagaaaaga tcaaaggatc    2880
ttcttgagat ccttttttc tgcgcgtaat ctgctgcttg caaacaaaaa aaccaccgct    2940
accagcggtg gtttgtttgc cggatcaaga gctaccaact ctttttccga aggtaactgg    3000
cttcagcaga gcgcagatac caaatactgt ccttctagtg tagccgtagt taggccacca    3060
cttcaagaac tctgtagcac cgcctacata cctcgctctg ctaatcctgt taccagtggc    3120
tgctgccagt ggcgataagt cgtgtcttac cgggttggac tcaagacgat agttaccgga    3180
taaggcgcag cggtcgggct gaacggggggg ttcgtgcaca gcccagct tggagcgaac    3240 gacctacacc gaactgagat acctacagcg tgagctatga gaaagcgcca cgcttcccga    3300
agggagaaag gcggacaggt atccggtaag cggcagggtc ggaacaggag agcgcacgag    3360
ggagcttcca gggggaaacg cctggtatct ttatagtcct gtcgggtttc gccacctctg    3420
acttgagcgt cgatttttgt gatgctcgtc aggggggcgg agcctatgga aaaacgccag    3480
caacgcggcc tttttacggt tcctggcctt ttgctggcct tttgctcaca tgttctttcc    3540
```

```
tgcgttatcc cctgattctg tggataaccg tattaccgcc tttgagtgag ctgataccgc    3600
tcgccgcagc cgaacgaccg agcgcagcga gtcagtgagc gaggaagcgg aagagcgcct    3660
gatgcggtat tttctcctta cgcatctgtg cggtatttca caccgcatat g             3711

<210> SEQ ID NO 5
<211> LENGTH: 4089
<212> TYPE: DNA
<213> ORGANISM: Artificial Sequence
<220> FEATURE:
<223> OTHER INFORMATION: arabinose inducible plasmid expressing the
      construct with start codon at 351 and stop codon at 1664

<400> SEQUENCE: 5
gggggcggcc gcaagaaacc aattgtccat attgcatcag acattgccgt cactgcgtct      60
tttactggct cttctcgcta accaaaccgg taacccccgct tattaaaagc attctgtaac    120
aaagcgggac caaagccatg acaaaaacgc gtaacaaaag tgtctataat cacggcagaa    180
aagtccacat tgattatttg cacggcgtca cactttgcta tgccatagca ttttatcca     240 taagattagc ggatcctacc tgacgctttt tatcgcaact ctctactgtt tctccatacc    300 cgttttttg gctagcgaa ttcgagctcg gtacccagga ggaattcacc atggctaaaa      360
agacagctat cgcgattgca gtggcactgg ctggtttcgc taccgtagcg caggcagctg    420
tggtgagcca ttttaacgat tgcccggata gccataccca gttttgcttt catggcacct    480
gccgctttct ggtgcaggaa gataaaccgg cgtgcgtgtg ccatagcggt tatgtgggcg    540
ctcgctgcga acatgcggat ctgctggccc atcaactagt gggcggtggt ggcagtggtg    600
gcggcggctc tggtggtggc gggtcccggg gtggcagcct ggccgcgctg accgcgcacc    660
aggcttgcca cctgccgctg gagactttca cccgtcatcg ccagccgcgc ggctgggaac    720
aactggagca gtgcggctat ccggtgcagc ggctggtcgc cctctacctg cggcgcggc     780 tgtcgtggaa ccaggtcgac caggtgatcc gcaacgccct ggccagcccc ggcagcggcg    840
gcgacctggg cgaagcgatc cgcgagcagc cggagcaggc ccgtctggcc ctgaccctgg    900
ccgccgccga gagcgagcgc ttcgtccggc agggcaccgg caacgacgag gccggcgcgg    960
ccaacgcccc ggcggacagc ggcgacgccc tgctggagcg caactatccc actggcgcgg   1020
agttcctcgg cgacgtcggc gacgtcagct tcagcacccg cggcacgcag aactggacgg   1080
tggagcggct gctccaggcg caccgccaac tggaggagcg cggctatgtg ttcgtcggct   1140
accacggcac cttcctcgaa gcggcgcaaa gcatcgtctt cggcggggtg cgcgcgcgca   1200
gccaggacct cgacgcgatc tggcgcggtt tctatatcgc cggcgatccg gcgctggcct   1260
acggctacgc ccaggaccag gaacccgacg cacgcggccg gatccgcaac ggtgccctgc   1320
tgcgggtcta tgtgccgcgc tcgagcctgc cgggcttcta ccgcaccagc ctgacccgg    1380 ccgcgccgga ggcggcgggc gaggtcgaac ggctgatcgg ccatccgctg ccgctgcgcc   1440
tggacgccat caccggcccc gaggaggaag gcgggcgcct ggagaccatt ctcggctggc   1500
cgctggccga gcgcaccgtg gtgattccct cggcgatccc caccgacccg cgcaacgtcg   1560
gcggcgacct cgaccgtcc agcatccccg acaaggaaca ggcgatcagc gcctgccgg    1620 actacgccag ccagcccggc aaaccgccga agatgaact gtaactcgag tagatctgta   1680
ctctagagtc gacctgcagg catgcaagct tggctgtttt ggcggatgag agaagatttt   1740
cagcctgata cagattaaat cagaacgcag aagcggtctg ataaaacaga atttgcctgg   1800
cggcagtagc gcggtggtcc cacctgaccc catgccgaac tcagaagtga aacgccgtag   1860
```

```
cgccgatggt agtgtggggt ctccccatgc gagagtaggg aactgccagg catcaaataa    1920
aacgaaaggc tcagtcgaaa gactgggcct ttcgttttat ctgttgtttg tcggtgaacg    1980
ctctcctgag taggacaaat ccgccgggag cggatttgaa cgttgcgaag caacggcccg    2040
gagggtggcg ggcaggacgc ccgccataaa ctgccaggca tcaaattaag cagaaggcca    2100
tcctgacgga tggcctttt gcgtttctac aaactctttt tgtttatttt tctaaataca    2160
ttcaaatatg tatccgctca tgagacaata accctgataa atgcttcaat aatattgaaa    2220
aaggaagagt atgagtattc aacatttccg tgtcgccctt attccctttt ttgcggcatt    2280
ttgccttcct gtttttgctc acccagaaac gctggtgaaa gtaaaagatg ctgaagatca    2340
gttgggtgca cgagtgggtt acatcgaact ggatctcaac agcggtaaga tccttgagag    2400
ttttcgcccc gaagaacgtt ttccaatgat gagcactttt aaagttctgc tatgtggcgc    2460
ggtattatcc cgtgttgacg ccgggcaaga gcaactcggt cgccgcatac actattctca    2520
gaatgacttg gttgagtact caccagtcac agaaaagcat cttacggatg gcatgacagt    2580
aagagaatta tgcagtgctg ccataaccat gagtgataac actgcggcca acttacttct    2640
gacaacgatc ggaggaccga aggagctaac cgcttttttg cacaacatgg gggatcatgt    2700
aactcgcctt gatcgttggg aaccggagct gaatgaagcc ataccaaacg acgagcgtga    2760
caccacgatg cctacagcaa tggcaacaac gttgcgcaaa ctattaactg gcgaactact    2820
tactctagct tcccggcaac aattaataga ctggatggag gcggataaag ttgcaggacc    2880
acttctgcgc tcggcccttc cggctggctg gtttattgct gataaatctg gagccggtga    2940
gcgtgggtct cgcggtatca ttgcagcact ggggccagat ggtaagccct cccgtatcgt    3000
agttatctac acgacgggga gtcaggcaac tatggatgaa cgaaatagac agatcgctga    3060
gataggtgcc tcactgatta agcattggta actgtcagac caagtttact catatatact    3120
ttagattgat ttaaaacttc attttaatt taaaaggatc taggtgaaga tcctttttga    3180
taatctcatg accaaaatcc cttaacgtga gttttcgttc cactgagcgt cagacccgt    3240
agaaaagatc aaaggatctt cttgagatcc tttttttctg cgcgtaatct gctgcttgca    3300
aacaaaaaaa ccaccgctac cagcggtggt ttgtttgccg gatcaagagc taccaactct    3360
tttccgaag gtaactggct tcagcagagc gcagatacca aatactgtcc ttctagtgta    3420
gccgtagtta ggccaccact tcaagaactc tgtagcaccg cctacatacc tcgctctgct    3480
aatcctgtta ccagtggctg ctgccagtgg cgataagtcg tgtcttaccg ggttggactc    3540
aagacgatag ttaccggata aggcgcagcg gtcgggctga acggggggtt cgtgcacaca    3600
gcccagcttg gagcgaacga cctacaccga actgagatac ctacagcgtg agctatgaga    3660
aagcgccacg cttcccgaag ggagaaaggc ggacaggtat ccggtaagcg gcagggtcgg    3720
aacaggagag cgcacgaggg agcttccagg gggaaacgcc tggtatcttt atagtcctgt    3780
cgggtttcgc cacctctgac ttgagcgtcg attttgtga tgctcgtcag ggggcggag    3840
cctatggaaa aacgccagca acgcggcctt tttacggttc ctggccttt gctggccttt    3900
tgctcacatg ttctttcctg cgttatcccc tgattctgtg ataaccgta ttaccgcctt    3960
tgagtgagct gataccgctc gccgcagccg aacgaccgag cgcagcgagt cagtgagcga    4020
ggaagcggaa gagcgcctga tgcggtattt tctccttacg catctgtgcg gtatttcaca    4080
ccgcatatg                                                           4089
```

<210> SEQ ID NO 6

<211> LENGTH: 4238
<212> TYPE: DNA
<213> ORGANISM: Artificial Sequence
<220> FEATURE:
<223> OTHER INFORMATION: arabinose inducible plasmid expressing the
      construct with start codon at 351, a stop codon at 1664, and
      colicin E3 lysis protein from 1699 to 1842

<400> SEQUENCE: 6

| | | | | | |
|---|---|---|---|---|---|
| gggggcggcc | gcaagaaacc | aattgtccat | attgcatcag | acattgccgt | cactgcgtct | 60 |
| tttactggct | cttctcgcta | accaaaccgg | taaccccgct | tattaaaagc | attctgtaac | 120 |
| aaagcgggac | caaagccatg | acaaaaacgc | gtaacaaaag | tgtctataat | cacggcagaa | 180 |
| aagtccacat | tgattatttg | cacggcgtca | cactttgcta | tgccatagca | tttttatcca | 240 |
| taagattagc | ggatcctacc | tgacgctttt | tatcgcaact | ctctactgtt | tctccatacc | 300 |
| cgttttttg  | ggctagcgaa | ttcgagctcg | gtacccagga | ggaattcacc | atggctaaaa | 360 |
| agacagctat | cgcgattgca | gtggcactgg | ctggtttcgc | taccgtagcg | caggcagctg | 420 |
| tggtgagcca | ttttaacgat | tgcccggata | gccataccca | gttttgcttt | catggcacct | 480 |
| gccgctttct | ggtgcaggaa | gataaaccgg | cgtgcgtgtg | ccatagcggt | tatgtgggcg | 540 |
| ctcgctgcga | acatgcggat | ctgctggccc | atcaactagt | gggcggtggt | ggcagtggtg | 600 |
| gcggcggctc | tggtggtggc | gggtcccggg | gtggcagcct | ggccgcgctg | accgcgcacc | 660 |
| aggcttgcca | cctgccgctg | gagactttca | cccgtcatcg | ccagccgcgc | ggctgggaac | 720 |
| aactggagca | gtgcggctat | ccggtgcagc | ggctggtcgc | cctctacctg | cggcgcggc  | 780 |
| tgtcgtggaa | ccaggtcgac | caggtgatcc | gcaacgccct | ggccagcccc | ggcagcggcg | 840 |
| gcgacctggg | cgaagcgatc | cgcgagcagc | cggagcaggc | ccgtctggcc | ctgaccctgg | 900 |
| ccgccgccga | gagcgagcgc | ttcgtccggc | agggcaccgg | caacgacgag | gccggcgcgg | 960 |
| ccaacgcccc | ggcggacagc | ggcgacgccc | tgctggagcg | caactatccc | actggcgcgg | 1020 |
| agttcctcgg | cgacgcggc  | gacgtcagct | tcagcacccg | cggcacgcag | aactggacgg | 1080 |
| tggagcggct | gctccaggcg | caccgccaac | tggaggagcg | cggctatgtg | ttcgtcggct | 1140 |
| accacggcac | cttcctcgaa | gcggcgcaaa | gcatcgtctt | cggcggggtg | cgcgcgcgca | 1200 |
| gccaggacct | cgacgcgatc | tggcgcggtt | tctatatcgc | cggcgatccg | gcgctggcct | 1260 |
| acggctacgc | ccaggaccag | gaacccgacg | cacgcggccg | gatccgcaac | ggtgccctgc | 1320 |
| tgcgggtcta | tgtgccgcgc | tcgagcctgc | cgggcttcta | ccgcaccagc | ctgaccctgg | 1380 |
| ccgccggga  | ggcggcgggc | gaggtcgaac | ggctgatcgg | ccatccgctg | ccgctgcgcc | 1440 |
| tggacgccat | caccggcccc | gaggaggaag | gcgggcgcct | ggagaccatt | ctcggctggc | 1500 |
| cgctggccga | gcgcaccgtg | gtgattccct | cggcgatccc | caccgacccg | cgcaacgtcg | 1560 |
| gcggcgacct | cgacccgtcc | agcatccccg | acaaggaaca | ggcgatcagc | gccctgccgg | 1620 |
| actacgccag | ccagcccggc | aaaccgccga | aagatgaact | gtaactcgag | tagatctgta | 1680 |
| ctctagaaag | gagtcgttat | gaaaaaaata | acagggatta | ttttattgct | tcttgcagtc | 1740 |
| attattctgt | ctgcatgtca | ggcaaactat | atccgggatg | ttcagggcgg | gaccgtatct | 1800 |
| ccgtcatcaa | cagctgaagt | gaccggatta | gcaacgcagt | aactgcaggc | atgcaagctt | 1860 |
| ggctgttttg | gcggatgaga | gaagattttc | agcctgatac | agattaaatc | agaacgcaga | 1920 |
| agcggtctga | taaaacagaa | tttgcctggc | ggcagtagcg | cggtggtccc | acctgacccc | 1980 |
| atgccgaact | cagaagtgaa | acgccgtagc | gccgatggta | gtgtggggtc | tccccatgcg | 2040 |
| agagtaggga | actgccaggc | atcaaataaa | acgaaaggct | cagtcgaaag | actgggcctt | 2100 |

```
tcgttttatc tgttgtttgt cggtgaacgc tctcctgagt aggacaaatc cgccgggagc    2160
ggatttgaac gttgcgaagc aacggcccgg agggtggcgg gcaggacgcc cgccataaac    2220
tgccaggcat caaattaagc agaaggccat cctgacggat ggccttttg cgtttctaca     2280 aactcttttt gtttattttt ctaaatacat tcaaatatgt atccgctcat gagacaataa    2340
ccctgataaa tgcttcaata atattgaaaa aggaagagta tgagtattca acatttccgt    2400
gtcgccctta ttcccttttt tgcggcattt tgccttcctg tttttgctca cccagaaacg    2460
ctggtgaaag taaaagatgc tgaagatcag ttgggtgcac gagtgggtta tcgaactg     2520 gatctcaaca gcggtaagat ccttgagagt tttcgccccg aagaacgttt tccaatgatg    2580
agcactttta aagttctgct atgtggcgcg gtattatccc gtgttgacgc cgggcaagag    2640
caactcggtc gccgcataca ctattctcag aatgacttgg ttgagtactc accagtcaca    2700
gaaaagcatc ttacggatgg catgacagta agagaattat gcagtgctgc cataaccatg    2760
agtgataaca ctgcggccaa cttacttctg acaacgatcg gaggaccgaa ggagctaacc    2820
gcttttttgc acaacatggg ggatcatgta actcgccttg atcgttggga accggagctg    2880
aatgaagcca taccaaacga cgagcgtgac accacgatgc ctacagcaat ggcaacaacg    2940
ttgcgcaaac tattaactgg cgaactactt actctagctt cccggcaaca attaatagac    3000
tggatggagg cggataaagt tgcaggacca cttctgcgct cggcccttcc ggctggctgg    3060
tttattgctg ataaatctgg agccggtgag cgtgggtctc gcggtatcat tgcagcactg    3120
gggccagatg gtaagccctc ccgtatcgta gttatctaca cgacggggag tcaggcaact    3180
atggatgaac gaaatagaca gatcgctgag ataggtgcct cactgattaa gcattggtaa    3240
ctgtcagacc aagtttactc atatatactt tagattgatt taaaacttca tttttaattt    3300
aaaaggatct aggtgaagat cctttttgat aatctcatga ccaaaatccc ttaacgtgag    3360
ttttcgttcc actgagcgtc agaccccgta gaaaagatca aaggatcttc ttgagatcct    3420 tttttttctgc gcgtaatctg ctgcttgcaa acaaaaaaac caccgctacc agcggtggtt    3480
tgtttgccgg atcaagagct accaactctt tttccgaagg taactggctt cagcagagcg    3540
cagataccaa atactgtcct tctagtgtag ccgtagttag gccaccactt caagaactct    3600
gtagcaccgc ctacatacct cgctctgcta atcctgttac cagtggctgc tgccagtggc    3660
gataagtcgt gtcttaccgg gttggactca agacgatagt taccggataa ggcgcagcgg    3720
tcgggctgaa cggggggttc gtgcacacag cccagcttgg agcgaacgac ctacaccgaa    3780
ctgagatacc tacagcgtga gctatgagaa agcgccacgc ttcccgaagg gagaaaggcg    3840
gacaggtatc cggtaagcgg cagggtcgga acaggagagc gcacgaggga gcttccaggg    3900
ggaaacgcct ggtatcttta tagtcctgtc gggtttcgcc acctctgact tgagcgtcga    3960
tttttgtgat gctcgtcagg gggcggagc ctatggaaaa acgccagcaa cgcggccttt     4020
ttacggttcc tggccttttg ctggcctttt gctcacatgt tctttcctgc gttatcccct    4080
gattctgtgg ataaccgtat taccgccttt gagtgagctg ataccgctcg ccgcagccga    4140
acgaccgagc gcagcgagtc agtgagcgag gaagcggaag agcgcctgat gcggtatttt    4200
ctccttacgc atctgtgcgg tatttcacac cgcatatg                            4238
```

<210> SEQ ID NO 7
<211> LENGTH: 4770
<212> TYPE: DNA
<213> ORGANISM: Artificial Sequence
<220> FEATURE:

<223> OTHER INFORMATION: arabinose inducible plasmid expressing the
     construct with cldtB start codon at 351, stop codon at 1163, pltB
     start at 1197, stop at 1610, and pltA 1627-2355

<400> SEQUENCE: 7

| | | | | | |
|---|---|---|---|---|---|
| gggggcggcc | gcaagaaacc | aattgtccat | attgcatcag | acattgccgt | cactgcgtct | 60 |
| tttactggct | cttctcgcta | accaaaccgg | taaccccgct | tattaaaagc | attctgtaac | 120 |
| aaagcgggac | caaagccatg | acaaaaacgc | gtaacaaaag | tgtctataat | cacggcagaa | 180 |
| aagtccacat | tgattatttg | cacggcgtca | cactttgcta | tgccatagca | tttttatcca | 240 |
| taagattagc | ggatcctacc | tgacgctttt | tatcgcaact | ctctactgtt | tctccatacc | 300 |
| cgttttttg | ggctagcgaa | ttcgagctcg | tacccagga | ggaattcacc | atggtcaaaa | 360 |
| aacctgtttt | tttccttctg | accatgatca | tctgcagcta | tatttctttt | gcctgcgcta | 420 |
| atatcagtga | ctacaaagtt | atgacctgga | atcttcaggg | ctcttcagca | tctacagaaa | 480 |
| gtaaatggaa | tgtcaatgtc | agacagcttt | taagcggtac | tgccggtgtg | atattctta | 540 |
| tggtacagga | ggccggtgct | gttcccacct | cagcggttcc | taccggacga | catattcagc | 600 |
| cttttggagt | gggtattccc | attgatgaat | acacctggaa | tctcggaacc | accagccgtc | 660 |
| aggatataag | atatatctac | tactcggcta | ttgatgttgg | agcacgccgt | gttaatctgg | 720 |
| caatagtttc | cagacaaaga | gcggataatg | tttatgtctt | gcgtccgaca | actgtcgcat | 780 |
| ctcgccccgt | cattggcatc | ggactgggta | atgatgtttt | tctgacagcg | cacgcactgg | 840 |
| ctagtggagg | tccggatgct | gcagctattg | tcagggttac | cattaatttt | tttagacaac | 900 |
| ctcagatgcg | gcatttatcc | tggtttcttg | ccggggattt | taatcgcagc | ccagacagac | 960 |
| ttgaaaatga | cctgatgact | gagcatctgg | aacgagttgt | agccgtactc | gcacctacag | 1020 |
| aacccacgca | aattagcggt | ggtatttag | attatgcggt | cattgtcgat | cgagcacctt | 1080 |
| attcacaaag | ggtcgaagca | ttacgtaatc | cacaactcgc | ttctgatcat | tatcccgtag | 1140 |
| cctttttggc | acgaagctgt | taatgatcta | gataagtcga | cgtacaggag | agtagtatgt | 1200 |
| atataaataa | gtttgtgcct | gtttatacat | tattaattct | catttattct | tttaatgcca | 1260 |
| gcgctgagtg | gacaggagat | aatacgaacg | cctattactc | agacgaagtt | atcagtgaat | 1320 |
| tacatgttgg | tcagatagat | actagtcctt | attttttgcat | aaaaacggtt | aaagctaacg | 1380 |
| gtagtggtac | accagttgtt | gcatgtgcgg | tatcaaagca | gagcatatgg | gcgcccctcct | 1440 |
| ttaaagaact | tcttgatcag | gcaagatatt | tttacagtac | agggcaatcc | gtaaggattc | 1500 |
| atgttcaaaa | aaatatctgg | acctatccgc | tttttgttaa | tacctttca | gcaaatgctc | 1560 |
| ttgtgggact | atcatcgtgc | agtgcgacac | aatgctttgg | acccaagtaa | gaggggagaa | 1620 |
| gaaataatga | aaaagttaat | attcttaacc | ttatctatag | ttagctttaa | taactatgct | 1680 |
| gtagattttg | tgtatcgtgt | ggactcaacc | ccgccggacg | ttatttttcg | cgatgggttt | 1740 |
| tcactacttg | ggtataaccg | taactttcag | caatttatta | gtggaaggtc | atgtagtggt | 1800 |
| ggaagtagtg | acagtcgcta | tattgcaaca | acctcaagtg | ttaatcaaac | atatgctata | 1860 |
| gccagagcgt | actattctcg | ctcaacattc | aaaggtaatt | tatacagata | tcagattcgt | 1920 |
| gcagataata | atttctacag | cttgctccca | tccatcacct | atctggaaac | gcaaggtggt | 1980 |
| cactttaatg | cttatgaaaa | aacgatgatg | cgattgcaaa | gagagtatgt | ttccacatta | 2040 |
| tctattttac | ccgagaatat | tcaaaaggcc | gtgtgcgctag | tttatgatag | cgcaaccggt | 2100 |
| ctggtaaagg | atggtgtaag | cacaatgaat | gccagttatt | taggtttaag | cactacgtct | 2160 |
| aatcctggtg | tgataccttt | tcttccggaa | ccgcagacgt | atacccaaca | acgaattgat | 2220 |

```
gcattcggcc cattaataag ttcatgcttt tcaataggta gcgtatgtca gtcacatcga    2280
gggcaaagag ctgacgtata caacatgtct ttttatgatg caagacctgt aatagaactt    2340
atactttcta aataaatgaa acttacctat gttgccgcat gcaagctagc ttggctgttt    2400
tggcggatga gagaagattt tcagcctgat acagattaaa tcagaacgca gaagcggtct    2460
gataaaacag aatttgcctg gcggcagtag cgcggtggtc ccacctgacc ccatgccgaa    2520
ctcagaagtg aaacgccgta gcgccgatgg tagtgtgggg tctccccatg cgagagtagg    2580
gaactgccag gcatcaaata aaacgaaagg ctcagtcgaa agactgggcc tttcgtttta    2640
tctgttgttt gtcggtgaac gctctcctga gtaggacaaa tccgccggga gcggatttga    2700
acgttgcgaa gcaacggccc ggagggtggc gggcaggacg cccgccataa actgccaggc    2760
atcaaattaa gcagaaggcc atcctgacgg atggccttt tgcgtttcta caaactcttt    2820
ttgtttattt ttctaaatac attcaaatat gtatccgctc atgagacaat aaccctgata    2880
aatgcttcaa taatattgaa aaaggaagag tatgagtatt caacatttcc gtgtcgccct    2940 tattccctt tttgcggcat tttgccttcc tgttttgct cacccagaaa cgctggtgaa    3000
agtaaaagat gctgaagatc agttgggtgc acgagtgggt tacatcgaac tggatctcaa    3060
cagcggtaag atccttgaga gttttcgccc cgaagaacgt tttccaatga tgagcacttt    3120
taaagttctg ctatgtggcg cggtattatc ccgtgttgac gccgggcaag agcaactcgg    3180
tcgccgcata cactattctc agaatgactt ggttgagtac tcaccagtca cagaaaagca    3240
tcttacggat ggcatgacag taagagaatt atgcagtgct gccataacca tgagtgataa    3300
cactgcggcc aacttacttc tgacaacgat cggaggaccg aaggagctaa ccgcttttt    3360 gcacaacatg ggggatcatg taactcgcct tgatcgttgg gaaccggagc tgaatgaagc    3420
cataccaaac gacgagcgtg acaccacgat gcctacagca atggcaacaa cgttgcgcaa    3480
actattaact ggcgaactac ttactctagc ttcccggcaa caattaatag actggatgga    3540
ggcggataaa gttgcaggac cacttctgcg ctcggccctt ccggctggct ggtttattgc    3600
tgataaatct ggagccggtg agcgtgggtc tcgcggtatc attgcagcac tggggccaga    3660
tggtaagccc tcccgtatcg tagttatcta cacgacgggg agtcaggcaa ctatggatga    3720
acgaaataga cagatcgctg agataggtgc ctcactgatt aagcattggt aactgtcaga    3780
ccaagtttac tcatatatac tttagattga tttaaaactt catttttaat ttaaaaggat    3840
ctaggtgaag atcctttttg ataatctcat gaccaaaatc ccttaacgtg agttttcgtt    3900
ccactgagcg tcagaccccg tagaaaagat caaaggatct tcttgagatc ctttttttct    3960
gcgcgtaatc tgctgcttgc aaacaaaaaa accaccgcta ccagcggtgg tttgtttgcc    4020
ggatcaagag ctaccaactc tttttccgaa ggtaactggc ttcagcagag cgcagatacc    4080
aaatactgtc cttctagtgt agccgtagtt aggccaccac ttcaagaact ctgtagcacc    4140
gcctacatac ctcgctctgc taatcctgtt accagtggct gctgccagtg gcgataagtc    4200
gtgtcttacc gggttggact caagacgata gttaccggat aaggcgcagc ggtcgggctg    4260
aacggggggt tcgtgcacac agcccagctt ggagcgaacg acctacaccg aactgagata    4320
cctacagcgt gagctatgag aaagcgccac gcttcccgaa gggagaaagg cggacaggta    4380
tccggtaagc ggcagggtcg gaacaggaga gcgcacgagg gagcttccag ggggaaacgc    4440
ctggtatctt tatagtcctg tcgggtttcg ccacctctga cttgagcgtc gatttttgtg    4500
atgctcgtca ggggggcgga gcctatggaa aaacgccagc aacgcggcct ttttacggtt    4560
```

```
cctggccttt tgctggcctt ttgctcacat gttctttcct gcgttatccc ctgattctgt    4620
ggataaccgt attaccgcct ttgagtgagc tgataccgct cgccgcagcc gaacgaccga    4680
gcgcagcgag tcagtgagcg aggaagcgga agagcgcctg atgcggtatt ttctccttac    4740
gcatctgtgc ggtatttcac accgcatatg                                     4770

<210> SEQ ID NO 8
<211> LENGTH: 15
<212> TYPE: DNA
<213> ORGANISM: Artificial Sequence
<220> FEATURE:
<223> OTHER INFORMATION: Linker x3

<400> SEQUENCE: 8
ggggsggggs gggs                                                        15

<210> SEQ ID NO 9
<211> LENGTH: 4851
<212> TYPE: DNA
<213> ORGANISM: Artificial Sequence
<220> FEATURE:
<223> OTHER INFORMATION: arabinose inducible plasmid with a cldtB start
      codon at 351 through codon at 1160 (without a stop), FLAG from
      1170-1193, and GGGGS(x3) from 1194-1238, pltB start at 1278 and
      stop at 1691 and pltA 1708-2436

<400> SEQUENCE: 9 ggggcggcc gcaagaaacc aattgtccat attgcatcag acattgccgt cactgcgtct      60
tttactggct cttctcgcta accaaaccgg taaccccgct tattaaaagc attctgtaac    120
aaagcgggac caaagccatg acaaaaacgc gtaacaaaag tgtctataat cacggcagaa    180
aagtccacat tgattatttg cacggcgtca cactttgcta tgccatagca ttttatccca    240
taagattagc ggatcctacc tgacgctttt tatcgcaact ctctactgtt tctccatacc    300 cgttttttg gctagcgaa ttcgagctcg gtacccagga ggaattcacc atggtcaaaa     360
aacctgtttt tttccttctg accatgatca tctgcagcta tatttctttt gcctgcgcta    420
atatcagtga ctacaaagtt atgacctgga atcttcaggg ctcttcagca tctacagaaa    480
gtaaatggaa tgtcaatgtc agacagcttt taagcggtac tgccggtgtg atattctta    540 tggtacagga ggccggtgct gttcccacct cagcggttcc taccggacga catattcagc    600
cttttggagt gggtattccc attgatgaat acacctggaa tctcggaacc accagccgtc    660
aggatataag atatatctac tactcggcta ttgatgttgg agcacgccgt gttaatctgg    720
caatagtttc cagacaaaga gcggataatg tttatgtctt gcgtccgaca actgtcgcat    780
ctcgccccgt cattggcatc ggactgggta tgatgttttt tctgacagcg cacgcactgg    840
ctagtggagg tccggatgct gcagctattg tcagggttac cattaatttt tttagacaac    900
ctcagatgcg gcatttatcc tggtttcttg ccggggattt taatcgcagc ccagacagac    960
ttgaaaatga cctgatgact gagcatctgg aacgagttgt agccgtactc gcacctacag    1020
aacccacgca aattagcggt ggtatttag attatgggt cattgtcgat cgagcacctt    1080
attcacaaag gtcgaagca ttacgtaatc cacaactcgc ttctgatcat tatcccgtag    1140
cctttttggc acgaagctgt ataccaggtg attataaaga tgacgatgac aaaggcggtg    1200
gcggtagcgg cggtggcggt tctggcggtg gcggtagtaa gcttgggtct agataggtcg    1260
acgtacagga gagtagtatg tatataaata agtttgtgcc tgtttataca ttattaattc    1320
tcatttattc ttttaatgcc agcgctgagt ggacaggaga taatacgaac gcctattact    1380
```

```
cagacgaagt tatcagtgaa ttacatgttg gtcagataga tactagtcct tattttttgca      1440
taaaaacggt taaagctaac ggtagtggta caccagttgt tgcatgtgcg gtatcaaagc      1500
agagcatatg ggcgccctcc tttaaagaac ttcttgatca ggcaagatat ttttacagta      1560
cagggcaatc cgtaaggatt catgttcaaa aaaatatctg gacctatccg cttttttgtta    1620
atacctttc agcaaatgct cttgtgggac tatcatcgtg cagtgcgaca caatgctttg      1680
gacccaagta agaggggaga agaaataatg aaaaagttaa tattcttaac cttatctata      1740
gttagctttta ataactatgc tgtagatttt gtgtatcgtg tggactcaac cccgccggac   1800
gttattttttc gcgatgggtt ttcactactt gggtataacc gtaactttca gcaatttatt   1860
agtggaaggt catgtagtgg tggaagtagt gacagtcgct atattgcaac aacctcaagt    1920
gttaatcaaa catatgctat agccagagcg tactattctc gctcaacatt caaaggtaat    1980
ttatacagat atcagattcg tgcagataat aatttctaca gcttgctccc atccatcacc    2040
tatctggaaa cgcaaggtgg tcactttaat gcttatgaaa aaacgatgat gcgattgcaa    2100
agagagtatg tttccacatt atctatttta cccgagaata ttcaaaaggc cgtggcgcta    2160
gtttatgata gcgcaaccgg tctggtaaag gatggtgtaa gcacaatgaa tgccagttat    2220
ttaggtttaa gcactacgtc taatcctggt gtgataccttt tcttccgga accgcagacg    2280
tatcccaac aacgaattga tgcattcggc ccattaataa gttcatgctt tcaataggt     2340
agcgtatgtc agtcacatcg agggcaaaga gctgacgtat acaacatgtc ttttttatgat  2400
gcaagacctg taatagaact tatactttct aaataaatga aacttaccta tgttgccgca    2460
tgcaagctag cttggctgtt ttggcggatg agagaagatt ttcagcctga tacagattaa   2520
atcagaacgc agaagcggtc tgataaaaca gaatttgcct ggcggcagta gcgcggtggt   2580
cccacctgac cccatgccga actcagaagt gaaacgccgt agcgccgatg gtagtgtggg    2640
gtctccccat gcgagagtag ggaactgcca ggcatcaaat aaaacgaaag gctcagtcga    2700
aagactgggc ctttcgtttt atctgttgtt tgtcggtgaa cgctctcctg agtaggacaa    2760
atccgccggg agcggatttg aacgttgcga agcaacggcc cggagggtgg cgggcaggac   2820
gcccgccata aactgccagg catcaaatta agcagaaggc catcctgacg gatggccttt    2880
ttgcgtttct acaaactctt tttgttatt tttctaaata cattcaaata tgtatccgct     2940
catgagacaa taaccctgat aaatgcttca ataatattga aaaggaaga gtatgagtat     3000
tcaacatttc cgtgtcgccc ttattccctt ttttgcggca ttttgccttc ctgtttttgc     3060
tcacccagaa acgctggtga agtaaaaga tgctgaagat cagttgggtg cacgagtggg    3120
ttacatcgaa ctggatctca acagcggtaa gatccttgag agttttcgcc ccgaagaacg    3180
tttttccaatg atgagcactt ttaaagttct gctatgtggc gcggtattat cccgtgttga    3240
cgccgggcaa gagcaactcg gtcgccgcat acactattct cagaatgact tggttgagta    3300
ctcaccagtc acagaaaagc atcttacgga tggcatgaca gtaagagaat tatgcagtgc    3360
tgccataacc atgagtgata acactgcggc caacttactt ctgacaacga tcggaggacc    3420
gaaggagcta accgcttttt tgcacaacat ggggatcat gtaactcgcc ttgatcgttg    3480
ggaaccggag ctgaatgaag ccataccaaa cgacgagcgt gacaccacga tgcctacagc    3540
aatggcaaca acgttgcgca aactattaac tggcgaacta cttactctag cttcccggca    3600
acaattaata gactgatgg aggcggataa agttgcagga ccacttctgc gctcggccct   3660
tccggctggc tggtttattg ctgataaatc tggagccggt gagcgtgggt ctcgcggtat   3720
cattgcagca ctggggccag atggtaagcc ctcccgtatc gtagttatct acacgacggg   3780
```

```
gagtcaggca actatggatg aacgaaatag acagatcgct gagataggtg cctcactgat    3840
taagcattgg taactgtcag accaagttta ctcatatata ctttagattg atttaaaact    3900
tcattttaa tttaaaagga tctaggtgaa gatccttttt gataatctca tgaccaaaat    3960
cccttaacgt gagttttcgt tccactgagc gtcagacccc gtagaaaaga tcaaaggatc    4020
ttcttgagat ccttttttc tgcgcgtaat ctgctgcttg caaacaaaaa aaccaccgct    4080
accagcggtg gtttgtttgc cggatcaaga gctaccaact cttttccga aggtaactgg    4140
cttcagcaga gcgcagatac caaatactgt ccttctagtg tagccgtagt taggccacca    4200
cttcaagaac tctgtagcac cgcctacata cctcgctctg ctaatcctgt taccagtggc    4260
tgctgccagt ggcgataagt cgtgtcttac cgggttggac tcaagacgat agttaccgga    4320
taaggcgcag cggtcgggct gaacggggggt tcgtgcaca cagcccagct tggagcgaac    4380
gacctacacc gaactgagat acctacagcg tgagctatga gaaagcgcca cgcttcccga    4440
agggagaaag gcggacaggt atccggtaag cggcagggtc ggaacaggag agcgcacgag    4500
ggagcttcca gggggaaacg cctggtatct ttatagtcct gtcgggtttc gccacctctg    4560
acttgagcgt cgatttttgt gatgctcgtc aggggggcgg agcctatgga aaaacgccag    4620
caacgcggcc tttttacggt tcctggcctt ttgctggcct tttgctcaca tgttctttcc    4680
tgcgttatcc cctgattctg tggataaccg tattaccgcc tttgagtgag ctgataccgc    4740
tcgccgcagc cgaacgaccg agcgcagcga gtcagtgagc gaggaagcgg aagagcgcct    4800
gatgcggtat tttctcctta cgcatctgtg cggtatttca caccgcatat g             4851
```

<210> SEQ ID NO 10
<211> LENGTH: 5250
<212> TYPE: DNA
<213> ORGANISM: Artificial Sequence
<220> FEATURE:
<223> OTHER INFORMATION: arabinose inducible plasmid expressing the
      TAT-apoptin construct as a cldtB fusion, with TAT-apoptin inserted
      in-frame within the HindIII and XbaI sites introduced into typhoid
      toxin cldtB, with the TAT-apoptin coding sequence from 1245-1646

<400> SEQUENCE: 10

```
gggggcggcc gcaagaaacc aattgtccat attgcatcag acattgccgt cactgcgtct     60
tttactggct cttctcgcta accaaaccgg taacccgct tattaaaagc attctgtaac     120
aaagcgggac caaagccatg acaaaaacgc gtaacaaaag tgtctataat cacggcagaa    180
aagtccacat tgattatttg cacggcgtca cactttgcta tgccatagca ttttatcca    240
taagattagc ggatcctacc tgacgctttt tatcgcaact ctctactgtt tctccatacc    300
cgttttttg gctagcgaa ttcgagctcg gtacccagga ggaattcacc atggtcaaaa    360
aacctgtttt ttttccttctg accatgatca tctgcagcta tatttctttt gcctgcgcta    420
atatcagtga ctacaaagtt atgacctgga atcttcaggg ctcttcagca tctacagaaa    480
gtaaatggaa tgtcaatgtc agacagcttt taagcggtac tgccggtgtg gatattctta    540
tggtacagga ggccggtgct gttcccacct cagcggttcc taccggacga catattcagc    600
cttttggagt gggtattccc attgatgaat acacctggaa tctcggaacc accagccgtc    660
aggatataag atatatctac tactcggcta ttgatgttgg agcacgccgt gttaatctgg    720
caatagtttc cagacaaaga gcggataatg tttatgtctt gcgtccgaca actgtcgcat    780
ctcgccccgt cattggcatc ggactgggta atgatgtttt tctgacagcg cacgcactgg    840
ctagtggagg tccggatgct gcagctattg tcagggttac cattaatttt tttagacaac    900
```

```
ctcagatgcg gcatttatcc tggtttcttg ccggggattt taatcgcagc ccagacagac    960
ttgaaaatga cctgatgact gagcatctgg aacgagttgt agccgtactc gcacctacag   1020
aacccacgca aattagcggt ggtattttag attatggggt cattgtcgat cgagcacctt   1080
attcacaaag ggtcgaagca ttacgtaatc cacaactcgc ttctgatcat tatcccgtag   1140
cctttttggc acgaagctgt ataccaggtg attataaaga tgacgatgac aaaggcggtg   1200
gcggtagcgg cggtggcggt tctggcggtg gcggtagtaa gcttatggca tacggtcgca   1260
agaaacgtcg tcaacgccgc cgcatgaacg ccctgcaaga agacacgccg ccgggtccga   1320
gcacggtttt tcgtccgccg accagctctc gcccgctgga aacgccgcat tgccgtgaaa   1380
ttcgcatcgg cattgcaggt atcaccatta cgctgtctct gtgcggctgt gcaaacgcac   1440
gtgcaccgac cctgcgctcc gctacggcgg ataacagtga atccaccggt tttaaaaatg   1500
tgccggatct gcgtacggac cagccgaagc cgccgtcaaa aaagcgttcg tgtgacccga   1560
gcgaatatcg cgttagcgaa ctgaaagaat ctctgattac cacgaccccg tcccgtccgc   1620
gcaccgcaaa acgccgcatc cgtctgtcta gataggtcga cgtacaggag agtagtatgt   1680
atataaataa gtttgtgcct gtttatacat tattaattct catttattct tttaatgcca   1740
gcgctgagtg gacaggagat aatacgaacg cctattactc agacgaagtt atcagtgaat   1800
tacatgttgg tcagatagat actagtcctt attttttgcat aaaaacggtt aaagctaacg   1860
gtagtggtac accagttgtt gcatgtgcgg tatcaaagca gagcatatgg gcgccctcct   1920
ttaaagaact tcttgatcag gcaagatatt tttacagtac agggcaatcc gtaaggattc   1980
atgttcaaaa aaatatctgg acctatccgc tttttgttaa tacctttttca gcaaatgctc   2040
ttgtgggact atcatcgtgc agtgcgacac aatgctttgg acccaagtaa gaggggagaa   2100
gaaataatga aaaagttaat attcttaacc ttatctatag ttagctttaa taactatgct   2160
gtagattttg tgtatcgtgt ggactcaacc ccgccggacg ttattttttcg cgatgggttt   2220
tcactacttg ggtataaccg taactttcag caatttatta gtggaaggtc atgtagtggt   2280
ggaagtagtg acagtcgcta tattgcaaca acctcaagtg ttaatcaaac atatgctata   2340
gccagagcgt actattctcg ctcaacattc aaaggtaatt tatacagata tcagattcgt   2400
gcagataata atttctacag cttgctccca tccatcacct atctggaaac gcaaggtggt   2460
cactttaatg cttatgaaaa aacgatgatg cgattgcaaa gagagtatgt ttccacatta   2520
tctattttac ccgagaatat tcaaaaggcc gtggcgctag tttatgatag cgcaaccggt   2580
ctggtaaagg atggtgtaag cacaatgaat gccagttatt taggtttaag cactacgtct   2640
aatcctggtg tgatacccttt tcttccggaa ccgcagacgt atacccaaca acgaattgat   2700
gcattcggcc cattaataag ttcatgcttt tcaataggta gcgtatgtca gtcacatcga   2760
gggcaaagag ctgacgtata caacatgtct ttttatgatg caagacctgt aatagaactt   2820
atactttcta aataaatgaa acttacctat gttgccgcat gcaagctagc ttggctgttt   2880
tggcggatga gagaagattt tcagcctgat acagattaaa tcagaacgca gaagcggtct   2940
gataaaacag aatttgcctg gcggcagtag cgcggtggtc ccacctgacc ccatgccgaa   3000
ctcagaagtg aaacgccgta gcgccgatgg tagtgtgggg tctccccatg cgagagtagg   3060
gaactgccag gcatcaaata aaacgaaagg ctcagtcgaa agactgggcc tttcgtttta   3120
tctgttgttt gtcggtgaac gctctcctga gtaggacaaa tccgccggga gcggatttga   3180
acgttgcgaa gcaacggccc ggagggtggc gggcaggacg cccgccataa actgccaggc   3240
```

```
atcaaattaa gcagaaggcc atcctgacgg atggccttttt tgcgtttcta caaactctttt   3300 ttgtttatttt ttctaaatac attcaaatat gtatccgctc atgagacaat aaccctgata   3360
aatgcttcaa taatattgaa aaaggaagag tatgagtatt caacatttcc gtgtcgccct   3420
tattcccttt tttgcggcat tttgccttcc tgtttttgct cacccagaaa cgctggtgaa   3480
agtaaaagat gctgaagatc agttgggtgc acgagtgggt tacatcgaac tggatctcaa   3540
cagcggtaag atccttgaga gttttcgccc cgaagaacgt tttccaatga tgagcacttt   3600
taaagttctg ctatgtggcg cggtattatc ccgtgttgac gccgggcaag agcaactcgg   3660
tcgccgcata cactattctc agaatgactt ggttgagtac tcaccagtca cagaaaagca   3720
tcttacggat ggcatgacag taagagaatt atgcagtgct gccataacca tgagtgataa   3780
cactgcggcc aacttacttc tgacaacgat cggaggaccg aaggagctaa ccgcttttttt   3840 gcacaacatg gggatcatg taactcgcct tgatcgttgg gaaccggagc tgaatgaagc   3900
cataccaaac gacgagcgtg acaccacgat gcctacagca atggcaacaa cgttgcgcaa   3960
actattaact ggcgaactac ttactctagc ttcccggcaa caattaatag actggatgga   4020
ggcggataaa gttgcaggac cacttctgcg ctcggccctt ccggctggct ggtttattgc   4080
tgataaatct ggagccggtg agcgtgggtc tcgcggtatc attgcagcac tggggccaga   4140
tggtaagccc tcccgtatcg tagttatcta cacgacgggg agtcaggcaa ctatggatga   4200
acgaaataga cagatcgctg agataggtgc ctcactgatt aagcattggt aactgtcaga   4260
ccaagtttac tcatatatac tttagattga tttaaaactt catttttaat ttaaaaggat   4320
ctaggtgaag atcctttttg ataatctcat gaccaaaatc ccttaacgtg agttttcgtt   4380
ccactgagcg tcagaccccg tagaaaagat caaaggatct tcttgagatc cttttttttct   4440 gcgcgtaatc tgctgcttgc aaacaaaaaa accaccgcta ccagcggtgg tttgtttgcc   4500
ggatcaagag ctaccaactc ttttccgaa ggtaactggc ttcagcagag cgcagatacc   4560
aaatactgtc cttctagtgt agccgtagtt aggccaccac ttcaagaact ctgtagcacc   4620
gcctacatac ctcgctctgc taatcctgtt accagtggct gctgccagtg gcgataagtc   4680
gtgtcttacc gggttggact caagacgata gttaccggat aaggcgcagc ggtcgggctg   4740
aacggggggt tcgtgcacac agcccagctt ggagcgaacg acctacaccg aactgagata   4800
cctacagcgt gagctatgag aaagcgccac gcttcccgaa gggagaaagg cggacaggta   4860
tccggtaagc ggcagggtcg aacaggaga gcgcacgagg gagcttccag ggggaaacgc   4920
ctggtatctt tatagtcctg tcgggtttcg ccacctctga cttgagcgtc gatttttgtg   4980
atgctcgtca ggggggcgga gcctatggaa aaacgccagc aacgcggcct ttttacggtt   5040
cctggccttt tgctggcctt ttgctcacat gttctttcct gcgttatccc ctgattctgt   5100
ggataaccgt attaccgcct ttgagtgagc tgataccgct cgccgcagcc gaacgaccga   5160
gcgcagcgag tcagtgagcg aggaagcgga agagcgcctg atgcggtatt ttctccttac   5220
gcatctgtgc ggtatttcac accgcatatg                                    5250
```

<210> SEQ ID NO 11
<211> LENGTH: 39
<212> TYPE: DNA
<213> ORGANISM: Artificial Sequence
<220> FEATURE:
<223> OTHER INFORMATION: paratyphi A NcoI_F1

<400> SEQUENCE: 11
tacgccatgg tcaaaaaacc tgttttttttc cttctgacc                           39

<210> SEQ ID NO 12
<211> LENGTH: 43
<212> TYPE: DNA
<213> ORGANISM: Artificial Sequence
<220> FEATURE:
<223> OTHER INFORMATION: PCR primer HindIII_XbaI ClaI-R1

<400> SEQUENCE: 12
cgatccctct agacccaagc ttgtcactga tattagcgca ggc              43

<210> SEQ ID NO 13
<211> LENGTH: 49
<212> TYPE: DNA
<213> ORGANISM: Artificial Sequence
<220> FEATURE:
<223> OTHER INFORMATION: PCR primer HindIII_XbaI_ClaI-F1

<400> SEQUENCE: 13
gcttgggtct agagggatcg attacaaagt tatgacctgg aatcttcag        49

<210> SEQ ID NO 14
<211> LENGTH: 39
<212> TYPE: DNA
<213> ORGANISM: Artificial Sequence
<220> FEATURE:
<223> OTHER INFORMATION: PCR primer cldtB_stop_XbaI_SalI-R1

<400> SEQUENCE: 14
gatcgtcgac ttatctagat cattaacagc ttcgtgcca                   39

<210> SEQ ID NO 15
<211> LENGTH: 4794
<212> TYPE: DNA
<213> ORGANISM: Artificial Sequence
<220> FEATURE:
<223> OTHER INFORMATION: 13-350 = arabinose promoter; 351-1187 = cldtB;
      1210-1213 =RBS pltB; 1221-1634 = pltB; 1651-2379 = pltA

<400> SEQUENCE: 15
gggggcggcc gcaagaaacc aattgtccat attgcatcag acattgccgt cactgcgtct    60
tttactggct cttctcgcta accaaaccgg taaccccgct tattaaaagc attctgtaac   120
aaagcgggac caaagccatg acaaaaacgc gtaacaaaag tgtctataat cacggcagaa   180
aagtccacat tgattatttg cacggcgtca cactttgcta tgccatagca ttttatcca   240 taagattagc ggatcctacc tgacgctttt tatcgcaact ctctactgtt tctccatacc   300 cgttttttg ggctagcgaa ttcgagctcg gtacccagga ggaattcacc atggtcaaaa   360
aacctgtttt tttccttctg accatgatca tctgcagcta tatttctttt gcctgcgcta   420
atatcagtga caagcttggg tctagaggga tcgattacaa agttatgacc tggaatcttc   480
agggctcttc agcatctaca gaaagtaaat ggaatgtcaa tgtcagacag cttttaagcg   540
gtactgccgg tgtggatatt cttatggtac aggaggccgg tgctgttccc acctcagcgg   600
ttcctaccgg acgacatatt cagccttttg gagtgggtat tcccattgat gaatacacct   660
ggaatctcgg aaccaccagc cgtcaggata aagatatat ctactactcg gctattgatg   720
ttggagcacg ccgtgttaat ctggcaatag tttccagaca aagagcggat aatgtttatg   780
tcttgcgtcc gacaactgtc gcatctcgcc ccgtcattgg catcggactg ggtaatgatg   840
tttttctgac agcgcacgca ctggctagtg gaggtccgga tgctgcagct attgtcaggg   900
ttaccattaa ttttttaga caacctcaga tgcggcattt atcctggttt cttgccgggg   960

```
atttaatcg cagcccagac agacttgaaa atgacctgat gactgagcat ctggaacgag    1020
ttgtagccgt actcgcacct acagaaccca cgcaaattag cggtggtatt ttagattatg    1080
gggtcattgt cgatcgagca ccttattcac aaagggtcga agcattacgt aatccacaac    1140
tcgcttctga tcattatccc gtagccttt tggcacgaag ctgttaatga tctagataag    1200
tcgacgtaca ggagagtagt atgtatataa ataagtttgt gcctgtttat acattattaa    1260
ttctcattta ttcttttaat gccagcgctg agtggacagg agataatacg aacgcctatt    1320
actcagacga agttatcagt gaattacatg ttggtcagat agatactagt ccttattttt    1380
gcataaaaac ggtaaagct aacggtagtg gtacaccagt tgttgcatgt gcggtatcaa    1440
agcagagcat atgggcgccc tcctttaaag aacttcttga tcaggcaaga tatttttaca    1500
gtacagggca atccgtaagg attcatgttc aaaaaaatat ctggacctat ccgctttttg    1560 ttaataccctt ttcagcaaat gctcttgtgg gactatcatc gtgcagtgcg acacaatgct    1620
ttggacccaa gtaagagggg agaagaaata atgaaaagt taatattctt aaccttatct    1680
atagttagct ttaataacta tgctgtagat tttgtgtatc gtgtggactc aaccccgccg    1740
gacgttattt tcgcgatgg gttttcacta cttgggtata accgtaactt tcagcaattt    1800
attagtggaa ggtcatgtag tggtggaagt agtgacagtc gctatattgc aacaacctca    1860
agtgttaatc aaacatatgc tatagccaga gcgtactatt ctcgctcaac attcaaaggt    1920
aatttataca gatatcagat tcgtgcagat aataatttct acagcttgct cccatccatc    1980
acctatctgg aaacgcaagg tggtcacttt aatgcttatg aaaaaacgat gatgcgattg    2040
caaagagagt atgtttccac attatctatt ttacccgaga atattcaaaa ggccgtggcg    2100
ctagtttatg atagcgcaac cggtctggta aaggatggtg taagcacaat gaatgccagt    2160
tatttaggtt taagcactac gtctaatcct ggtgtgatac cttttcttcc ggaaccgcag    2220 acgtatacccc aacaacgaat tgatgcattc ggcccattaa taagttcatg cttttcaata    2280
ggtagcgtat gtcagtcaca tcgagggcaa agagctgacg tatacaacat gtctttttat    2340
gatgcaagac ctgtaataga acttatactt tctaaataaa tgaaacttac ctatgttgcc    2400
gcatgcaagc tagcttggct gttttggcgg atgagagaag attttcagcc tgatacagat    2460
taaatcagaa cgcagaagcg gtctgataaa acagaatttg cctggcggca gtagcgcggt    2520
ggtcccacct gaccccatgc cgaactcaga agtgaaacgc cgtagcgccg atggtagtgt    2580
ggggtctccc catgcgagag tagggaactg ccaggcatca aataaaacga aaggctcagt    2640
cgaaagactg ggcctttcgt tttatctgtt gtttgtcggt gaacgctctc ctgagtagga    2700
caaatccgcc gggagcggat ttgaacgttg cgaagcaacg gcccggaggg tggcgggcag    2760
gacgcccgcc ataaactgcc aggcatcaaa ttaagcagaa ggccatcctg acggatggcc    2820 ttttgcgtt tctacaaact ctttttgttt attttctaa atacattcaa atatgtatcc    2880
gctcatgaga caataaccct gataaatgct tcaataatat tgaaaagga agagtatgag    2940 tattcaacat ttccgtgtcg cccttattcc cttttttgcg gcattttgcc ttcctgtttt    3000
tgctcaccca gaaacgctgg tgaaagtaaa agatgctgaa gatcagttgg gtgcacgagt    3060
gggttacatc gaactggatc tcaacagcgg taagatcctt gagagttttc gccccgaaga    3120
acgttttcca atgatgagca cttttaaagt tctgctatgt ggcgcggtat tatcccgtgt    3180
tgacgccggg caagagcaac tcggtcgccg catacactat tctcagaatg acttggttga    3240
gtactcacca gtcacagaaa agcatcttac ggatggcatg acagtaagag aattatgcag    3300
```

```
tgctgccata accatgagtg ataacactgc ggccaactta cttctgacaa cgatcggagg    3360
accgaaggag ctaaccgctt ttttgcacaa catgggggat catgtaactc gccttgatcg    3420
ttgggaaccg gagctgaatg aagccatacc aaacgacgag cgtgacacca cgatgcctac    3480
agcaatggca acaacgttgc gcaaactatt aactggcgaa ctacttactc tagcttcccg    3540
gcaacaatta atagactgga tggaggcgga taaagttgca ggaccacttc tgcgctcggc    3600
ccttccggct ggctggttta ttgctgataa atctggagcc ggtgagcgtg ggtcgcgcgg    3660
tatcattgca gcactggggc cagatggtaa gccctcccgt atcgtagtta tctacacgac    3720
ggggagtcag gcaactatgg atgaacgaaa tagacagatc gctgagatag gtgcctcact    3780
gattaagcat tggtaactgt cagaccaagt ttactcatat atactttaga ttgatttaaa    3840
acttcatttt taatttaaaa ggatctaggt gaagatcctt tttgataatc tcatgaccaa    3900
aatcccttaa cgtgagtttt cgttccactg agcgtcagac cccgtagaaa agatcaaagg    3960
atcttcttga tccttttttt ttctgcgcgt aatctgctgc ttgcaaacaa aaaaaccacc    4020
gctaccagcg gtggtttgtt tgccggatca agagctacca actctttttc cgaaggtaac    4080
tggcttcagc agagcgcaga taccaaatac tgtccttcta gtgtagccgt agttaggcca    4140
ccacttcaag aactctgtag caccgcctac atacctcgct ctgctaatcc tgttaccagt    4200
ggctgctgcc agtggcgata agtcgtgtct taccggggttg gactcaagac gatagttacc    4260
ggataaggcg cagcggtcgg gctgaacggg gggttcgtgc acacagccca gcttggagcg    4320
aacgacctac accgaactga gatacctaca gcgtgagcta tgagaaagcg ccacgcttcc    4380
cgaagggaga aaggcggaca ggtatccggt aagcggcagg gtcggaacag gagagcgcac    4440
gagggagctt ccagggggaa acgcctggta tctttatagt cctgtcgggt ttcgccacct    4500
ctgacttgag cgtcgatttt tgtgatgctc gtcaggggg cggagcctat ggaaaaacgc    4560
cagcaacgcg gcctttttac ggttcctggc cttttgctgg ccttttgctc acatgttctt    4620
tcctgcgtta tcccctgatt ctgtggataa ccgtattacc gcctttgagt gagctgatac    4680
cgctcgccgc agccgaacga ccgagcgcag cgagtcagtg agcgaggaag cggaagagcg    4740
cctgatgcgg tatttctcc ttacgcatct gtgcggtatt tcacaccgca tatg          4794
```

<210> SEQ ID NO 16
<211> LENGTH: 4902
<212> TYPE: DNA
<213> ORGANISM: Artificial Sequence
<220> FEATURE:
<223> OTHER INFORMATION: 13-350 = arabinose promoter; 351-1295 = cldtB;
        1318-1321 =RBS pltB; 1329-1742 = pltB; 1759-2487 = pltA

<400> SEQUENCE: 16

```
gggggcggcc gcaagaaacc aattgtccat attgcatcag acattgccgt cactgcgtct      60
tttactggct cttctcgcta accaaaccgg taaccccgct tattaaaagc attctgtaac     120
aaagcgggac caaagccatg acaaaaacgc gtaacaaaag tgtctataat cacggcagaa     180
aagtccacat tgattatttg cacggcgtca cactttgcta tgccatagca ttttttatcca    240 taagattagc ggatcctacc tgacgctttt tatcgcaact ctctactgtt tctccatacc     300 cgttttttttg ggctagcgaa ttcgagctcg gtacccagga ggaattcacc atggtcaaaa    360
aacctgtttt tttccttctg accatgatca tctgcagcta tatttctttt gcctgcgcta    420
atatcagtga caagcttggg tctagagact acaaagacca tgacggtgat tataaagatc    480
atgatatcga ctacaaagat gacgacgata aaggcggtgg cggatccggc ggtggcggtt    540
```

```
ctggcggtgg cggtagtatc gattacaaag ttatgacctg gaatcttcag ggctcttcag    600
catctacaga aagtaaatgg aatgtcaatg tcagacagct tttaagcggt actgccggtg    660
tggatattct tatggtacag gaggccggtg ctgttcccac ctcagcggtt cctaccggac    720
gacatattca gccttttgga gtgggtattc ccattgatga atacacctgg aatctcggaa    780
ccaccagccg tcaggatata agatatatct actactcggc tattgatgtt ggagcacgcc    840
gtgttaatct ggcaatagtt tccagacaaa gagcggataa tgtttatgtc ttgcgtccga    900
caactgtcgc atctcgcccc gtcattggca tcggactggg taatgatgtt tttctgacag    960
cgcacgcact ggctagtgga ggtccggatg ctgcagctat tgtcagggtt accattaatt   1020
tttttagaca acctcagatg cggcatttat cctggtttct tgccggggat tttaatcgca   1080
gcccagacag acttgaaaat gacctgatga ctgagcatct ggaacgagtt gtagccgtac   1140
tcgcacctac agaacccacg caaattagcg gtggtatttt agattatggg gtcattgtcg   1200
atcgagcacc ttattcacaa agggtcgaag cattacgtaa tccacaactc gcttctgatc   1260
attatcccgt agccttttgt gcacgaagct gttaatgatc tagataagtc gacgtacagg   1320
agagtagtat gtatataaat aagtttgtgc ctgtttatac attattaatt ctcatttatt   1380
cttttaatgc cagcgctgag tggacaggag ataatacgaa cgcctattac tcagacgaag   1440
ttatcagtga attacatgtt ggtcagatag atactagtcc ttattttgc ataaaaacgg    1500
ttaaagctaa cggtagtggt acaccagttg ttgcatgtgc ggtatcaaag cagagcatat   1560
gggcgccctc ctttaaagaa cttcttgatc aggcaagata tttttacagt acagggcaat   1620
ccgtaaggat tcatgttcaa aaaaatatct ggacctatcc gcttttttgtt aatacctttt  1680
cagcaaatgc tcttgtggga ctatcatcgt gcagtgcgac acaatgcttt ggacccaagt   1740
aagagggag aagaaataat gaaaaagtta atattcttaa ccttatctat agttagcttt    1800
aataactatg ctgtagattt tgtgtatcgt gtggactcaa ccccgccgga cgttattttt   1860
cgcgatgggt tttcactact tgggtataac cgtaactttc agcaatttat tagtggaagg   1920
tcatgtagtg gtggaagtag tgacagtcgc tatattgcaa caacctcaag tgttaatcaa   1980
acatatgcta tagccagagc gtactattct cgctcaacat tcaaaggtaa tttatacaga   2040
tatcagattc gtgcagataa taatttctac agcttgctcc catccatcac ctatctggaa   2100
acgcaaggtg gtcactttaa tgcttatgaa aaaacgatga tgcgattgca aagagagtat   2160
gtttccacat tatctatttt acccgagaat attcaaaagg ccgtggcgct agtttatgat   2220
agcgcaaccg gtctggtaaa ggatggtgta agcacaatga atgccagtta tttaggttta   2280
agcactacgt ctaatcctgg tgtgatacct tttcttccgg aaccgcagac gtatacccaa   2340
caacgaattg atgcattcgg cccattaata agttcatgct tttcaatagg tagcgtatgt   2400
cagtcacatc gagggcaaag agctgacgta tacaacatgt cttttttatga tgcaagacct  2460
gtaatagaac ttatactttc taaataaatg aaacttacct atgttgccgc atgcaagcta   2520
gcttggctgt tttggcggat gagagaagat tttcagcctg atacagatta aatcagaacg   2580
cagaagcggt ctgataaaac agaatttgcc tggcggcagt agcgcggtgg tcccacctga   2640
ccccatgccg aactcagaag tgaaacgccg tagcgccgat ggtagtgtgg ggtctcccca   2700
tgcgagagta gggaactgcc aggcatcaaa taaaacgaaa ggctcagtcg aaagactggg   2760
cctttcgttt tatctgttgt ttgtcggtga acgctctcct gagtaggaca atccgccgg    2820
gagcggattt gaacgttgcg aagcaacggc ccggagggtg cgggcagga cgcccgccat    2880
aaactgccag gcatcaaatt aagcagaagg ccatcctgac ggatggcctt tttgcgtttc   2940
```

| | |
|---|---|
| tacaaactct ttttgtttat ttttctaaat acattcaaat atgtatccgc tcatgagaca | 3000 |
| ataaccctga taaatgcttc aataatattg aaaaaggaag agtatgagta ttcaacattt | 3060 |
| ccgtgtcgcc cttattccct tttttgcggc attttgcctt cctgttttg ctcacccaga | 3120 |
| aacgctggtg aaagtaaaag atgctgaaga tcagttgggt gcacgagtgg gttacatcga | 3180 |
| actggatctc aacagcggta agatccttga gagttttcgc cccgaagaac gttttccaat | 3240 |
| gatgagcact tttaaagttc tgctatgtgg cgcggtatta tcccgtgttg acgccgggca | 3300 |
| agagcaactc ggtcgccgca tacactattc tcagaatgac ttggttgagt actcaccagt | 3360 |
| cacagaaaag catcttacgg atggcatgac agtaagagaa ttatgcagtg ctgccataac | 3420 |
| catgagtgat aacactgcgg ccaacttact tctgacaacg atcggaggac cgaaggagct | 3480 |
| aaccgctttt ttgcacaaca tgggggatca tgtaactcgc cttgatcgtt gggaaccgga | 3540 |
| gctgaatgaa gccataccaa acgacgagcg tgacaccacg atgcctacag caatggcaac | 3600 |
| aacgttgcgc aaactattaa ctggcgaact acttactcta gcttcccggc aacaattaat | 3660 |
| agactggatg gaggcggata agttgcagg accacttctg cgctcggccc ttccggctgg | 3720 |
| ctggtttatt gctgataaat ctggagccgg tgagcgtggg tctcgcggta tcattgcagc | 3780 |
| actggggcca gatggtaagc cctcccgtat cgtagttatc tacacgacgg ggagtcaggc | 3840 |
| aactatggat gaacgaaata gacagatcgc tgagataggt gcctcactga ttaagcattg | 3900 |
| gtaactgtca gaccaagttt actcatatat actttagatt gatttaaaac ttcatttta | 3960 |
| atttaaaagg atctaggtga agatcctttt tgataatctc atgaccaaaa tcccttaacg | 4020 |
| tgagttttcg ttccactgag cgtcagaccc cgtagaaaag atcaaaggat cttcttgaga | 4080 |
| tccttttttt ctgcgcgtaa tctgctgctt gcaaacaaaa aaaccaccgc taccagcggt | 4140 |
| ggtttgtttg ccggatcaag agctaccaac tcttttccg aaggtaactg gcttcagcag | 4200 |
| agcgcagata ccaaatactg tccttctagt gtagccgtag ttaggccacc acttcaagaa | 4260 |
| ctctgtagca ccgcctacat acctcgctct gctaatcctg ttaccagtgg ctgctgccag | 4320 |
| tggcgataag tcgtgtctta ccgggttgga ctcaagacga tagttaccgg ataaggcgca | 4380 |
| gcggtcgggc tgaacggggg gttcgtgcac acagcccagc ttggagcgaa cgacctacac | 4440 |
| cgaactgaga tacctacagc gtgagctatg agaaagcgcc acgcttcccg aagggagaaa | 4500 |
| ggcggacagg tatccggtaa gcggcagggt cggaacagga gagcgcacga gggagcttcc | 4560 |
| agggggaaac gcctggtatc tttatagtcc tgtcgggttt cgccacctct gacttgagcg | 4620 |
| tcgatttttg tgatgctcgt caggggggcg gagcctatgg aaaaacgcca gcaacgcggc | 4680 |
| cttttacgg ttcctggcct tttgctggcc ttttgctcac atgttctttc ctgcgttatc | 4740 |
| ccctgattct gtggataacc gtattaccgc ctttgagtga gctgataccg ctcgccgcag | 4800 |
| ccgaacgacc gagcgcagcg agtcagtgag cgaggaagcg gaagagcgcc tgatgcggta | 4860 |
| ttttctcctt acgcatctgt gcggtatttc acaccgcata tg | 4902 |

<210> SEQ ID NO 17
<211> LENGTH: 3560
<212> TYPE: DNA
<213> ORGANISM: Artificial Sequence
<220> FEATURE:
<223> OTHER INFORMATION: tetracyclin-inducible YebF:SFTI, start codon
      begins at 724 and the stop codon ends at 1158

<400> SEQUENCE: 17

| | |
|---|---|
| atatggggc ggccgcctaa gacccacttt cacatttaag ttgttttct aatccgcata | 60 |

```
taatcaattc aaggccgaat aagaaggctg gctctgcacc ttggtgttca aataattcga    120
tagcttgtcg taataatgcc ggcatactat cagtagtagg tgtttccctt tcttcttag    180 cgacttgatg ctcttgatct tccaatacgc aacctaaagt aaaatgcccc acagcgctga    240
gtgcatataa tgcattctct agtgaaaaac cttgttggca taaaaggct aattgatttt     300 cgagagtttc atactgtttt tctgtaggcc gtgtacctaa atgtacttt gctccatcgc     360 gatgacttag taaagcacat ctaaaacttt tagcgttatt acgtaaaaaa tcttgccagc    420 tttcccttc taaagggcaa aagtgagtat ggtgcctatc taacatctca atggctaagg     480
cgtcgagcaa agcccgctta ttttttacat gccaatacaa tgtaggctgc tctacaccca    540
gtttctgggc gagtttacgg gttttaaaac cttcgattcc gacctcatta agcagctcta    600
atgcgctgtt aatcactta cttttatcta atctggacat cataaattcc taatttttgt     660
tgacactcta tcattgatag agttatttta ccactcccta tcagtgatag agaaaagtga    720
accatggcta aaaaagagg ggcgtttta gggctgttgt tggtttctgc ctgcgcatca      780
gttttcgctg ccaataatga aaccagcaag tcggtcactt tcccaaagtg tgaagatctg    840
gatgctgccg gaattccgc gagcgtaaaa cgtgattatc aacaaaatcg cgtggcgcgt     900
tgggcagatg atcaaaaaat tgtcggtcag gccgatcccg tggcttgggt cagtttgcag    960
gacattcagg gtaaagatga taatggtca gtaccgctaa ccgtgcgtgg taaaagtgcc     1020
gatattcatt accaggtcag cgtggactgc aaagcgggaa tggcggaata tcagcggcgt    1080
ctcgaggacg atgacgataa gggtaccctg aaaggccgct gcaccaaaag cattccgccg    1140
atttgctttc cggattagtc tagagtcgac ctgcaggcat gcaagcttgg ctgttttggc    1200
ggatgagaga agattttcag cctgatacag attaaatcag aacgcagaag cggtctgata    1260
aaacagaatt tgcctggcgg cagtagcgcg gtggtcccac ctgaccccat gccgaactca    1320
gaagtgaaac gccgtagcgc cgatggtagt gtggggtctc cccatgcgag agtagggaac    1380
tgccaggcat caaataaaac gaaaggctca gtcgaaagac tgggcctttc gttttatctg    1440
ttgtttgtcg gtgaacgctc tcctgagtag acaaatccg ccgggagcgg atttgaacgt     1500
tgcgaagcaa cggcccggag ggtggcgggc aggacgcccg ccataaactg ccaggcatca    1560
aattaagcag aaggccatcc tgacggatgg ccttttgcg tttctacaaa ctcttttgt      1620 ttattttct aaatacattc aaatatgtat ccgctcatga acaataacc ctgataaatg      1680 cttcaataat attgaaaaag gaagagtatg agtattcaac atttccgtgt cgcccttatt    1740 ccctttttg cggcattttg ccttcctgtt tttgctcacc cagaaacgct ggtgaaagta     1800
aaagatgctg aagatcagtt gggtgcacga gtgggttaca tcgaactgga tctcaacagc    1860
ggtaagatcc ttgagagttt tcgccccgaa gaacgttttc caatgatgag cacttttaaa    1920
gttctgctat gtggcgcggt attatcccgt gttgacgccg ggcaagagca actcggtcgc    1980
cgcatacact attctcagaa tgacttggtt gagtactcac cagtcacaga aaagcatctt    2040
acggatggca tgacagtaag agaattatgc agtgctgcca taaccatgag tgataacact    2100
gcggccaact tacttctgac aacgatcgga ggaccgaagg agctaaccgc ttttttgcac    2160
aacatggggg atcatgtaac tcgccttgat cgttgggaac cggagctgaa tgaagccata    2220
ccaaacgacg agcgtgacac cacgatgcct acagcaatgg caacaacgtt gcgcaaacta    2280
ttaactggcg aactacttac tctagcttcc cggcaacaat taatagactg gatgaggcg     2340 gataaagttg caggaccact tctgcgctcg gcccttccgg ctggctggtt tattgctgat    2400
```

```
aaatctggag ccggtgagcg tgggtctcgc ggtatcattg cagcactggg gccagatggt    2460
aagccctccc gtatcgtagt tatctacacg acggggagtc aggcaactat ggatgaacga    2520
aatagacaga tcgctgagat aggtgcctca ctgattaagc attggtaact gtcagaccaa    2580
gtttactcat atatacttta gattgattta aacttcatt tttaatttaa aaggatctag     2640
gtgaagatcc ttttttgataa tctcatgacc aaaatccctt aacgtgagtt ttcgttccac   2700
tgagcgtcag accccgtaga aaagatcaaa ggatcttctt gagatccttt ttttctgcgc    2760
gtaatctgct gcttgcaaac aaaaaaacca ccgctaccag cggtggtttg tttgccggat    2820
caagagctac caactctttt tccgaaggta actggcttca gcagagcgca gataccaaat    2880
actgtccttc tagtgtagcc gtagttaggc caccacttca agaactctgt agcaccgcct    2940
acatacctcg ctctgctaat cctgttacca gtggctgctg ccagtggcga taagtcgtgt    3000
cttaccgggt tggactcaag acgatagtta ccggataagg cgcagcggtc gggctgaacg    3060
gggggttcgt gcacacagcc cagcttggag cgaacgacct acaccgaact gagataccta    3120
cagcgtgagc tatgagaaag cgccacgctt cccgaaggga aaaggcgga caggtatccg    3180 gtaagcggca gggtcggaac aggagagcgc acgagggagc ttccagggggg aaacgcctgg   3240 tatctttata gtcctgtcgg gtttcgccac ctctgacttg agcgtcgatt tttgtgatgc    3300
tcgtcagggg gcggagcct atggaaaaac gccagcaacg cggcctttttt acggttcctg    3360 gccttttgct ggccttttgc tcacatgttc tttcctgcgt tatcccctga ttctgtggat    3420
aaccgtatta ccgcctttga gtgagctgat accgctcgcc gcagccgaac gaccgagcgc    3480
agcgagtcag tgagcgagga agcggaagag cgcctgatgc ggtattttct ccttacgcat    3540
ctgtgcggta tttcacaccg                                                3560
```

<210> SEQ ID NO 18
<211> LENGTH: 3249
<212> TYPE: DNA
<213> ORGANISM: Artificial Sequence
<220> FEATURE:
<223> OTHER INFORMATION: tetracycline inducible OmpA:SFTI fusion, start
      codon begins at 725 and stop codon ends at 1008

<400> SEQUENCE: 18

```
catatggggg cggccgccta agacccactt tcacatttaa gttgttttc taatccgcat     60 ataatcaatt caaggccgaa taagaaggct ggctctgcac cttggtgttc aaataattcg    120
atagcttgtc gtaataatgc cggcatacta tcagtagtag gtgtttccct ttcttcttta    180
gcgacttgat gctcttgatc ttccaatacg caacctaaag taaatgccc cacagcgctg    240 agtgcatata atgcattctc tagtgaaaaa ccttgttggc ataaaaaggc taattgattt    300
tcgagagttt catactgttt ttctgtaggc cgtgtaccta aatgtacttt tgctccatcg    360
cgatgactta gtaaagcaca tctaaaactt ttagcgttat tacgtaaaaa atcttgccag    420
ctttcccctt ctaaagggca aaagtgagta tggtgcctat ctaacatctc aatggctaag    480
gcgtcgagca aagcccgctt atttttaca tgccaataca atgtaggctg ctctacaccc    540
agtttctggg cgagtttacg ggtttttaaa ccttcgattc cgacctcatt aagcagctct    600
aatgcgctgt taatcacttt actttatct aatctggaca tcataaattc ctaatttttg    660
ttgacactct atcattgata gagttatttt accactccct atcagtgata gagaaaagtg    720
aaccatggct aaaaagacag ctatcgcgat tgcagtggca ctggctggtt tcgctaccgt    780
agcgcaggcc gctccgaaag atggccgctg caccaaaagc attccgccga tttgctttcc    840
```

```
ggattagtct agagtcgacc tgcaggcatg caagcttggc tgttttggcg gatgagagaa      900
gattttcagc ctgatacaga ttaaatcaga acgcagaagc ggtctgataa aacagaattt      960
gcctggcggc agtagcgcgg tggtcccacc tgaccccatg ccgaactcag aagtgaaacg     1020
ccgtagcgcc gatggtagtg tggggtctcc ccatgcgaga gtagggaact gccaggcatc     1080
aaataaaacg aaaggctcag tcgaaagact gggcctttcg ttttatctgt tgtttgtcgg     1140
tgaacgctct cctgagtagg acaaatccgc cgggagcgga tttgaacgtt gcgaagcaac     1200
ggcccggagg gtggcgggca ggacgcccgc cataaactgc caggcatcaa attaagcaga     1260
aggccatcct gacggatggc cttttttgcgt tctacaaac tcttttttgtt tattttttcta     1320
aatacattca aatatgtatc cgctcatgag acaataaccc tgataaatgc ttcaataata     1380
ttgaaaaagg aagagtatga gtattcaaca tttccgtgtc gcccttattc ccttttttgc      1440
ggcatttttgc cttcctgttt ttgctcaccc agaaacgctg gtgaaagtaa aagatgctga     1500
agatcagttg ggtgcacgag tgggttacat cgaactggat ctcaacagcg gtaagatcct     1560
tgagagtttt cgccccgaag aacgttttcc aatgatgagc acttttaaag ttctgctatg     1620
tggcgcggta ttatcccgtg ttgacgccgg gcaagagcaa ctcggtcgcc gcatacacta     1680
ttctcagaat gacttggttg agtactcacc agtcacagaa aagcatctta cggatggcat     1740
gacagtaaga gaattatgca gtgctgccat aaccatgagt gataacactg cggccaactt     1800
acttctgaca acgatcggag gaccgaagga gctaaccgct tttttgcaca acatggggga     1860
tcatgtaact cgccttgatc gttgggaacc ggagctgaat gaagccatac caaacgacga     1920
gcgtgacacc acgatgccta gcaatggca acaacgttg cgcaaactat taactggcga     1980
actacttact ctagcttccc ggcaacaatt aatagactgg atggaggcgg ataaagttgc     2040
aggaccactt ctgcgctcgg cccttccggc tggctggttt attgctgata aatctggagc     2100
cggtgagcgt gggtctcgcg gtatcattgc agcactgggg ccagatggta agccctcccg     2160
tatcgtagtt atctacacga cggggagtca ggcaactatg gatgaacgaa atagacagat     2220
cgctgagata ggtgcctcac tgattaagca ttggtaactg tcagaccaag tttactcata     2280
tatactttag attgatttaa aacttcattt ttaatttaaa aggatctagg tgaagatcct     2340
ttttgataat ctcatgacca aaatccctta acgtgagttt tcgttccact gagcgtcaga     2400
ccccgtagaa aagatcaaag gatcttcttg agatcctttt tttctgcgcg taatctgctg     2460
cttgcaaaca aaaaaaccac cgctaccagc ggtggtttgt ttgccggatc aagagctacc     2520
aactcttttt ccgaaggtaa ctggcttcag cagagcgcag ataccaaata ctgtccttct     2580
agtgtagccg tagttaggcc accacttcaa gaactctgta gcaccgccta catacctcgc     2640
tctgctaatc ctgttaccag tggctgctgc cagtggcgat aagtcgtgtc ttaccgggtt     2700
ggactcaaga cgatagttac cggataaggc gcagcggtcg ggctgaacgg ggggttcgtg     2760
cacacagccc agcttggagc gaacgaccta caccgaactg agatacctac agcgtgagct     2820
atgagaaagc gccacgcttc ccgaagggag aaaggcggac aggtatccgg taagcggcag     2880
ggtcggaaca ggagagcgca cgagggagct tccagggga aacgcctggt atctttatag     2940
tcctgtcggg tttcgccacc tctgacttga gcgtcgattt ttgtgatgct cgtcaggggg     3000
gcggagccta tggaaaaacg ccagcaacgc ggccttttta cggttcctgg ccttttgctg     3060
gccttttgct cacatgttct ttcctgcgtt atcccctgat tctgtggata accgtattac     3120
cgcctttgag tgagctgata ccgctcgccg cagccgaacg accgagcgca gcgagtcagt     3180
gagcgaggaa gcggaagagc gcctgatgcg gtattttctc cttacgcatc tgtgcggtat     3240
```

<210> SEQ ID NO 19
<211> LENGTH: 3398
<212> TYPE: DNA
<213> ORGANISM: Artificial Sequence
<220> FEATURE:
<223> OTHER INFORMATION: tetracycline inducible OmpA:SFTI fusion, start codon at 725, stop codon at 1008, followed by a Shine Delgarno sequence (RBS) and coding sequence for E3 Lysis sequence, start codon at 865, stop codon at 1008

<400> SEQUENCE: 19

```
catatggggg cggccgccta agacccactt tcacatttaa gttgttttc taatccgcat      60
ataatcaatt caaggccgaa taagaaggct ggctctgcac cttggtgttc aaataattcg     120
atagcttgtc gtaataatgc cggcatacta tcagtagtag gtgtttccct ttcttcttta    180
gcgacttgat gctcttgatc ttccaatacg caacctaaag taaaatgccc cacagcgctg    240
agtgcatata atgcattctc tagtgaaaaa ccttgttggc ataaaaaggc taattgattt    300
tcgagagttt catactgttt ttctgtaggc cgtgtaccta aatgtacttt tgctccatcg    360
cgatgactta gtaaagcaca tctaaaactt ttagcgttat tacgtaaaaa atcttgccag    420
ctttccccctt ctaaagggca aaagtgagta tggtgcctat ctaacatctc aatggctaag    480
gcgtcgagca aagcccgctt attttttaca tgccaataca atgtaggctg ctctacaccc    540
agtttctggg cgagtttacg ggttttaaa ccttcgattc cgacctcatt aagcagctct    600
aatgcgctgt taatcacttt actttatct aatctggaca tcataaattc ctaattttg     660
ttgacactct atcattgata gagttatttt accactccct atcagtgata gagaaaagtg    720
aaccatggct aaaaagacag ctatcgcgat tgcagtggca ctggctggtt tcgctaccgt    780
agcgcaggcc gctccgaaag atggccgctg caccaaaagc attccgccga tttgctttcc    840
ggattagtct agaaaggagt cgttatgaaa aaaataacag gattatttt attgcttctt    900
gcagtcatta ttctgtctgc atgtcaggca aactatatcc gggatgttca gggcgggacc    960
gtatctccgt catcaacagc tgaagtgacc ggattagcaa cgcagtaact gcaggcatgc   1020
aagcttggct gttttggcgg atgagagaag attttcagcc tgatacagat taaatcagaa   1080
cgcagaagcg gtctgataaa acagaatttg cctggcggca gtagcgcggt ggtcccacct   1140
gaccccatgc cgaactcaga agtgaaacgc cgtagcgccg atggtagtgt ggggtctccc   1200
catgcgagag tagggaactg ccaggcatca aataaaacga aggctcagtc gaaagactg    1260
ggccttccgt tttatctgtt gtttgtcggt gaacgctctc ctgagtagga caaatccgcc   1320
gggagcggat ttgaacgttg cgaagcaacg gcccggaggg tggcgggcag gacgcccgcc   1380
ataaactgcc aggcatcaaa ttaagcagaa ggccatcctg acggatggcc ttttttgcgt   1440
tctacaaact cttttttgttt atttttctaa atacattcaa atatgtatcc gctcatgaga   1500
caataaccct gataaatgct tcaataatat tgaaaaagga agagtatgag tattcaacat   1560
ttccgtgtcg cccttattcc cttttttgcg gcattttgcc ttcctgtttt tgctcaccca   1620
gaaacgctgg tgaaagtaaa agatgctgaa gatcagttgg gtgcacgagt gggttacatc   1680
gaactggatc tcaacagcgg taagatcctt gagagttttc gccccgaaga acgttttcca   1740
atgatgagca cttttaaagt tctgctatgt ggcgcggtat tatcccgtgt tgacgccggg   1800
caagagcaac tcggtcgccg catacactat tctcagaatg acttggttga gtactcacca   1860
gtcacagaaa agcatcttac ggatggcatg acagtaagag aattatgcag tgctgccata   1920
```

```
accatgagtg ataacactgc ggccaactta cttctgacaa cgatcggagg accgaaggag    1980
ctaaccgctt ttttgcacaa catgggggat catgtaactc gccttgatcg ttgggaaccg    2040
gagctgaatg aagccatacc aaacgacgag cgtgacacca cgatgcctac agcaatggca    2100
acaacgttgc gcaaactatt aactggcgaa ctacttactc tagcttcccg gcaacaatta    2160
atagactgga tggaggcgga taaagttgca ggaccacttc tgcgctcggc ccttccggct    2220
ggctggttta ttgctgataa atctggagcc ggtgagcgtg gtctcgcgg tatcattgca     2280
gcactggggc cagatggtaa gccctcccgt atcgtagtta tctacacgac ggggagtcag    2340
gcaactatgg atgaacgaaa tagacagatc gctgagatag gtgcctcact gattaagcat    2400
tggtaactgt cagaccaagt ttactcatat atactttaga ttgatttaaa acttcatttt    2460
taatttaaaa ggatctaggt gaagatcctt tttgataatc tcatgaccaa aatcccttaa    2520
cgtgagtttt cgttccactg agcgtcagac cccgtagaaa agatcaaagg atcttcttga    2580
gatcctttttt tctgcgcgt aatctgctgc ttgcaaacaa aaaaaccacc gctaccagcg    2640
gtggtttgtt tgccggatca agagctacca actcttttttc cgaaggtaac tggcttcagc    2700
agagcgcaga taccaaatac tgtccttcta gtgtagccgt agttaggcca ccacttcaag    2760
aactctgtag caccgcctac atacctcgct ctgctaatcc tgttaccagt ggctgctgcc    2820
agtggcgata gtcgtgtct taccggggttg gactcaagac gatagttacc ggataaggcg    2880
cagcggtcgg gctgaacggg gggttcgtgc acacagccca gcttggagcg aacgacctac    2940
accgaactga gatacctaca gcgtgagcta tgagaaagcg ccacgcttcc cgaagggaga    3000
aaggcggaca ggtatccggt aagcggcagg gtcggaacag gagagcgcac gagggagctt    3060
ccagggggaa acgcctggta tctttatagt cctgtcgggt ttcgccacct ctgacttgag    3120
cgtcgatttt tgtgatgctc gtcagggggg cggagcctat ggaaaaacgc cagcaacgcg    3180
gcctttttac ggttcctggc cttttgctgg ccttttgctc acatgttctt tcctgcgtta    3240
tcccctgatt ctgtggataa ccgtattacc gcctttgagt gagctgatac cgctcgccgc    3300
agccgaacga ccgagcgcag cgagtcagtg agcgaggaag cggaagagcg cctgatgcgg    3360
tatttttctcc ttacgcatct gtgcggtatt tcacaccg                           3398
```

<210> SEQ ID NO 20
<211> LENGTH: 11
<212> TYPE: PRT
<213> ORGANISM: Artificial Sequence
<220> FEATURE:
<223> OTHER INFORMATION: HIV TAT protein amino acids 47-57

<400> SEQUENCE: 20

Tyr Gly Arg Lys Lys Arg Arg Gln Arg Arg Arg
1               5                   10

<210> SEQ ID NO 21
<211> LENGTH: 9
<212> TYPE: PRT
<213> ORGANISM: Artificial Sequence
<220> FEATURE:
<223> OTHER INFORMATION: lymphoid tissue targeting peptide

<400> SEQUENCE: 21

Cys Ala Tyr His Arg Leu Arg Arg Cys
1               5

<210> SEQ ID NO 22

```
<211> LENGTH: 12
<212> TYPE: PRT
<213> ORGANISM: Artificial Sequence
<220> FEATURE:
<223> OTHER INFORMATION: Peptide from Clostridium

<400> SEQUENCE: 22

Cys Gln Thr Ile Asp Gly Lys Lys Tyr Tyr Phe Asn
1               5                   10

<210> SEQ ID NO 23
<211> LENGTH: 5
<212> TYPE: PRT
<213> ORGANISM: Artificial Sequence
<220> FEATURE:
<223> OTHER INFORMATION: native C-terminal signal of ToxA sequence

<400> SEQUENCE: 23

Arg Glu Asp Leu Lys
1               5
```

CHIMERIC PROTEIN TOXINS FOR EXPRESSION BY THERAPEUTIC BACTERIA

CROSS REFERENCE TO RELATED APPLICATIONS

The present application is a non-provisional of U.S. Provisional Patent Application 62/159,645, filed May 11, 2015, entitled "IMPROVED CHIMERIC PROTEIN TOXINS FOR EXPRESSION BY THERAPEUTIC BACTERIA", naming Dr. David Bermudes and Mr. David Quintero as inventors, the entirety of which is expressly incorporated herein by reference in its entirety.

STATEMENT OF GOVERNMENT RIGHTS

This invention was made with government support under 15C3GM098207 awarded by The National Institutes of Health. The government has certain rights in the invention.

BACKGROUND

Field of the Invention

This invention is generally in the field of therapeutic delivery systems including bacteria, and systems and methods for providing chimeric proteins efficiently targeted to cancer cells.

Description of the Prior Art

Citation or identification of any reference herein, or any section of this application shall not be construed as an admission that such reference is available as prior art to the present application. The disclosures of each of these publications and patents are hereby incorporated by reference in their entirety in this application, and shall be treated as if the entirety thereof forms a part of this application.

Tumor-targeted bacteria offer tremendous potential advantages for the treatment of solid tumors, including the targeting from a distant inoculation site and the ability to express therapeutic agents directly within the tumor (Pawelek et al., 1997, Tumor-targeted *Salmonella* as a novel anticancer agent, Cancer Research 57: 4537-4544; Low et al., 1999, Lipid A mutant *salmonella* with suppressed virulence and TNF-alpha induction retain tumor-targeting in vivo, Nature Biotechnol. 17: 37-41). However, the primary shortcoming of tumor-targeted bacteria investigated in the human clinical trials (*Salmonella* strain VNP20009 and its derivative TAPET-CD; Toso et al., 2002, Phase I study of the intravenous administration of attenuated *Salmonella typhimurium* to patients with metastatic melanoma, J. Clin, Oncol. 20: 142-152; Meir et al., 2001, Phase 1 trial of a live, attenuated *Salmonella typhimurium* (VNP20009) administered by direct Intra-tumoral (IT) injection, Proc Am Soc Clin Oncol 20: abstr 1043); Nemunaitis et al., 2003, Pilot trial of genetically modified, attenuated *Salmonella* expressing the *E. coli* cytosine deaminase gene in refractory cancer patients, Cancer Gene Therapy 10: 737-744) is that no significant antitumor activity has been observed, even in patients where the bacteria was documented to target the tumor. One method of increasing the ability of the bacteria to kill tumor cells is to engineer the bacteria to express conventional bacterial toxins (e.g., WO 2009/126189, WO 03/014380, WO/2005/018332, WO/2008/073148, US 2003/0059400 U.S. Pat. Nos. 7,452,531, 7,354,592, 6,962,696, 6,923,972, 6,863,894, 6,685,935, 6,475,482, 6,447,784, 6,190,657 and 6,080,849, 8,241,623, 8,524,220 8,771,669, 8,524,220, each of which is expressly incorporated herein by reference).

Use of protein toxins for treatment of various disorders including inflammation, autoimmunity, neurological disorders and cancer has long-suffered from off-target toxicity. Enhancing toxin specificity, which offers the potential to eliminate side effect, has been achieved by several different means, such as attachment of a specific antibodies or peptide ligand (e.g., *Pseudomonas* exotoxin A (PE-ToxA) antibody conjugate, known as an immunotoxin), or a ligand targeted to a surface molecule of the target cell. Based upon the binding specificity of the attached antibody or ligand moiety for a specific target, enhanced specificity of the target is achieved.

Other toxins have been engineered to achieve specificity based upon their sight of activation. For example, proaerolysin requires proteolytic activation to become the cytotoxic protein aerolysin. Substitution of the natural protease cleavage site for a tumor-specific protease cleavage site (e.g., that of the prostate specific antigen (PSA) protease or urokinase) results in a toxin selectively activated within tumors (Denmeade et al. WO 03/018611 and Denmeade et al. U.S. Pat. No. 7,635,682), specifically incorporated by reference herein. Another similar activation system has utilized ubiquitin fusion, coupled with a hydrolysable tumor protease (e.g., PSA) sequence and a toxin (e.g., saporin), as described by Tschrniuk et al. 2005 (Construction of tumor-specific toxins using ubiquitin fusion technique, Molecular Therapy 11: 196-204), also specifically incorporated by reference herein. However, while some specificity is engendered and thus these activated protein types are useful in the present technology as modified herein, in these types of engineered toxins, off-target toxicity can occur. In the case of the *Pseudomonas* immunotoxin, several dose-limiting toxicities have been identified. Vascular leakage syndrome (VLS) is associated with hypoalbuminemia, edema, weight gain, hypotension and occasional dyspnea, which is suggested to occur by immunotoxin-mediated endothelial cell injury (Baluna et al., 2000, Exp. Cell Res. 258: 417-424), resulting in a dose-limiting toxicity. Renal injury has occurred in some patients treated with immunotoxins, which may be due to micro-aggregates of the immunotoxin (Frankel et al., 2001, Blood 98: 722a). Liver damage from immunotoxins is a frequent occurrence that is believed to be multifactorial (Frankel, 2002, Clinical Cancer Research 8: 942-944). To date, antibodies linked to proteinaceous toxins have limited success clinically.

Recently developed approaches to delivery of therapeutic molecules (U.S. Pat. Nos. 8,241,623; 8,524,220; 8,771,669; and 8,524,220) have coupled a protease sensitive therapeutic molecule with co-expression of protease inhibitors, expressly incorporated by reference herein.

Use of secreted proteins in live bacterial vectors has been demonstrated by several authors. Holland et al. (U.S. Pat. No. 5,143,830) have illustrated the use of fusions with the C-terminal portion of the hemolysin A (hlyA) gene, a member of the type I secretion system. When co-expressed in the presence of the hemolysin protein secretion channel (hlyBD) and a functional TolC, heterologous fusions are readily secreted from the bacteria. The type I secretion system that has been utilized most widely, and although it is currently considered the best system available, is thought to have limitations for delivery by attenuated bacteria (Hahn and Specht, 2003, FEMS Immunology and Medical Microbiology, 37: 87-98). Those limitations include the amount of protein secreted and the ability of the protein fused to it to interfere with secretion. Improvements of the type I secretion system have been demonstrated by Sugamata and Shiba (2005 Applied and Environmental Micobiology 71: 656-

662) using a modified hlyB, and by Gupta and Lee (2008 Biotechnology and Bioengineering, 101: 967-974) by addition of rare codons to the hlyA gene, each of which is expressly incorporated by reference in their entirety herein. Fusion to the gene ClyA (Galen et al., 2004, Infection and Immunity, 72: 7096-7106 and Type III secretion proteins have also been used. Surface display has been used to export proteins outside of the bacteria. For example, fusion of the Lpp protein amino acids 1-9 with the transmembrane region B3-B7 of OmpA has been used for surface display (Samuelson et al., 2002, Display of proteins on bacteria, J. Biotechnology 96: 129-154, expressly incorporated by reference in its entirety herein). The autotransporter surface display has been described by Berthet et al., WO/2002/070645, expressly incorporated by reference herein. Other heterologous protein secretion systems utilizing the autotransporter family can be modulated to result in either surface display or complete release into the medium (see Henderson et al., 2004, Type V secretion pathway: the autotransporter story, Microbiology and Molecular Biology Reviews 68: 692-744; Jose, 2006 Applied Microbiol. Biotechnol. 69: 607-614; Jose J, Zangen D (2005) Autodisplay of the protease inhibitor aprotinin in *Escherichia coli*. Biochem Biophys Res Commun 333:1218-1226 and Rutherford and Mourez 2006 Microbial Cell Factories 5: 22). For example, Veiga et al. (2003 Journal of Bacteriology 185: 5585-5590 and Klauser et al., 1990 EMBO Journal 9: 1991-1999) demonstrated hybrid proteins containing the β-autotransporter domain of the immunoglobulin A (IgA) protease of Nisseria gonorrhea. Fusions to flagellar proteins have been demonstrated. The peptide, usually of 15 to 36 amino acids in length, is inserted into the central, hypervariable region of the FliC gene such as that from *Salmonella muenchen* (Verma et al. 1995 Vaccine 13: 235-24; Wu et al., 1989 Proc. Natl. Acad. Sci. USA 86: 4726-4730; Cuadro et al., 2004 Infect. Immun. 72: 2810-2816; Newton et al., 1995, Res. Microbiol. 146: 203-216, expressly incorporated by reference in their entirety herein). Multihybrid FliC insertions of up to 302 amino acids have also been prepared (Tanskanen et al. 2000, Appl. Env. Microbiol. 66: 4152-4156, expressly incorporated by reference in its entirety herein). Trimerization of antigens can be achieved using the T4 fibritin foldon trimerization sequence (Wei et al. 2008 J. Virology 82: 6200-6208) and VASP tetramerization domains (Kühnel et al., 2004 PNAS 101: 17027-17032), expressly incorporated by reference in their entirety herein. The multimerization domains are used to create, bi-specific, tri-specific, and quatra-specific targeting agents, whereby each individual agent is expressed with a multimerization tag, each of which may have the same or separate targeting peptide, such that following expression, surface display, secretion and/or release, they form multimers with multiple targeting domains.

SUMMARY OF THE INVENTION

Modified Therapeutic Molecules

The present technology, according to various embodiments, consists of known and/or novel chimeric proteins, or combinations of proteins, that are expressed, secreted, surface displayed and/or released by bacteria and result in anticancer activity or have direct inhibitory or cytotoxic anti-neoplastic activity, including activity against cancer stem cells and/or cancer mesenchymal stromal cells, and may optionally include the combination with secreted protease inhibitors. The bacterial delivery vector may be attenuated, non-pathogenic, low pathogenic (including wild type), or a probiotic bacterium. The bacteria are introduced either systemically (e.g., parentral, intravenous (IV), intramuscular (IM), intralymphatic (IL), intradermal (ID), subcutaneously (sub-q), local-regionally (e.g., intralesionally, intratumorally (IT), intrapaeritoneally (IP), topically, intrathecally (intrathecal), by inhaler or nasal spray) or to the mucosal system through oral, nasal, pulmonary intravessically, enema or suppository administration where they are able to undergo limited replication, express, surface display, secrete and/or release the anti-cancer inhibitory proteins or a combination thereof, and thereby provide a therapeutic benefit by reducing or eliminating the disease, malignancy and/or neoplasia.

The present technology, according to various embodiments, further consists of modified forms of toxins with improved secretion, surface display and/or release by the bacteria, and/or modifications that improve the overall activity and/or specificity of the toxin. Such toxins may be further co-expressed with protease inhibitors as previously described (See, U.S. Pat. Nos. 8,241,623; 8,524,220; 8,771, 669; 8,524,220).

Toxins, therapeutic cytokines and other molecules, homologues or fragments thereof useful in conjunction with the present technology, according to various embodiments, includes small lytic peptides, larger lytic peptides, pore-forming toxins, protein inhibitors, extracellular DNAases (DNase), intracellular DNAases, apoptosis inducing peptides, cytokines, prodrug converting enzymes, metabolite destroying enzymes, ribonucleases, antibody inactivating toxins and other anticancer peptides. In a preferred embodiment, the toxins include those that are naturally secreted, released and/or surface displayed, or heterologously secreted, released and/or surface displayed, and that can be modified uniquely to suit the delivery by a bacterium and may be further engineered to have the tumor, lymphoma, leukemic bone marrow or proximity-selective targeting system described herein, including but not limited to the proteins azurin, carboxyesterase Est55 (a prodrug-converting enzyme from *Geobacillus* that activates CPT-11 to SN-38), thiaminase (e.g., from *Bacillus*), methionase (methioninase), asparaginase, tryptophanase, apoptin, Torquetnovirus (TTV) derived apoptosis-inducing protein TAIP and with gyrovirus VP3 bax, bim, p53, BAK, BH3 peptide (BCL2 homology domain 3), cytochrome C, thrombospondin, platlet factor 4 (PF4) peptide, *Bacillus* sp. cytolysins, *Bacillus* sp. nheABC toxins, cytolethal distending toxins (cldt) including those cldts from *Haemophilus, Aggregatibacter, Salmonella, Escherichia, Shigella, Campylobacter, Helicobacter, Hahella* and *Yersinia*, typhoid toxins (pertussis like toxin) (pltAB), pertussis toxin, cldt:plt hybrids, actAB, cytotoxic nectrotic factor (cnf), dermonecrotic factor (dnf), shiga toxins and shiga-like toxins, bacteriocins, (colicins and microcins; Hen and Jack, Chapter 13 Microcins, in Kastin (ed), 2006, Handbook of Biologically Active Peptides, Academic Press; Nes et al., Chapter 17, The nonlantibiotic heat-stable bacteriocins in gram-positive bacteria, in Kastin (ed), 2006, Handbook of Biologically Active Peptides, Academic Press; Sharma et al., Chapter 18 in Kastin (ed), 2006, Handbook of Biologically Active Peptides, Academic Press) including membrane depolarizing (or pore-forming), DNAases (including colicin DNase, Staphylococcal Nuclease A:OmpA fusions (Takahara et al., 1985 J. Biol. Chem 260: 2670-2674), *Serratia marcescens* DNase (Clegg and Allen, 1985, FEMS Microbiology Letters 27: 257-262; *Vibrio* DNase Newland et al., 1985 Infect Immun 47: 691-696) or other bacterial DNase), RNAases, and tRNAases, including but not limited colicin A, colicin D, colicin E5, colicin E492, microcin M24, colE1, colE2, colE3, colE5 colE7, coleE8, colE9, col-Ia, colicin N and colicin B, membrane lytic peptides from *Staphalococcus* (listed below) and sea anemones, P15 peptide and other TGF-beta mimics, repeat in toxin (RTX) family members (together with the necessary acylation and secretion genes) including *Actinobacillus* leucotoxins, a leuckotoxin: *E. coli* HlyA hybrid, *E. coli* HlyA hemolysin, *Bordetella* adenylate cyclase toxin, heat stable enterotoxins from *E. coli* and *Vibrio* sp. (Dubreuil 2006, Chapter 48, Eschericia *coli*, *Vibrio* and *Yersinia* species heat stable enterotoxins, Alouf and Popoff (eds), 2006, Comprehensive Sourcebook of Bacterial Protein Toxins, Third Edition, Academic Press), autotransporter toxins including but not limited to IgA protease, picU espC, and sat, *Staphalococcus* protein A, *chlostridium* enterotoxin, *Clostridium difficile* toxin A, scorpion chlorotoxin, aerolysin, subtilase, cereolysin, *Staphalococcus* leukotoxins (e.g. LukF-PV, LukF-R, LukF-I, LukM, HlgB) and the other, to class S (e.g. LukS-PV, LukS-R, LukS-I, HlgA, HlgC). Best known are the toxins produced by *S. aureus*: γ-haemolysins, HlgA/HlgB and HlgC/HlgB and leukocidin Panton-Valentine, LukS-PV/LukF-PV (Luk-PV, PVL)) TRAIL, fasL, IL-18, CCL-21, human cyokine LIGHT, agglutinins (*Maackia amurensis*, wheat germ, *Datura stramonium, Lycopersicon* (tomato) plant lectin, leukoagglutinin (L-PHA, *Helix pomatia*) saporin, ricin, pertussus toxin, and porB, as well as other toxins and peptides (Kastin (ed), 2006, Handbook of Biologically Active Peptides, Academic Press; Alouf and Popoff (eds), 2006, Comprehensive Sourcebook of Bacterial Protein Toxins, Third Edition, Academic Press; each of which is expressly incorporated by reference in their entirety herein). Metabolite toxins such as the *Chromobacterium violacium* dipsepeptides (Shigeatsu et al., 1994, FR901228, a novel antitumor bicyclic depsipeptide produced by *Chromobacterium violaceum* No. 968. II. Structure determination. J Antibiot (Tokyo) 47(3):311-4) or those from *Serratia* are also of use in the present technology.

The chimeras may be further modified by addition of one or more multimerization domains, such as the T4 foldon trimerization domain (Meier et al., 2004, Journal of Molecular Biology, 344: 1051-1069; Bhardwaj et al., Protein Sci. 2008 17: 1475-1485) or tetramerization domains such as VASP (Kühnel et al., 2004 PNAS 101: 17027-17032). Chimeric toxins may be further modified by the addition of known cell penetrating (ferry) peptide which further improves their entry into target cells. Cell penetrating peptides include those derived from the human immunodifficency virus (HIV) TAT protein amino acids 47-57 (YGRKKRRQRRR SEQ ID NO.: 020) and used in fusion proteins (e.g., TAT-apoptin, TAT-bim, TAT-p53), the antennapedia homeodomain (penetraxin), Kaposi fibroblast growth factor (FGF) membrane-translocating sequence (MTS), herpes simplex virus VP22, hexahistidine, hexylysine, hexaarginine or "Chariot" (Active Motif, Carlsbad, Calif.; U.S. Pat. No. 6,841,535). Nuclear localization signals (NLSs) may also be added, including but not limited to that from herpes simplex virus thymidine kinase, the SV40 large T antigen monopartite NLS, or the nucleoplamin bipartite NLS or more preferably, the NLS from apoptin, a tumor associated (tumor-selective) NLS. The tumor-selective nuclear export signal from apoptin may be used alone or together with NLS from apoptin (Heckl et al., 2008, Value of apoptin's 40-amino-acid C-terminal fragment for the differentiation between human tumor and non-tumor cells, Apoptosis 13: 495-508; Backendor et al., 2008, Apoptin: Therapeutic potential of an early sensor of carcinogenic transformation, Ann Rev Pharmacol Toxicol 48: 143-69).

Expression of wild type *Pseudomonas* exotoxin A has been previously described (U.S. Pat. Nos. 6,962,696; 7,452,531; 8,241,623; Swofford C A et al. 2014. Identification of *Staphylococcus aureus* α-hemolysin as a protein drug that is secreted by anticancer bacteria and rapidly kills cancer cells. Biotechnol Bioeng. 111:1233-45). Regarding chimeric *Pseudomonas* exotoxin A (ToxA), numerous forms have been generated and shown to be effective at killing tumor cells in vitro and in murine cancer models (TGF-α-GIII-KDEL (Kihara and I. Pastan 1994 Small Chimeric Toxins Containing Only Transforming Growth Factor α and Domain III of *Pseudomonas* Exotoxin with Good Antitumor Activity in Mice. Cancer Res 1994:54:5154-5159; TGF α-PE38; Kreitman et al., 1992, Properties of Chimeric Toxins with Two Recognition Domains: Interleukin 6 and Transforming Growth Factor α at Different Locations in *Pseudomonas* Exotoxin. Bioconjugate Chem. 1992, 3, 63-68; Kreitman et al., Recombinant immunotoxins containing anti-Tac(Fv) and derivatives of *Pseudomonas* exotoxin produce complete regression in mice of an interleukin 2 receptor-expressing human carcinoma. Blood 1994, 83, 426-434; Zielenski 2009, Affitoxin—A Novel Recombinant, HER2-Specific, Anti-Cancer Agent for Targeted Therapy of HER2-Positive Tumors. J Immunother. 32: 817-825). However, these investigators did not use a live bacterial vector to deliver the chimeric agent, and purified the agent from bacteria that were killed and lysed, generally requiring the biochemical manipulation of "refolding" of an inactively produced agent in the form of an inclusion body to produce the active form. The process of refolding an inactive inclusion body is not facilitated by live bacteria, and thus cannot be effective when delivered by a live bacterium expressing such a cancer therapeutic protein. Proteins produced in a "soluble" form, while not requiring refolding, likewise are ineffective because they do not get out of the cell. The present technology, according to various embodiments, uses, alone or in combination, ToxA domain Ib containing at least 2 available cysteines for cysteine bonds, flexible linkers, colicin lysis protein and/or signal sequences that result in functional ToxA chimeric proteins that are expressed, secreted, surface displayed and/or released by the bacteria and have the ability to kill cancer cells in the absence of biochemical manipulation.

Regarding use of tumor-targeted bacteria expressing wild type cytolethal distending toxin and chimeras including those with apoptin, there have been several earlier descriptions (U.S. Pat. Nos. 6,962,696; 7,452,531; 8,241,623; 8,524,220; 8,623,350; 8,771,669). Cytolethal distending toxins (CLDTs) comprise a family of heterotrimeric holotoxins produced by bacteria that are internalized into mammalian cells and translocated into the nucleus. CLDTs are known to occur in a number of bacterial genera including *Haemophilus, Aggregatibacter, Salmonella, Escherichia, Shigella, Campylobacter, Helicobacter, Hahella* and *Yersinia* (Gargi et al., 2012 Bacterial toxin modulation of the eukaryotic cell cycle: are all cytolethal distending toxins created equally? Frontiers in Cellular and Infection Microbiol. 2:124. doi: 10.3389/fcimb.2012.00124), however CLDT does not exist in the VNP20009 strain of *Salmonella* used in human clinical studies (Toso et al. 2002. Phase I Study of the Intravenous Administration of Attenuated *Salmonella typhimurium* to Patients With Metastatic Melanoma. J. Clin. Oncol. 20, 142-152; Low et al., 2004, Construction of VNP20009, a novel, genetically stable antibiotic sensitive strain of tumor-targeting *Salmonella* for parentral administration in humans. Methods Mol Med 90: 47-60).

Depending upon both the specific CLDT and the mammalian cells type, different effects have been documented. All CLDTs have homology to exonuclease III and several have been directly shown to exhibit DNase activity in vitro (Ewell and Dreyfus 2000 DNase I homologous residues in CdtB are critical for cytolethal distending toxin-mediated cell cycle arrest. Mol Microbiol 37, 952-963; Lara-Tejero and Galán, 2000 A bacterial toxin that controls cell cycle progression as a deoxyribonuclease I-like protein. Science 290, 354-357), which is believed to be the primary effect of the toxin. The DNase activity results in double-stranded DNA breaks that activates the cell's DNA damage response and interrupts the cell cycle at G2M. Non-haematopoetic cells tend to enlarge, hence part of the toxin name distending, and in many cases the cells subsequently undergo apoptosis. In haematopoitic cells apoptosis is more rapidly produced (Jinadasa et al., 2011, Cytolethal distending toxin: a conserved bacterial genotoxin that blocks cell cycle progression, leading to apoptosis of a broad range of mammalian cell lineages. Microbiology 157: 1851-1875; Gargi et al., 2012).

Most of the CLDTs are organized in a unidirectional operon of cldtA, cldtB and cldtC genes, where the cldtB encodes the active subcomponent, and cldtA and cldtC encode peptides that are involved in cell binding and translocation. In *Salmonella* however, the genes exist as a bidirectional operon consisting of cldtB together with a two pertussis like toxin subunits oriented in the opposite direction, pltA and pltB, as well as sty and ttsA, also in opposing directions, that are reported to be required for secretion of the toxin (Hodak and Galan 2013 A *Salmonella Typhi* homologue of bacteriophage muramidase controls typhoid toxin secretion. EMBO Reports 14: 95-102). However, in the present technology, according to various embodiments, the presence of sty and ttsA are not required for secretion of the active toxin when the operon is reorganized into a unidirectional operon of cldtB, pltB and pltA.

Translocation of *E. coli* CLDTs to the nucleus, which constitutes the target location for the endonuclease activity, requires the presence of a nuclear localization signal (NLS). In *Escherichia coli* CLDT-II for example, the NLS is bipartite and located at the C-terminus (McSweeney and Dreyfus, 2004). Nishikubo et al., 2003 identified an NLS occurring in the 48-124 amino acid region in *Actinobacillus actinomycetemcomitans.*

Apoptins are a family of viral genes that were first discovered in chicken anemia virus. Apoptin is the product of the VP3 gene that is involved in lymphoidal atropy and anemia in infected chickens (Peñaloza et al., 2014 Apoptins: selective anticancer agents, Trends in Molecular Medicine 20: 519-528; Los et al., 2009 Apoptin, a tumor selective killer, Biochimica et Biophysica Acta 1793: 1335-1342). Apoptin was subsequently found to selectively induce apoptosis in cancer cells (Danen-Van Oorschot et al., 1997 Apoptin induces apoptosis in human transformed and malignant cells but not in normal cells. Proc. Natl. Acad. Sci. USA 94: 5843-5847). Apoptin shares similarity with Torquetnovirus (TTV) derived apoptosis-inducing protein TAIP and with gyrovirus VP3. Apoptin consists of several different domains including a leucine rich sequence (LRS) which is involved in binding to the promyelocytic leukemia (PML) protein of nuclei and in apoptin multimerization, an SRC homology 3 (SH3) binding domain with is part of a bipartite nuclear localization signal (NLS), a nuclear export sequence (NES) that promotes egress of apoptin from normal cell nuclei, a set of threonines of which T108 must be phosphorylated for full apoptin activity, the C-terminal portion of the bipartite NLS and an anaphase promoting complex/cyclosome 1 (APC/Cl) binding domain that consists of approximately one third of the C-terminus.

The present technology, according to various embodiments, consists of a modified *Salmonella* CLDT operon and forms of cytolethal distending toxins that are chimeric with apoptin and other peptide moieties including peptide linkers that improve activity and peptide blocking moieties that must be specifically cleaved to activate the protein. The present technology, according to various embodiments, uses deletions in the the CLDT nuclear localization signals which are then complemented by N- or C-terminal fusions with apoptin, or apoptin fragments, which supply its nuclear localization signal in trans as a fusion peptide.

The types of cancers or neoplasias to which the present technology is directed include all neoplastic malignancies, including solid tumors such as those of colon, lung, breast, prostate, sarcomas, carcinomas, head and neck tumors, melanoma, as well as hematological, non-solid or diffuse cancers such as leukemia and lymphomas, myelodysplastic cells, plasma cell myeloma, plasmacytomas, and multiple myelomas. Specific types of cancers include acute lymphoblastic leukemia, acute myeloid leukemia, adrenocortical carcinoma adrenocortical carcinoma, adult (primary) liver cancer, adult acute myeloid leukemia, AIDS-related cancers, AIDS-related lymphoma, anal cancer, appendix cancer, astrocytomas, astrocytomas (childhood), basal cell carcinoma, bile duct cancer, bladder cancer, bone cancer, brain stem glioma, brain tumor, breast cancer (female), breast cancer (male), bronchial tumors, Burkitt's lymphoma, carcinoid tumor, carcinoma of unknown primary site, central nervous system atypical teratoid/rhabdoid tumor, central nervous system embryonal tumors, central nervous system lymphoma, central nervous system tumors, cervical cancer, childhood acute myeloma, childhood multiple myeloma/plasma cell neoplasm, chordoma, chronic lymphocytic leukemia, chronic myelogenous leukemia, chronic myeloid leukemia, chronic myeloproliferative disorders, colon cancer, colorectal cancer, craniopharyngioma, cutaneous T-cell lymphoma, embryonal tumors, endometrial cancer, endometrial uterine sarcoma, ependymoblastoma, ependymoma, esophageal cancer, Ewing sarcoma family of tumors, extracranial germ cell tumor, extragonadal germ cell tumor, extrahepatic bile duct cancer, extrahepatic gallbladder cancer, eye cancer, gallbladder cancer, gastric (stomach) cancer, gastrointestinal carcinoma, gastrointestinal carcinoid tumor, gastrointestinal stromal cell tumor, gastrointestinal stromal tumor (gist), germ cell tumor, glioma, hairy cell leukemia, head and neck cancer, hepatocellular (liver) cancer, histiocytosis, Hodgkin lymphoma, hypopharyngeal cancer, intraocular (eye) melanoma, intraocular melanoma, islet cell tumors, Kaposi sarcoma, kidney (renal cell) cancer, kidney cancer, Langerhans cell, Langerhans cell histiocytosis, laryngeal cancer, leukemia, lip and oral cavity cancer, lip and oropharyngeal cancer, liver cancer (metastatic), lung cancer (primary), macroglobulinemia, medulloblastoma, medulloepithelioma, melanoma, Merkel cell carcinoma, mesothelioma, metastatic squamous neck cancer with occult primary, metastatic stomach (gastric) cancer, mouth cancer, multiple endocrine neoplasia syndrome, multiple myeloproliferative disorders, mycosis fungoides, myelodysplastic syndromes, myelodysplastic/myeloproliferative diseases, myelogenous leukemia, nasal cavity and paranasal sinus cancer, nasopharyngeal cancer, nervous system atypical teratoid/rhabdoid tumor, neuroblastoma, non-Hodgkin lymphoma, non-small cell lung cancer, oral cancer, oral cavity cancer, osteosarcoma and malignant fibrous histiocytoma, osteosarcoma and malignant fibrous histiocytoma of bone, ovarian cancer, ovarian epithelial cancer, ovarian germ cell tumor, ovarian gestational trophoblastic tumor, ovarian low malignant potential tumor, pancreatic cancer, papillomatosis, paranasal sinus and nasal cavity cancer, parathyroid cancer, penile cancer, pharyngeal cancer, pineal parenchymal tumors, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, primary cervical cancer, primary hepatocellular (liver) cancer, prostate cancer, rectal cancer, renal cell (kidney) cancer, renal pelvis and ureter, respiratory tract carcinoma involving the nut gene on chromosome 15, retinoblastoma, rhabdomyosarcoma, salivary gland cancer, sarcoma, skin cancer (Basal cell carcinoma), Sézary syndrome, skin cancer (nonmelanoma), skin carcinoma, small cell lung cancer, small cell lymphoma, small intestine cancer, soft tissue sarcoma, spinal cord tumors, squamous cell carcinoma, squamous neck cancer with occult primary, stomach (gastric) cancer, supratentorial primitive neuroectodermal tumors and pineoblastoma, T-cell lymphoma, teratoid/rhabdoid tumor (childhood), testicular cancer, throat cancer, thymoma and thymic carcinoma, thyroid cancer, transitional cell cancer, transitional cell cancer of the renal pelvis and ureter, trophoblastic tumor (gestational), unknown primary site, ureter and renal pelvis, urethral cancer, uterine cancer, uterine sarcoma, vaginal cancer, vulvar cancer, Waldenström macroglobulinemia, Waldenström malignant fibrous histiocytoma of bone and osteosarcoma, and Wilms tumor.

The therapeutic agent can be a chimera consisting of a peptide or protein, toxin, chimeric toxin, cytokine, antibody, bispecific antibody including single chain antibodies, camel antibodies and nanobodies chemokine, prodrug converting enzyme or metabolite-degrading enzyme such as thiaminase, methionase (methioninase, L-methionine γ-lyase) or asparaginase. In a preferred embodiment the therapeutic agent is a toxin, or modified toxin.

The chimeras may be further modified by addition of one or more multimerization domains, such as the T4 foldon trimerization domain (Meier et al., 2004, Journal of Molecular Biology, 344: 1051-1069; Bhardwaj et al., Protein Sci. 2008 17: 1475-1485) or tetramerization domains such as VASP (Kühnel et al., 2004 PNAS 101: 17027-17032). Chimeric toxins may be further modified by the addition of known cell penetrating (ferry) peptide which further improves their entry into target cells. Cell penetrating peptides include those derived from the HIV TAT protein (e.g., TAT-apoptin, TAT-bim, TAT-p53), the antennapedia homeodomain (penetraxin), Kaposi fibroblast growth factor (FGF) membrane-translocating sequence (MTS), herpes simplex virus VP22, hexahistidine, hexalysine, hexaarginine or "Chariot" (Active Motif, Carlsbad, Calif.; U.S. Pat. No. 6,841,535). Nuclear localization signals (NLSs) may also be added, including but not limited to that from herpes simplex virus thymidine kinase, the SV40 large T antigen monopartite NLS, or the nucleoplasmin bipartite NLS or more preferably, the NLS from apoptin, a tumor associated (tumor-selective) NLS. The tumor-selective nuclear export signal from apoptin may be used alone or together with NLS from apoptin (Heckl et al., 2008, Value of apoptin's 40-amino-acid C-terminal fragment for the differentiation between human tumor and non-tumor cells, Apoptosis 13: 495-508; Backendor et al., 2008, Apoptin: Therapeutic potential of an early sensor of carcinogenic transformation, Ann Rev Pharmacol Toxicol 48: 143-69).

The chimeric proteins may have one or more additional features or protein domains known to those skilled in the art which are designed to be active or catalytic domains that result in the death of the cell, allow or facilitate them being secreted or released by autolytic peptides such as those associated with colicins or bacteriophage release peptides have targeting peptides that direct them to the target cells, and protease cleavage sites for activation (e.g., release from parent peptide), and thioredoxin or glutathione S-transferase (GST) fusions that improve solubility.

The present technology also provides in accordance with some embodiments, unique chimeric modifications of the above listed toxins that contain specific combinations of components resulting in secretion by selective anti-tumor activity. The technology also provides extracellular protease sensitivity (deactivation) that may include the addition of protease cleavage sites and may be co-expressed with a protease inhibitor. The chimeric proteins may have one or more additional features or protein domains known to those skilled in the art which are designed to 1) be active or catalytic domains that result in the death of the cell or make them susceptible to other known anticancer agents, 2) allow or facilitate them being secreted or released by autolytic peptides such as colicin release peptides, 3) membrane protein transduction (ferry) peptides, 4) autotransporter domains, 5) have targeting peptides that direct them to the target cells, and 6) protease cleavage sites for activation (e.g., release from parent peptide). However, the specific organization and combination of these domains is unique and specific to the technology.

Small lytic peptides (less than 50 amino acids) are used to construct chimeric proteins for more than one purpose. The chimeric proteins containing lytic peptides may be directly cytotoxic for the cancer cells, and/or other cells of the tumor including the tumor matrix cells and immune cells which may diminish the effects of the bacteria by eliminating them. Furthermore, the lytic peptides are useful in chimeric proteins for affecting release from the endosome. Small lytic peptides have been used in the experimental treatment of cancer. However, it is evident that most, if not all, of the commonly used antitumor small lytic peptides have strong antibacterial activity, and thus are not compatible with delivery by a bacterium (see Table 1 of Leschner and Hansel, 2004 Current Pharmaceutical Design 10: 2299-2310, the entirety of which is expressly incorporated herein by reference). Small lytic peptides useful in the technology, according to various embodiments, are those derived from *Staphaloccus aureus, S. epidermidis* and related species, including the phenol-soluble modulin (PSM) peptides and delta-lysin (Wang et al., 2007 Nature Medicine 13: 1510-1514, expressly incorporated herein by reference). Larger lytic peptides that may be used includes the actinoporins from sea anemones or other coelenterates, such as SrcI, FraC equinatoxin-II and sticholysin-II (Anderluh and Macek 2002, Toxicon 40: 111-124). The selection of the lytic peptide depends upon the primary purpose of the construct, which may be used in combination with other constructs providing other anticancer features. Construct designed to be directly cytotoxic to cells employ the more cytotoxic peptides, particularly PSM-α-3 and actinoporins. Constructs which are designed to use the lytic peptide to affect escape from the endosome use the peptides with the lower level of cytotoxicity, such as PSM-alpha-1, PSM-α-2 or delta-lysin.

Promoters, i.e., genetic regulatory elements that control the expression of the genes encoding the therapeutic molecules described above that are useful in the present technology, according to various embodiments, include constitutive and inducible promoters. A preferred constitutive promoter is that from the vector pTrc99a (Promega). Preferred inducible promoters include the tetracycline inducible promoter (TET promoter), SOS-response promoters responsive to DNA damaging agents such as mitomycin, alkylating agents, X-rays and ultraviolet (UV) light such as the recA promoter, colicin promoters, sulA promoters and hypoxic-inducible promoters including but not limited to the PepT promoter (Bermudes et al., WO 01/25397), the arabinose inducible promoter (AraBAD) (Los sner et al., 2007, Cell Microbiol. 9: 1529-1537; WO/2006/048344) the salicylate (aspirin) derivatives inducible promoter (Royo et al., 2007, Nature Methods 4: 937-942; WO/2005/054477), a tumor-specific promoter (Arrach et al., 2008, Cancer Research 68: 4827-4832; WO/2009/152480) or a quorum-sensing (auto-induction) promoter Anerson et al., 2006 Environmentally controlled invasion of cancer cells by engineered bacteria, J. Mol. Biol. 355: 619-627.

A single promoter may be used to drive the expression of more than one gene, such as a protease sensitive toxin and a protease inhibitor. The genes may be part of a single synthetic operon (polycistronic), or may be separate, monocystronic constructs, with separate individual promoters of the same type used to drive the expression of their respective genes. The promoters may also be of different types, with different genes expressed by different constitutive or inducible promoters. Use of two separate inducible promoter for more than one cytotoxin or other effector type peptide allows, when sufficient X-ray, tetracycline, arabinose or salicylic acid is administered following administration of the bacterial vector, their expression to occur simultaneously, sequentially, or alternatingly (i.e., repeated).

OBJECTS OF THE INVENTION

The present technology provides, according to one embodiment, live attenuated therapeutic bacterial strains that express one or more therapeutic molecules. The technology, according to various embodiments, relates specifically to certain modified forms of chimeric toxins especially suitable for expression by tumor-targeted bacteria. In a preferred embodiment, the modified toxin is derived from *Pseudomonas* exotoxin A (ToxA). In another preferred embodiment, the toxin is derived from cytolethal distending toxin. In a more preferred embodiment, the cytolethal distending toxin is derived from *Salmonella paratyphi* A, *Salmonella typhi* or *Salmonella bongori*. In particular, the technology, according to various embodiments, relates to live attenuated tumor-targeted bacterial strains that may include *Salmonella* sp., group B *Streptococcus* or *Listeria* vectoring chimeric anti-tumor toxins to an individual to elicit a therapeutic response against cancer. Another aspect of the technology relates to live attenuated tumor-targeted bacterial strains that may include *Salmonella*, group B *Streptococcus* or *Listeria* vectoring chimeric anti-tumor toxin molecules to an individual to elicit a therapeutic response against cancer including cancer stem cells. The toxins may also be targeted to tumor matrix cells, and/or immune cells. In another embodiment of the technology, *Salmonella* strains including *Salmonella paratyphi* A, *Salmonella typhi* or *Salmonella bongori* which contain endogenous cytolethal distending toxins may, when suitably attenuated, be used as vectors for delivery of cytolethal distending toxin. In order to achieve inducible control, the endogenous reporter is replaced with an inducible promoter by homologous recombination. In another embodiment, a chimeric secreted protease inhibitor is used alone or in combination with the chimeric toxins.

Whereas the prior strains of *Salmonella* studied in human clinical trials used either no heterologous antitumor protein (i.e., VNP20009) or an antitumor protein located within the cytoplasm of the bacterium (i.e., cytosine deaminase expressed by TAPET-CD), or secreted proteins (Bermudes et al., WO 2001/025397) the technology, according to various embodiments, provides, according to some embodiments, methods and compositions comprising bacterial vectors that express, secrete, surface display and/or release protease inhibitors that protect co-expressed protease sensitive anti-tumor molecules that are also secreted, surface displayed and/or released into the tumor, lymphoma-containing lymph node, leukemic bone lumen, or proximally or topically on a carcinoma or precancerous lesion for the treatment of the neoplasia.

The primary characteristic of the bacteria of the technology, according to various embodiments, is the enhanced effect of the effector molecule such as a toxin, lytic peptide etc. relative to the parental strain of bacteria. In one embodiment, the percent increase in effect is approximately 2% to approximately 95%, approximately 2% to approximately 75%, approximately 2% to approximately 50%, approximately 2% to about 40%, approximately 2% to about 30%, approximately 2% to about 25%, approximately 2% to about 20% or about 2% to approximately 10% greater than the parental strain of bacteria without expressing one or more protease inhibitors under the same conditions. A second characteristic of the bacteria of the technology, according to various embodiments, is that they carry novel chimeric proteins that improve their function compared to other chimeric protein expression systems. In one embodiment, the percent improvement is approximately 2% to approximately 95%, approximately 2% to approximately 75%, approximately 2% to approximately 50%, approximately 2% to about 40%, approximately 2% to about 30%, approximately 2% to about 25%, approximately 2% to about 20% or about 2% to approximately 10% that of another expression system under the same conditions.

The bacteria according to a preferred embodiment of the present technology, according to various embodiments, include those modified to have little or no ability to undergo bacterial conjugation, limiting incoming and outgoing exchange of genetic material, whereas the prior art fails to limit exchange of genetic material. In addition, certain of the therapeutic molecules have co-transmission requirements (e.g., colicin proteins and colicin immunity) that are distal (i.e., genetically dissected and separated) to the therapeutic molecule location further limiting known forms of genetic exchange.

Aspects of the present technology also provide novel chimeric bacterial toxins particularly suited for expression by gram-negative bacteria. The toxins may have added targeting ligands that render them selectively cytotoxic for tumor cells, tumor stem cells and/or matrix and tumor-infiltrating immune cells. The technology also provides means to determine optimal toxin combinations which are preferably additive or more preferably synergistic. The technology also provides means to determine the optimal combination of protein toxin with conventional cancer chemotherapeutics, liposomal agents or biologics, including immunosuppressive anti-complement agents (e.g., anti-C5B). Accordingly, administration to an individual, of a live *Salmonella* bacterial vector, in accordance with an aspect of the present technology, that is genetically engineered to express one or more protease inhibitors as described herein co-expressed with one or more cytotoxic proteins has the ability to establish a population in the tumor, kill tumor cells, tumor stem cells as well as tumor matrix and immune infiltrating cells, resulting in a therapeutic benefit.

A preferred composition will contain, for example, a sufficient amount of live bacteria expressing the targeted cytotoxin(s) or effector proteins/peptides to produce a therapeutic response in the patient. Accordingly, the attenuated *Salmonella* strains described herein are both safe and useful as live bacterial vectors that can be systemically or orally administered to an individual to provide therapeutic benefit for the treatment of cancer.

Although not wishing to be bound by any particular mechanism, an effective antitumor response in humans by administration of genetically engineered, attenuated strains of *Salmonella* strains as described herein may be due to the ability of such mutant strains to persist within the tumor, lymphoma or leukemic bone marrow and to supply their own nutrient needs by killing tumor cells, tumor matrix and or immune infiltrating cells and further expanding the zone of the tumor that they occupy. Bacterial strains useful in accordance with a preferred aspect of the technology may carry the ability to produce a therapeutic molecule expressing plasmid or chromosomally integrated cassette that encodes and directs expression of one or more therapeutic molecules together with optionally one or more protease inhibitors, as described herein. The protease inhibitors serve to prevent the destruction of the therapeutic molecule while within the tumor. The protease inhibitor may also have an anticlotting effect, wherein a blood clot may prevent spread of the bacteria throughout the tumor. The protease inhibitor may also have direct or indirect anticancer effects through the inhibition of proteases that participate in the spread of cancerous cells. If the cytotoxin and protease inhibitor diffuse outside of the tumor, lymph node, bone lumen, proximity to a carcinoma or other neoplasia-localized distribution, they fall below the protease inhibitory concentration, no longer inhibit proteolysis of the cytotoxins or effector genes, and are then inactivated. Thus the protease inhibitor system both increases activity and provides tumor specificity.

The serovars of *S. enterica* that may be used as the attenuated bacterium of the live compositions described in accordance with various embodiments herein include, without limitation, *Salmonella enterica* serovar *Typhimurium* ("*S. typhimurium*"), *Salmonella montevideo*, *Salmonella enterica* serovar *Typhi* ("*S. typhi*"), *Salmonella enterica* serovar *Paratyphi* A ("*S. paratyphi* A"), *Salmonella enterica* serovar *Paratyphi* B ("*S. paratyphi* B"), *Salmonella enterica* serovar *Paratyphi* C ("*S. paratyphi* C"), *Salmonella enterica* serovar *Hadar* ("*S. hadar*"), *Salmonella enterica* serovar *Enteriditis* ("*S. enteriditis*"), *Salmonella enterica* serovar *Kentucky* ("*S. kentucky*"), *Salmonella enterica* serovar *Infantis* ("*S. infantis*"), *Salmonella enterica* serovar *Pullorum* ("*S. pullorum*"), *Salmonella enterica* serovar *Gallinarum* ("*S. gallinarum*"), *Salmonella enterica* serovar *Muenchen* ("*S. muenchen*"), *Salmonella enterica* serovar *Anaturn* ("*S. anatum*"), *Salmonella enterica* serovar *Dublin* ("*S. dublin*"), *Salmonella enterica* serovar *Derby* ("*S. derby*"), *Salmonella enterica* serovar *Choleraesuis* var. *Kunzendorf* ("*S. cholerae kunzendorf*), and *Salmonella enterica* serovar *Minnesota* (*S. minnesota*). A preferred serotype for the treatment of bone marrow related diseases is *S. dublin*. In another embodiment of the technology, *Salmonella* strains including *Salmonella paratyphi* A, *Salmonella typhi* or *Salmonella bongori* which contain endogenous cytolethal distending toxins, may, when suitably attenuated, be used as vectors for delivery of cytolethal distending toxin. In order to achieve inducible control, the endogenous reporter is replaced with an inducible promoter by homologous recombination.

By way of example, live bacteria in accordance with aspects of the technology include known strains of *S. enterica* serovar *Typhimurium* (*S. typhimurium*) and *S. enterica* serovar *Typhi* (*S. typhi*) which are further modified as provided by the technology to form vectors for the prevention and/or treatment of neoplasia. Such Strains include Ty21a, CMV906, CMV908, CMV906-htr, CMV908-htr, Ty800, aroA-/serC-, holavax, M01ZH09, VNP20009. These strains contain defined mutations within specific serotypes of bacteria. The technology also includes the use of these same mutational combinations contained within alternate serotypes or strains in order to avoid immune reactions which may occur in subsequent administrations. In a preferred embodiment, *S. Typhimurium*, *S. montevideo*, and *S. typhi* which have non-overlapping O-antigen presentation (e.g., *S. typhimurium* is O-1, 4, 5, 12 and *S. typhi* is Vi, *S. montevideo* is O-6, 7) may be used. Thus, for example, *S. typhimurium* is a suitable serotype for a first injection and another serotype such as *S. typhi* or *S. montevideo* are used for a second injection and third injections. Likewise, the flagellar antigens are also selected for non-overlapping antigenicity between different injections. The flagellar antigen may be H1 or H2 or no flagellar antigen, which, when combined with the three different O-antigen serotypes, provides three completely different antigenic profiles.

Novel strains of *Salmonella* are also encompassed that are, for example, attenuated in virulence by mutations in a variety of metabolic and structural genes. The technology therefore may provide a live composition for treating cancer comprising a live attenuated bacterium that is a serovar of *Salmonella enterica* comprising an attenuating mutation in a genetic locus of the chromosome of said bacterium that attenuates virulence of said bacterium and wherein said attenuating mutation is a combinations of other known attenuating mutations. Other attenuating mutation useful in the *Salmonella* bacterial strains described herein may be in a genetic locus selected from the group consisting of phoP, phoQ, edt, cya, crp, poxA, rpoS, htrA, nuoG, pmi, pabA, pts, damA, met, cys, pur, purA, purB, purI, purF, leu, ilv, arg, lys, zwf, aroA, aroB, aroC, aroD, serC, gua, cadA, rfc, rjb, rfa, ompR, msbB, pfkAB, crr, glk, ptsG, ptsHI, manXYZ and combinations thereof. The strain may also contain a mutation known as "Suwwan", which is an approximately 100 kB deletion between two IS200 elements. The strain may also carry a defective thioredoxin gene (trxA-; which may be used in combination with a TrxA fusion), a defective glutathione oxidoreductase (gor-) and optionally, overexpress a protein disulfide bond isomerase (DsbA). The strain may also be engineered to express invasion and/or escape genes tlyA, tlyC patI and pld from *Rickettsia*, whereby the bacteria exhibit enhanced invasion and/or escape from the phagolysosome (Witworth et al., 2005, Infect. Immun. 73:6668-6673), thereby enhancing the activity of the effector genes described below. The strain may also be engineered to be deleted in an avirulence (anti-virulence) gene, such as zirTS, grvA and/or pcgL, or express the *E. coli* lac repressor, which is also an avirulence gene in order to compensate for over-attenuation. The strain may also express SlyA, a known transcriptional activator. In a preferred embodiment, the *Salmonella* strains are msbB mutants (msbB-). In a more preferred embodiment, the strains are msbB- and Suwwan. In a more preferred embodiment the strains are msbB-, Suwwan and zwf-. Zwf has recently been shown to provide resistance to CO2, acidic pH and osmolarity (Karsten et al., 2009, BMC Microbiology August 18; 9:170). Use of the msbB zwf genetic combination is also particularly preferred for use in combination with administered carbogen (an oxygen carbon dioxide mixture that may enhance delivery of therapeutic agents to a tumor). In a more preferred embodiment, the strains are msbB-, Suwwan, zwf- and trxA-. In a most preferred embodiment, the strains are msbB-, Suwwan, zwf-, trxA- and gor-.

The technology also encompasses according to a preferred embodiment, gram-positive bacteria. Preferred bacteria of the technology are group B *Streptococcus* including *S. agalaciae*, and *Listeria* species including *L. monocytogenes*. It is known to those skilled in the art that minor variations in molecular biology techniques such as use of gram-positive origins of replication, gram-positive signal sequences gram-positive promoters (e.g., *Lactococcus* expression, Mohamadzadeh et al., PNAS Mar. 17, 2009 vol. 106 no. 11 4331-4336; Geertsma and Poolman, 2007, High-throughput cloning and expression in recalcitrant bacteria, Nature Methods 4: 705-707; Prudhomme et al., 2006, Antibiotic stress induces genetic transformability in the human pathogen *Streptococcus pneumoniae*, Science 313: 89-92; WO/2009/139985 Methods and materials for gastrointestinal delivery of a pathogen toxin binding agent; van Asseldonk, M et al. 1990, Cloning of usp45, a gene encoding a secreted protein from *Lactococcus lactis* subsp. *lactis* MG1363 Gene 95, 15-160; Kim et al., J Appl Microbiol. 2008 June; 104(6):1636-43. Epub 2008 Feb. 19. Display of heterologous proteins on the surface of *Lactococcus lactis* using the H and W domain of PrtB from *Lactobacillus delburueckii* subsp. *bulgaricus* as an anchoring matrix; Lee et al., 1999, Characterization of *Enterococcus faecalis* alkaline phosphatase and use in identifying *Streptococcus agalactiae* secreted proteins, J. Bacteriol 181(18):5790-9.) are required and substituted as needed.

Mutational backgrounds of *Listeria* vectors include those previously isolated, including the delta-actA strain 142 (Wallecha et al., 2009, Construction and characterization of an attenuated *Listera monocytogenes* strain for clinical use in cancer immunotherapy, Clin Vaccine Immunol 16: 96-103), the double D-alanine (D-ala) strain described by Jiang et al., 2007, Vaccine 16: 7470-7479, Yoshimura et al., 2006, Cancer Research 66: 1096-1104, Lenz et al., 2008, Clinical and Vaccine Immunology 15: 1414-1419, Roberts et al., 2005, Definition of genetically distinct attenuation mechanisms in naturally virulent *Listeria moncyogenes* by comparative cell culture and molecular characterization, Appl. Environ. Microbiol 71: 3900-3910, the actA, prfA strain by Yan et al., Infect Immun 76: 3439-3450, and those described by Portnoy et al., EP1513924 and Portnoy et al., WO/2003/102168.

Mutational backgrounds of the group B *Streptococcus*, *S. agalactiae*, include wild type (no mutations), of any of the nine serotypes that depend on the immunologic reactivity of the polysaccharide capsule and among nine serotypes, preferably types Ia, Ib, II, III, and V capable of being invasive in humans. The strain may be deleted in the beta-hemolysin/cytolysin (beta-H/C), including any member of the cly operon, preferably the clyE gene, or the CspA protease associated with virulence (Shelver and Bryan, 2008, J Bacteriol. 136: 129-134), or the hyaluronate lyse C5a peptidase CAMP factor, oligopeptidase (Liu and Nizet 2004, Frontiers in Biosci 9: 1794-1802; Doran and Nizet 2004, Mol Microbiol 54: 23-31; Herbert et al., 2004, Curr Opin Infect Dis 17: 225-229). The strains may further have mutations in metabolic genes pur, purA, aroA, aroB, aroC, aroD, pgi (glucose-6-phosphate isomerase), fructose-1,6-bisphosphatase, ptsH, ptsI, and/or one or more amino acid transporters and/or amino acid permeases. In a preferred embodiment, the strain is clyE deficient.

Other bacterial strains are also encompassed, including non-pathogenic bacteria of the gut such as *E. coli* strains, *Bacteroides*, *Bifidobacterium* and *Bacillus*, attenuated pathogenic strains of *E. coli* including enteropathogenic and uropathogenic isolates, *Enterococcus* sp. and *Serratia* sp. as well as attenuated *Shigella* sp., *Yersinia* sp., *Streptococcus* sp. and *Listeria* sp.

Bacteria of low pathogenic potential to humans such as *Clostridium* spp. and attenuated *Clostridium* spp., *Proteus mirabilis*, insect pathogenic *Xenorhabdus* sp., *Photorhabdus* sp. and human wound *Photorhabdus* (*Xenorhabdus*) are also encompassed. Probiotic strains of bacteria are also encompassed, including *Lactobacillus* sp., *Lactococcus* sp., *Leuconostoc* sp., *Pediococcus* sp., *Streptococcus* sp., *Streptococcus agalactiae*, *Lactococcus* sp., *Bacillus* sp., *Bacillus natto*, *Bifidobacterium* sp., *Bacteroides* sp., and *Escherichia coli* such as the 1917 Nissel strain.

The technology also provides, according to one embodiment, a process for preparing genetically stable therapeutic bacterial strains comprising genetically engineering the therapeutic genes of interest into a bacterially codon optimized expression sequence within a bacterial plasmid expression vector, endogenous virulence (VIR) plasmid (of *Salmonella* sp.), or chromosomal localization expression vector for any of the deleted genes or IS200 genes, defective phage or intergenic regions within the strain and further containing engineered restriction endonuclease sites such that the bacterially codon optimized expression gene contains subcomponents which are easily and rapidly exchangeable, and the bacterial strains so produced. Administration of the strain to the patient is therapeutic for the treatment of cancer.

The present technology provides, for example, and without limitation, live bacterial compositions that are genetically engineered to express one or more protease inhibitors combined with antitumor effector molecules for the treatment of cancers or neoplasias.

According to various embodiments, the technology provides pharmaceutical compositions comprising pharmaceutically acceptable carriers and one or more bacterial mutants. The technology also provides pharmaceutical compositions comprising pharmaceutically acceptable carriers and one or more bacterial mutants comprising nucleotide sequences encoding one or more therapeutic molecules. The pharmaceutical compositions of the technology may be used in accordance with the methods of the technology for the prophylaxis or treatment of neoplastic disease. Preferably, the bacterial mutants are attenuated by introducing one or more mutations in one or more genes in the lipopolysaccharide (LPS) biosynthetic pathway (for gram-negative bacteria), and optionally one or more mutations to auxotrophy for one or more nutrients or metabolites.

In one embodiment, a pharmaceutical composition comprises a pharmaceutically acceptable carrier and one or more bacterial mutants, wherein said attenuated bacterial mutants are facultative anaerobes or facultative aerobes. In another embodiment, a pharmaceutical composition comprises a pharmaceutically acceptable carrier and one or more attenuated bacterial mutants, wherein said attenuated bacterial mutants are facultative anaerobes or facultative aerobes and comprise one or more nucleic acid molecules encoding one or more therapeutic molecules where the therapeutic molecule is chimeric toxin.

In one embodiment, a pharmaceutical composition comprises a pharmaceutically acceptable carrier and one or more bacterial mutants, wherein said attenuated bacterial mutants are facultative anaerobes or facultative aerobes. In another embodiment, a pharmaceutical composition comprises a pharmaceutically acceptable carrier and one or more attenuated bacterial mutants, wherein said attenuated bacterial mutants are facultative anaerobes or facultative aerobes and comprise one or more nucleic acid molecules encoding one or more therapeutic molecules where the therapeutic molecule is a molecule with direct anti-cancer lytic capability.

In one embodiment, a pharmaceutical composition comprises a pharmaceutically acceptable carrier and one or more bacterial mutants, wherein said attenuated bacterial mutants are facultative anaerobes or facultative aerobes. In another embodiment, a pharmaceutical composition comprises a pharmaceutically acceptable carrier and one or more attenuated bacterial mutants, wherein said attenuated bacterial mutants are facultative anaerobes or facultative aerobes and comprise one or more nucleic acid molecules encoding one or more therapeutic molecules where the therapeutic molecule has direct anti-cancer cytotoxic or inhibitory ability.

In one embodiment, a pharmaceutical composition comprises a pharmaceutically acceptable carrier and one or more bacterial mutants, wherein said attenuated bacterial mutants are facultative anaerobes or facultative aerobes. In another embodiment, a pharmaceutical composition comprises a pharmaceutically acceptable carrier and one or more attenuated bacterial mutants, wherein said attenuated bacterial mutants are facultative anaerobes or facultative aerobes and comprise one or more nucleic acid molecules encoding one or more therapeutic molecules where the therapeutic molecule has direct anti-cellular activity against other cells of a tumor, including neutrophils, macrophages, T-cells, stromal cells, endothelial cells (tumor vasculature) and/or cancer stem cells.

In one embodiment, a pharmaceutical composition comprises a pharmaceutically acceptable carrier and one or more bacterial mutants, wherein said attenuated bacterial mutants are facultative anaerobes or facultative aerobes. In another embodiment, a pharmaceutical composition comprises a pharmaceutically acceptable carrier and one or more attenuated bacterial mutants, wherein said attenuated bacterial mutants are facultative anaerobes or facultative aerobes and comprise one or more nucleic acid molecules encoding one or more therapeutic molecules co-expressed with a protease inhibitor.

In a specific embodiment, a pharmaceutical composition comprises a pharmaceutically acceptable carrier and one or more attenuated bacterial mutants, wherein the bacterial mutants are a *Salmonella* sp. In another specific embodiment, a pharmaceutical composition comprises a pharmaceutically acceptable carrier and one or more attenuated stress-resistant gram-negative bacterial mutants, wherein the attenuated stress-resistant gram-negative bacterial mutants are a *Salmonella* sp., and the attenuated stress-resistant gram-negative bacterial mutants comprise one or more nucleic acid molecules encoding one or more therapeutic molecules, prodrug converting enzymes, metabolite degrading enzymes, lytic peptides, DNAases or anti-cancer peptides.

In a specific embodiment, a pharmaceutical composition comprises a pharmaceutically acceptable carrier and one or more attenuated bacterial mutants, wherein the bacterial mutants are a *Streptococcus* sp. In another specific embodiment, a pharmaceutical composition comprises a pharmaceutically acceptable carrier and one or more attenuated gram-positive bacterial mutants, wherein the attenuated gram-positive bacterial mutants are a *Streptococcus* sp., and the attenuated gram-positive bacterial mutants comprise one or more nucleic acid molecules encoding one or more therapeutic molecules, prodrug converting enzymes, metabolite degrading enzyme, lytic peptides, DNAases or anti-cancer peptides.

In a specific embodiment, a pharmaceutical composition comprises a pharmaceutically acceptable carrier and one or more attenuated bacterial mutants, wherein the bacterial mutants are a *Listeria* sp. In another specific embodiment, a pharmaceutical composition comprises a pharmaceutically acceptable carrier and one or more attenuated bacterial mutants, wherein the attenuated gram-positive bacterial mutants are a *Listeria* sp., and the attenuated gram-positive bacterial mutants comprise one or more nucleic acid molecules encoding one or more therapeutic molecules, prodrug converting enzymes, metabolite degrading enzyme, lytic peptides, DNAases or anti-cancer peptides.

The present technology, according to various embodiments, encompasses treatment protocols that provide a better therapeutic effect than current existing anticancer therapies. In particular, the present technology provides methods for prophylaxis or treatment of neoplastic diseases in a subject comprising administering to said subject and one or more bacterial mutants. The present technology also provides methods for the prophylaxis or treatment of neoplastic diseases in a subject comprising administering to said subject one or more bacterial mutants, wherein said bacterial mutants comprise one or more nucleic acid molecules encoding one or more therapeutic molecules together with one or more protease inhibitors.

The methods of the present technology, according to various embodiments, permit lower dosages and/or less frequent dosing of the bacterial mutants to be administered to a subject for prophylaxis or treatment of neoplastic disease to achieve a therapeutically effective amount of one or more therapeutic molecules. In a preferred embodiment, the genetically modified bacteria are used in animals, including humans, dogs, cats, and/or horses for protection or treatment against neoplastic diseases.

Accordingly, when administered to an individual, a live *Salmonella*, *Listeria* or *Streptococcus* bacterial vector or therapeutic, in accordance with the present technology, that is genetically engineered to express one or more anti-neoplastic molecules or molecules against other cells within the neoplastic milieu, optionally in combination with a protease inhibitor, and have improved efficacy due to improved surface display, secretion and/or released of the modified chimeric therapeutic proteins and/or enhanced binding to the target receptor resulting enhanced therapeutic activity against a neoplastic tissue including solid tumors, lymphomas and leukemias.

It is therefore an object to provide a genetic construct which causes a live host bacterium to express a peptide selected from the group consisting of at least one of: (a) a reorganized polycistronic cytolethal distending toxin fusion expressed or secreted in an absence of sty and ttsa, (b) a modified chimeric cytolethal distending toxin:apoptin fusion expressed or secreted in an absence of in an absence of sty and ttsa, and (c) a functionally active modified chimeric *Pseudomonas* ToxA therapeutic molecule. The genetic construct or bacterium may be provided in a pharmaceutically acceptable dosage form, suitable for administration to a human or animal, without causing significant morbidity. The peptide may act as an antineoplastic agent, and the bacterium may be trophic for diseased or malignant growths. The dosage form may be oral, enteral, parenteral, intravenous, per anus, topical, or inhaled, for example. The peptide may comprise a combination of at least one secretion signal, a linker, and domain Ib.

A pharmaceutically effective dosage form may comprise between about $10^5$ to $10^{12}$ live bacteria, within a lyophilized medium for oral administration. In some embodiments, about $10^9$ live bacteria are administered.

The live host bacterium may have antineoplastic activity against lymphoma, or solid tumors.

The peptide may be, for example, the modified chimeric cytolethal distending toxin:apoptin fusion with antineoplastic activity, having deletions of at least one cytolethal distending toxin nuclear localization signal. The peptide may also comprises an N-terminal fusion, e.g., of the modified chimeric cytolethal distending toxin:apoptin fusion.

Another object of the technology provides a chimeric protease inhibitor comprising YebF fused to sunflower trypsin inhibitor, adapted to inhibit at least one serine protease. The chimeric protease inhibitor may be formed by a genetically engineered bacteria, wherein the genetically engineered bacteria secretes the YebF fused to sunflower trypsin inhibitor. The chimeric protease inhibitor may be provided in combination with a host bacteria and a genetically engineered construct which encodes the chimeric protease inhibitor, wherein the host bacteria secretes the chimeric protease inhibitor and the chimeric protease inhibitor inhibits at least one serine protease.

A further object provides a method for treating neoplastic tumor cells within a living organism, comprising: administering to a human or animal a live genetically engineered bacterium expressing peptide selected from the group consisting of at least one of: (a) a reorganized polycistronic cytolethal distending toxin fusion with antineoplastic activity expressed or secreted in an absence of sty and ttsa, (b) a modified chimeric cytolethal distending toxin:apoptin fusion with antineoplastic activity expressed or secreted in an absence of in an absence of sty and ttsa, and (c) a functionally active modified chimeric *Pseudomonas* ToxA therapeutic molecule with antineoplastic activity, wherein said peptide is secreted or released by said bacterium in a functionally active form. According to one embodiment of the method, the live genetically bacterium is allowed to colonize at least one tissue of the human or animal after administration, and the human or animal is treated with at least one systemic antibiotic to which the live genetically engineered bacterium is sensitive. The antibiotic may be narrow spectrum, and indeed, may comprise a composition not generally toxic to other bacteria or animal cells.

BRIEF DESCRIPTION OF THE DRAWINGS

FIGS. 1A-1I shows a comparison of modified ToxA chimeras.

FIGS. 4A-4D show nuclear localization signal (NLS) modified cldt from *Salmonella paratyphi* A.

FIGS. 5A-5D show a secreted protease inhibition assay.

DETAILED DESCRIPTION OF THE INVENTION

Figure 2A:
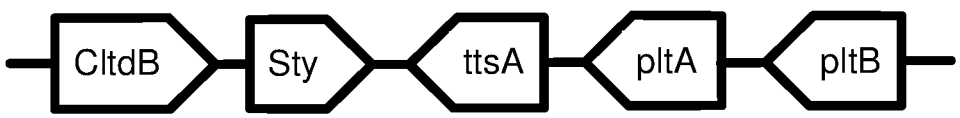
FIGS. 2A-2E show C-terminal modified cldt from *Salmonella paratyphi* A.

The present technology provides, according to various embodiments, live attenuated therapeutic bacterial strains that express one or more therapeutic with improved expression, secretion, surface display and/or release and/or have improved binding and anticancer cell activity that results in improved therapeutic efficacy. In particular, one aspect of the technology relates to live attenuated tumor-targeted bacterial strains that may include *Salmonella, Streptococcus* or *Listeria* vectoring novel chimeric anti-tumor toxins to an individual to elicit a therapeutic response against cancer. The types of cancer may generally include solid tumors, carcinomas, leukemias, lymphomas and multiple myelomas. Another aspect of the technology relates to live attenuated tumor-targeted bacterial strains that may include *Salmonella, Streptococcus, Clostridium* and *Listeria* that encode anti-neoplastic molecules to an individual to elicit a therapeutic response against cancers including cancer stem cells, immune infiltrating cells and or tumor matrix cells.

For reasons of clarity, the detailed description is divided into the following subsections: targeting ligands; chimeric bacterial toxins; and secreted protease inhibitors.

Targeting Ligands

Targeting ligands have specificity for the target cell and are used to both confer specificity to chimeric proteins, and to direct attachment and/or internalization into the target cell. The ligands are known ligands or may be novel ligands isolated through standard means such as phage display (Barbass III et al., 2004, Phage Display, A Laboratory Manual, Cold Spring Harbor Press) including the use of commercially available kits (Ph.D-7 Phage Display Library Kit, New England Biolabs, Ipswich, Mass.; Li et al., 2006. Molecular addresses of tumors: selection by in vivo phage display. Arch Immunol Ther Exp 54: 177-181,). The ligands of various aspects of the present technology are peptides that can be expressed as fusions with other bacterially-expressed proteins. The peptides may be further modified, as for gastrin and bombesin, in being amidated by a peptidylglycine-alpha-amidating monoxygenase or C-terminal amidating enzyme, which is co-expressed in the bacteria that use these peptides using standard molecular genetic techniques. Examples of targeting peptides are shown in Bermudes U.S. Pat. No. 8,524,220 Table 4, incorporated by reference herein. These ligands and their targets include TGF-α (EGFR), HAVDI and INPISGQ and dimeric versions (N-cadherin of prostate), DUP-1 peptide (prostate cancer), laminin-411 binding peptides (brain neovasculature), pertussis toxin S3 subunit (cancer cells), DARPINS (e.g., H10, HER2), affibody against Her2 (Zielenski, R., Lyakhov, I., Jacobs, A., Chertov, O., Kramer-Marek, G., Francella, N., Stephen, A., Fisher, R., Blumenthal, R., and Capala, J. Affitoxin—A Novel Recombinant, HER2-Specific, Anti-Cancer Agent for Targeted Therapy of HER2-Positive Tumors. J Immunother. 2009 October; 32(8):817-825) luteinizing hormone-releasing hormone (LHRH receptor), IL2 (IL2R), EGF and EGF receptor related peptide (EGFR), tissue factor (TfR), IL4 (IL4R), IL134 (IL13R), GM-CSF (GM-CSFR), CAYHRLRRC SEQ ID NO.: 021 (lymphoid tissue; AML), A33 antigen binding peptide (A33) CLTA-4/CD152 melanoma, CD19 binding peptides/Bpep (alpha(v) beta(6) integrin (αvβ6), non-Hodgkin lymphoma, chronic lymphocytic leukemia (CLL) and acute lymphocytic leukemia (ALL)), CD20 binding peptides (CD20, B-cell malignancies), CD22 binding peptides (B lymphocytes, hairy cell leukemia), CD25 binding peptides (chemotherapy-resistant human leukemia stem cells), TRU-015 (CD-20), CD30 binding peptides (CD-30 Hodgkin's lymphoma), CD32 binding peptides (chemotherapy resistant human leukemia stem cells), CD33 binding peptides (CD-33 AML myleodysplastic cells MDS)), CD37 binding peptides (leukemia and lymphoma), CD40 binding peptides (CD40 multiple myeloma, non-Hodgkin lymphoma, chronic lymphocytic leukemia (CLL), Hodgkin lymphoma and acute lymphoblastic leukemia (ALL), diffuse large B-cell lymphoma, refractory non-Hodgkin lymphoma, including follicular lymphoma), CD52 (CLL), CD55 (CD55R), CD70 (hematological malignancies, non-Hodgkin's lymphoma), CD123 binding peptides (AML), RGD peptides (tumor cells and tumor endothelium), nanobodies derived from camels and llamas (camelids), including humanized nanobodies and VHH recognition domains (cancer), bombesin (gastrin releasing peptide receptor), gastrin releasing peptide (gastrin releasing peptide receptor), somatostatin octapeptide RC-121 (colon cancer), vasoactive intestinal peptide (tumor cell membranes), PTHrP (parathyroid hormone receptor G-protein coupled receptor), mesothelin binding peptides (mesothelin), CA125/MUC16 (mesothelin), heat stable enterotoxin (HST) (guanylyl cyclase C), GM-CSF (AML), vitronectin (Alfa(V)Beta(3) integrin), gastrin (gastrin receptor), CQTIDGKKYYFN SEQ ID NO.: 022 peptide from Clostridium, affibody against HER3, DARPIN against HER2, TGFα, EGF, EGFR-binding peptides and other, non-limiting, peptides. In preferred embodiments, the peptides are affibody against HER2, H10 DARPIN against HER2, TGFα, EGF, EGFR-binding peptides.

FIGS. 1A-1I show a comparison of modified ToxA chimeras. Optionally, the colicin E3 lysis protein with a separate ribosomal binding site may be added to any of the constructs.

FIG. 1A shows a chimera containing an OmpA secretion signal, TGF α targeting domain, a GGGGS(×3) (i.e., GGGGSGGGGSGGGGS, SEQ ID NO.: 008 linker, ToxA domain Tb (containing cysteine bonding), ToxA domain III, followed optionally by KDEL retrograde trafficking signal; without KDEL the native signal REDLK SEQ ID NO.: 023).

FIG. 1B shows a chimera containing an OmpA secretion signal, TGFα targeting domain, a GGGGS(×3), SEQ ID NO.: 008 linker), ToxA domain III followed optionally by KDEL retrograde trafficking signal; without KDEL the native signal REDLK SEQ ID NO.: 023. Optionally, the colicin E3 lysis protein with a separate ribosomal binding site may be added.

FIG. 1C shows a chimera containing an OmpA secretion signal, TGFα targeting domain, a GGGGS(×3), SEQ ID NO.: 008 linker, ToxA PE38 (contains Domain II, partial Ib (Δ365-380 amino acids) domain III followed optionally by KDEL retrograde trafficking signal; without KDEL the native signal REDLK SEQ ID NO.: 023. Optionally, the colicin E3 lysis protein with a separate ribosomal binding site may be added.

FIG. 1D shows a chimera containing an OmpA secretion signal, EGF binding peptide (EGB), a GGGGS(×3), SEQ ID NO.: 008 linker, ToxA PE38 (contains Domain II, partial Ib (Δ365-380 amino acids) domain III followed optionally by KDEL retrograde trafficking signal; without KDEL the native signal REDLK SEQ ID NO.: 023. Optionally, the colicin E3 lysis protein with a separate ribosomal binding site may be added.

FIG. 1E shows a chimera containing an M13 pIII secretion signal, EGF binding peptide (EGB), a GGGGS(×3), SEQ ID NO.: 008 linker, ToxA PE38 (contains Domain II, partial Ib (Δ365-380 amino acids) domain III followed optionally by KDEL retrograde trafficking signal; without KDEL the native signal REDLK SEQ ID NO.: 023. Optionally, the colicin E3 lysis protein with a separate ribosomal binding site may be added.

FIG. 1F shows a chimera containing an OmpA secretion signal, Her2 affibody binding, a GGGGS linker, ToxA PE38 (contains Domain II, partial Ib (Δ365-380 amino acids) domain III followed optionally by KDEL retrograde trafficking signal; without KDEL the native signal REDLK SEQ ID NO.: 023.

FIG. 1G shows a chimera containing an OmpA secretion signal, Her2 affibody binding, a GGGGS(×3), SEQ ID NO.: 008 linker, ToxA PE38 (contains Domain II, partial Ib (Δ365-380 amino acids) domain III followed optionally by KDEL retrograde trafficking signal; without KDEL the native signal REDLK SEQ ID NO.: 023.

FIG. 1H shows a chimera containing an OmpA secretion signal, Her2 affibody, a GGGGS(×3) linker, ToxA domain Ib (containing cysteine bonding), ToxA domain III followed optionally by KDEL retrograde trafficking signal; without KDEL the native signal REDLK SEQ ID NO.: 023.

FIG. 1I shows a chimera containing an OmpA secretion signal, EGFR binding peptide, a GGGGS(×3), SEQ ID NO.: 008 linker, ToxA domain Ib (containing cysteine bonding), ToxA domain III followed optionally by KDEL retrograde trafficking signal; without KDEL the native signal REDLK SEQ ID NO.: 023.

Chimeric Bacterial Toxins

Chimeric toxins are toxins that may contain combinations of elements including targeting peptides, flexible linkers, disulfide bonding, lytic peptides, nuclear localization signals, blocking peptides, protease cleavage (deactivation or activation) sites, N- or C-terminal secretion signals, autotransporter constructs, used to adapt the proteins to be expressed, secreted, surface displayed and/or released by bacteria to provide therapeutic molecules that are effective in treating neoplastic cells, stromal cells, neoplastic stem cells as well as immune infiltrating cells. Targeting to a particular cell type uses the appropriate ligand described above or from other known sources. Toxin activity is determined using standard methods known to those skilled in the art such as Aktories (ed) 1997 (Bacterial Toxins, Tools In Cell Biology and Pharmacology, Laboratory Companion, Chapman & Hall).

FIGS. 2A-2D show C-terminal fusions of modified cldt from *Salmonella paratyphi* A.

FIG. 2A shows the *Salmonella* typhoid toxin cytolethal distending toxin subunit B (cldtB) together with sty, ttsA, pltA and pltB. The entire operon is with cldtB and sty under control of an inducible promoter such as the arabinose inducible promoter, with pltB, pltA and ttsA under control of their upstream region.

Figure 2B:

FIG. 2B shows the *Salmonella* typhoid toxin cytolethal distending toxin subunit B (cldtB) together with pltB and pltA as a single artificial operon under control of an inducible promoter, and the genes sty and ttsA removed.

Figure 2C:
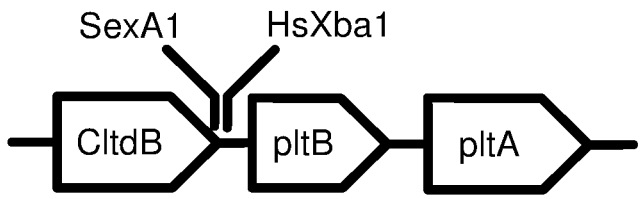

FIG. 2C shows the cldtB, pltB and pltA artificial operon with an in frame fusion of the restriction enzymes SexAl, HindIII and Xbal followed by a stop codon.

Figure 2D:
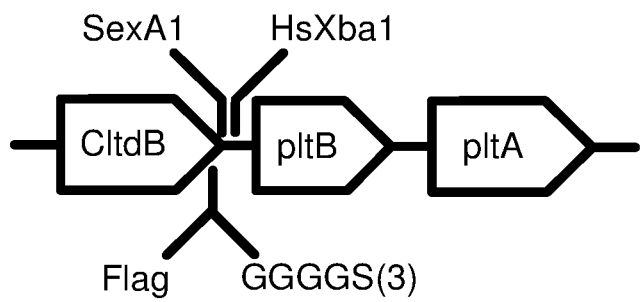

FIG. 2D shows the cldtB, pltB and pltA artificial operon with SexAl, HindIII and Xbal with the FLAG epitope and a GGGGS(x3), SEQ ID NO.: 008 linker inserted in the SexAl and HindIII sites.

Figure 2E:
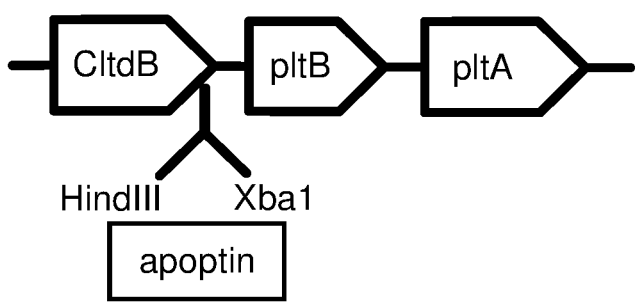

FIG. 2E shows the cldtB, pltB and pltA artificial operon with SexAl, HindIII and Xbal with the FLAG epitope and a GGGGS(x3), SEQ ID NO.: 008 linker inserted in the SexAl and HindIII sites and apoptin fragments inserted in-frame into the HindIII and Xbal sites. The apoptin and/or apoptin fragments can consist of 1) apoptin 1-121, 2) apoptin 33-121, 3) apoptin 82-121, 4) apoptin 97-121, 5) apoptin 106-121, 6) apoptin 111-121 or 7) apoptin 1-31 linked ot 83-121 or 8) TAT-apoptin.

Chimeric ToxA Forms Secreted by Bacteria.

Cytotoxic forms of ToxA that can be secreted by bacteria have targeting ligands. Previous ToxA conjugates were not adapted for secretion by bacteria in an active form. For example, TGFα-GIII-KDEL (Kihara and Pastan 1994, Small Chimeric Toxins Containing Only Transforming Growth Factor α and Domain III of *Pseudomonas* Exotoxin with Good Antitumor Activity in Mice. Cancer Res 1994: 54:5154-5159) had a TGFα α-PE38 which has a deletion of amino acids 365-380 of domain I (Kreitman et al., 1992, Properties of Chimeric Toxins with Two Recognition Domains: Interleukin 6 and Transforming Growth Factor α at Different Locations in *Pseudomonas* Exotoxin. Bioconjugate Chem. 3, 63-68) have no signal peptide, only a single GGGGS linker with 10 amino acids upstream of DM, compared to the present version (FIGS. 1A-1I). PE38-KDEL (Kreitman et al., 1994, Recombinant immunotoxins containing anti-Tac(Fv) and derivatives of *Pseudomonas* exotoxin produce complete regression in mice of an interleukin 2 receptor-expressing human carcinoma. Blood 1994, 83, 426-434) uses anti-Tac (Fv) as binding ligand rather than those we describe here. Similarly, the Affitoxin (Zielenski et al., 2009, Affitoxin—A Novel Recombinant, HER2-Specific, Anti-Cancer Agent for Targeted Therapy of HER2-Positive Tumors. J Immunother 32: 817-825) has no signal peptide and only a short flexible linker. The forms of ToxA shown in FIGS. 1A-1I and described in the examples with targeting moieties supply the necessary components for secreted by bacteria and are cytotoxic for cancer cells.

FIGS. 3A-3D show N-terminal fusions of modified cldt from *Salmonella paratyphi* A.

Figure 3A:
FIG. 3A-3D show N-terminal modified cldt from *Salmonella paratyphi* A.

FIG. 3A shows the *Salmonella* typhoid toxin cytolethal distending toxin subunit B (cldtB) together with pltB and pltA as a single artificial operon under control of an inducible promoter, and the genes sty and ttsA removed. The presence and relative location of an N-terminal signal sequence (SS) is shown.

Figure 3B:
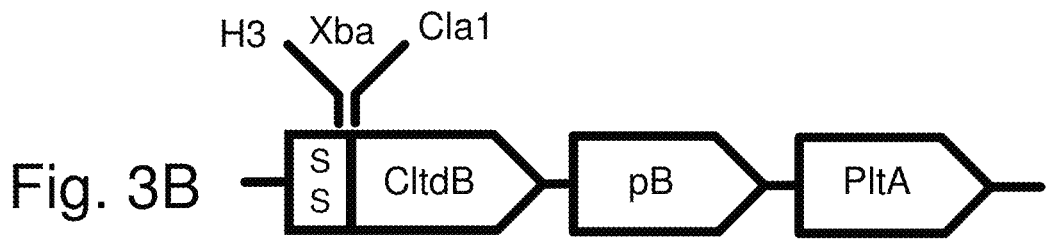

FIG. 3B shows the cldtB, pltB and pltA artificial operon with an in frame fusion of the restriction enzymes HindIII, Xbal and Clal inserted after the signal sequence.

Figure 3C:
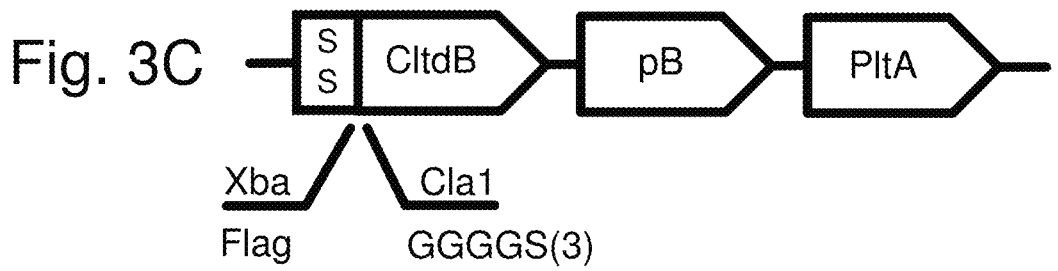

FIG. 3C shows the cldtB, pltB and pltA artificial operon with HindIII, Xbal and Clal with the FLAG epitope and a GGGGS(x3), SEQ ID NO.: 008 linker inserted in the Xbal and Clal sites.

Figure 3D:
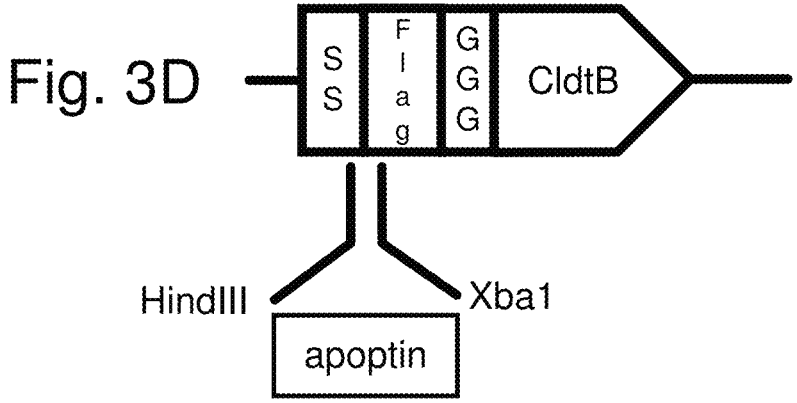
Figure 6:
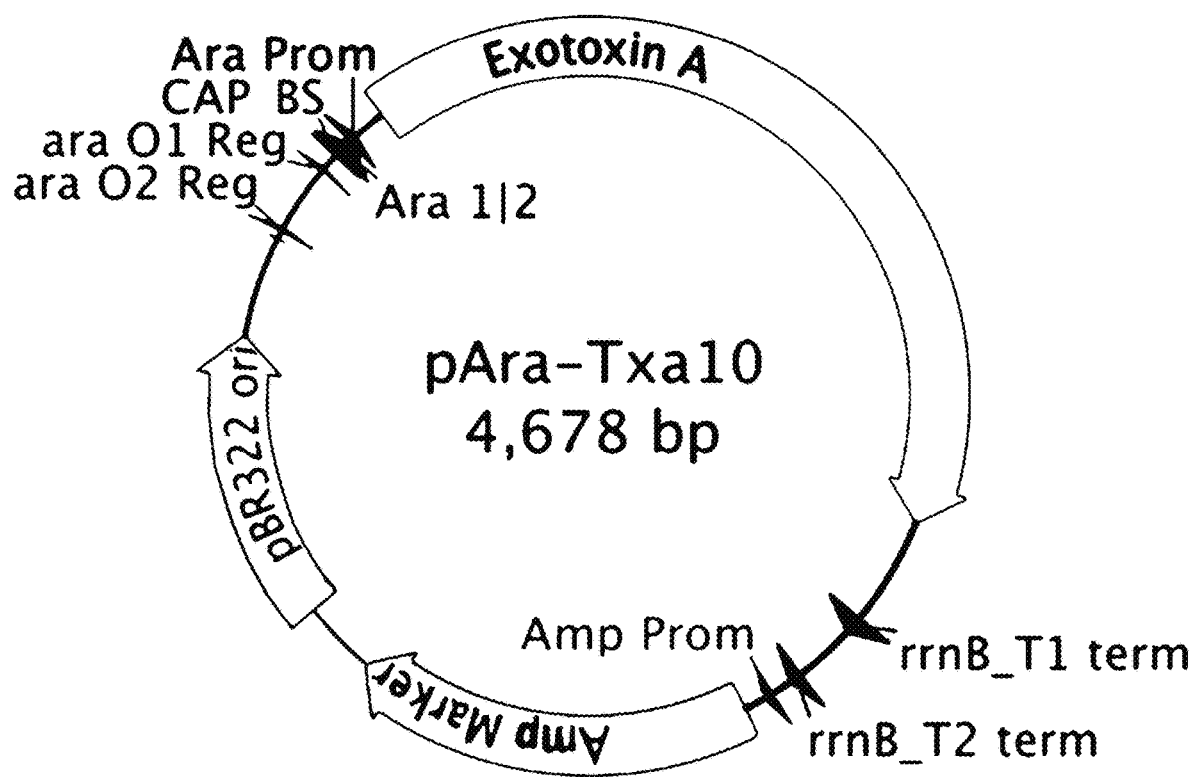
FIG. 6 shows a pAra-Txa10 4,678 bp plasmid.
Figure 7A:
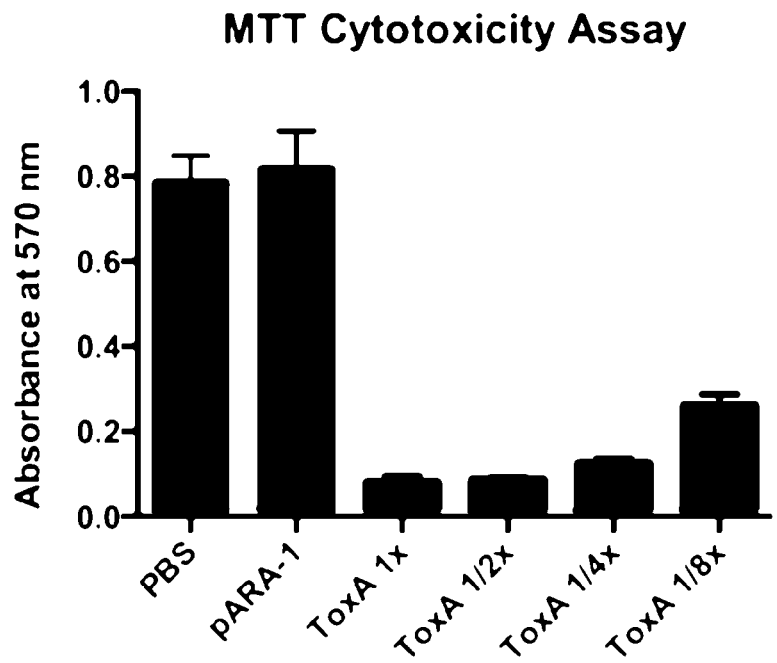
FIGS. 7A and 7B show results of MTT cytotoxicity (anticancer cell killing) assay of protease challenge/protease inhibitors.
Figure 7B:
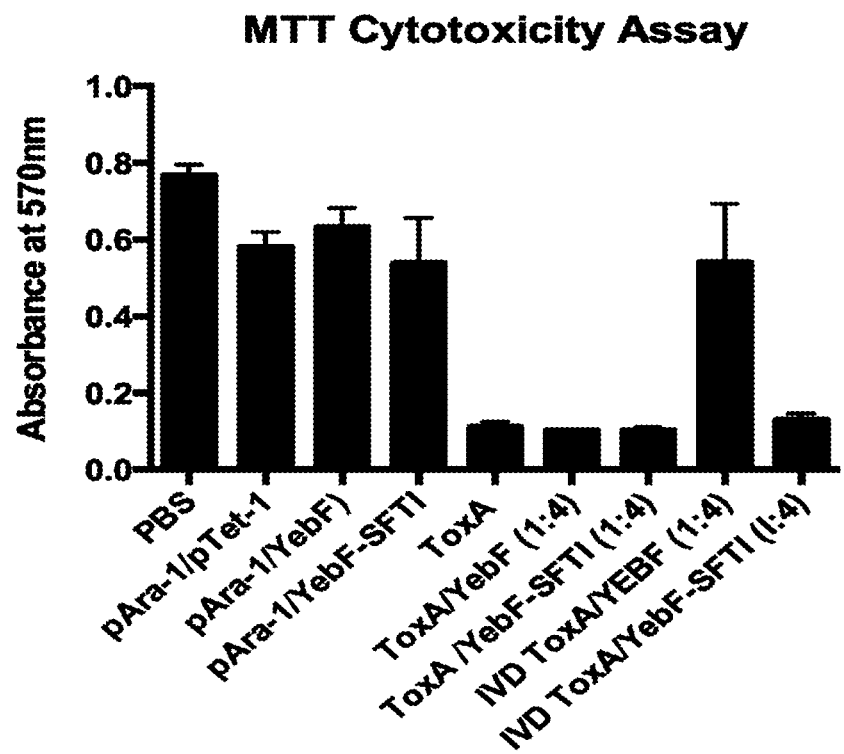

FIG. 3D shows the cldtB, pltB and pltA artificial operon with the FLAG epitope and a GGGGS(x3), SEQ ID NO.: 008 linker inserted in the Xbal and Clal sites and apoptin fragments inserted in-frame into the HindIII and Xbal sites. The apoptin and/or apoptin fragments can consist of 1) apoptin 1-121, 2) apoptin 33-121, 3) apoptin 82-121, 4) apoptin 97-121, 5) apoptin 106-121, 6) apoptin 111-121 or 7) apoptin 1-31 linked to 83-121 or 8) TAT-apoptin.

Chimeric Cytolethal Distending Toxins.

Cytolethal distending toxins (cldt) including those cldts from *Haemophilus, Aggregatibacter, Salmonella, Escherichia, Shigella, Campylobacter, Helicobacter, Hahella* and *Yersinia*, typhoid toxins (pertussis like toxin) (pltAB), pertussis toxin, cldt:plt hybrids are three component toxins of these bacteria. Cldt is an endonuclease toxin and has a nuclear localization signal on the B subunit. Chimeric toxins are provided that utilize N-terminal or C-terminal fusions to apoptin, a canary virus protein that has a tumor-specific nuclear localization signal, and a normal (non-transformed) cell nuclear export signal (FIGS. 2A-4D). The present technology, according to one embodiment, consists of a modified *Salmonella* CLDT operon and forms of cytolethal distending toxins that are chimeric with apoptin and other peptide moieties including peptide linkers that improve activity and peptide blocking moieties that must be specifically cleaved to activate the protein.

The present technology, according to one embodiment, uses deletions in the CLDT nuclear localization signals which are then complemented by N- or C-terminal fusions with apoptin, or apoptin fragments, which supply its nuclear localization signal in trans as a fusion peptide.

The cytolethal distending toxin B and chimeric cltdB may be expressed as a polycistronic construct consisting of cldtABC. The cytolethal distending toxin B and chimeric cltdB may be expressed as a polycistronic construct consisting containing the typhoid pertussis-like toxin (plt) AB genes. However, in the present technology, according to one embodiment, the presence of sty and ttsA are not required for secretion of the active toxin when the operon is reorganized into a unidirectional operon of cldtB, pltB and pltA.

Overall improvement is defined as an increase in effect, such as the ability to kill a neoplastic cells in vitro by the bacteria, or inhibit or reduce the volume or cell number of a solid tumor, carcinoma, lymphoma or leukemia in vivo following administration with the bacteria expressing a therapeutic molecule, with and without the protease inhibitor. The effect of the protein therapeutic activity is determined using standard techniques and assays known to those skilled in the art. The contribution of the therapeutic protein and protease inhibitors is determined individually and in combination. Additivity, synergy or antagonism may be determined using the median effect analysis (Chou and Talaly 1981 Eur. J. Biochem. 115: 207-216) or other standard methods.

FIGS. 4A-4D show nuclear localization signal (NLS) modified partially or completely cldt from *Salmonella paratyphi* A.

FIG. 4A shows inactivated *Salmonella paratyphi* A typhoid toxin as a delivery mechanism for peptide fusions. The *Salmonella* typhoid toxin cldtB is inactivated by site-directed mutagenesis of the known active sites such as H160Q and/or H259Q. Fusions to the inactivated form retain the secretion and delivery to the cytosol and allow transport to the nucleus.

FIG. 4B shows inactivated *Salmonella paratyphi* A typhoid toxin nuclear localization signals (NLS1) enhancing dependence on apoptin NLSs and/or nuclear export as a mode of tumor cell-specific delivery of an active cldtB.

FIG. 4C shows inactivation of NLS2 and

FIG. 4D shows both portions of the cldtB bipartite nuclear localization signals can be altered from charged (basic) e.g., arginines and/or histidines to polar serines or threonines.

Secreted Protease Inhibitors

A chimeric protease inhibitor secreted by *Escherichia coli* with the potential for use in biofuel fermentations and therapeutic bacteria is provided.

There is growing interest in the use of live bacteria targeting solid tumors as an alternative to or in conjunction with standard chemotherapy and radiation treatment. These bacteria can be engineered to secrete bacterial derived cytotoxins, such as *Pseudomonas aeruginosa* exotoxin A, directly to the site of the tumor (Forbes, 2010 and Swofford et al, 2014). Therapeutic bacteria expressing and secreting cytotoxins that are tumor cell specific may enhance tumor destruction and spare healthy adjacent tissues (Siegal et al, 1989). Bacteria expressing protease inhibitors specific for proteases associated with metastasis is an innovative approach to cancer therapeutics. Co-expression of a tumor specific cytotoxin and a protease inhibitor may enhance the stability of the toxin by protecting it in the highly proteolytic environment of the tumor while confining the cancer.

From a bio-industrial standpoint, fermentations which are sensitive to bacterial contaminations, especially those due to proteolytic strains such as *Lactobacillus* sp., may benefit from protease inhibition. Bacteria and fungi secreting protease inhibitors offer a potential augmentation to extracellular fermentations such as cellulosic ones used in the production of biofuels where microbial contaminations reduce production efficiency.

Protease inhibitor-secreting bacteria have an ability to protect extracellular proteins from proteolytic destruction by trypsin, utilizing exotoxin A in cytotoxicity studies and $\alpha$-amylase as a model industrial extracellular fermentation enzyme.

FIGS. 5A-5D show results of a secreted protease inhibition assay for detection of bacterial secreted protease inhibitors, using the method of Quintero and Bermudes (2014. A culture-based method for determining the production of secreted protease inhibitors. J. Micro. Methods. 100, 105-110).

FIG. 5A shows growth pattern of *E. coli* harboring 1) pTet-1 (EV), 2) pTetOmpA-SFTI, 3) pTetTxA-SFTI, 4) pTetOmpA-SFTI-RBS Lys, 5) pTetTxA-SFTI-RBS Lys on BCG 0.5% Casein induced with 1 μg/mL anhydrotetraclyine HCl after 24 hours at 37° C.

FIG. 5B shows staining pattern of protected protein, using the method of Quintero and Bermudes (2014. A culture-based method for determining the production of secreted protease inhibitors. J. Micro. Methods. 100, 105-110).

FIG. 5C shows growth of *E. coli* harboring 1) pTet-1 (EV), 2) pTetYebF, 3) pTetYebF-SFTI, on BCG 0.5% Casein with 1 mg/mL anhydrotetraclyine HCl after 24 hours at 37° C.

FIG. 5D shows a staining pattern of protected protein.

FIG. 6 shows the gene encoding exotoxin A, which was amplified from *Pseudomonas aeruginosa* str. PA103 in a colony PCR and ligated to pAra-1 to create pAra-Txa10. The plasmids were electroporated into *Salmonella typhimurium* str. JR501 and induced with 0.1% arabinose. Filter sterile supernatant was diluted 2-fold in PBS. MDA-MB-468 breast cancer cells were plated at 2.5×103 cells in DMEM with 10% FBS and allowed to adhere to a 96-well plate for 24 hours. Bacterial supernatant or PBS was delivered to the cell culture to 10% and allowed to incubate for an additional 72 hours.

The sunflower trypsin inhibitor (SFTI), a 14 amino acid cyclic peptide was chosen for its small size and ability to inhibit matriptase, a tumor associated protease over-expressed in cancers of the breast, ovaries, prostate and liver. (Cai et al, 2011). SFTI was fused to the secretion signal peptides derived from the outer membrane protein OmpA and the secreted cytotoxin exotoxin A and evaluated for its ability to be secreted extracellularly and to inhibit degradation of a protein substrate. These constructs were coupled with the pColE3 lysis protein, which activates phospholipase and outer-membrane porins to facilitate secretion. SFTI was also fused to YebF, which is known to accumulate in the extracellular milieu of select proteobacteria.

Therefore, it can be seen that SFTI can be secreted in low amounts when fused to a type II secretion signal peptide. Co-expression of pColE3 lysis protein with the fusions enhances secretion when the OmpA signal is utilized, but not the Exotoxin A signal. This may be due to ineffective cleavage of the latter in the periplasm. Fusion of SFTI to YebF demonstrated high protease inhibition both in solid and liquid culture media. We were able to show the protective effect of YebF-SFTI by conducting an in vitro digest of Exotoxin A followed by a cytotoxity assay, which demonstrated sustained toxin activity. An in vitro digest of amylase followed by DNS assay showed only slight inhibition of trypsin by YebF-SFTI for unknown reasons.

FIG. 7A shows cytotoxicity (anticancer cell killing) protease challenge/protease inhibitor assay results, in particular protection of extracellular ToxA from trypsin by YebF-SFTI assessed by cell killing. MDA-MB-468 breast cancer cells assessed by MTT after supernatants from *S. typhimurium* harboring pAra-1 was mixed with supernatants from *E. coli* harboring pTet-1 (EV), pTetYebF, or pTetYebf-SFTI then delivered to the cell culture. A 1:4 (vol:vol) mixture of supernatant containing exotoxin A and either YebF or YebF-SFTI was prepared and delivered to the cell culture. A seven hour in vitro digest (IVD) at 37° C. utilizing trypsin at a final concentration of 0.1 mg/ml containing exotoxin A and either YebF or YebF-SFTI (1:4) was conducted to test if the secreted protein maintained measurable activity.

FIG. 7B shows protection of extracellular ToxA from trypsin by YebF-SFTI assessed by cell killing. MDA-MB-468 breast cancer cells were plated as above, and assessed by MTT after Supernatants from *S. typhimurium* harboring pAra-1 was mixed with supernatants from *E. coli* harboring pTet-1 (EV), pTetYebF, or pTetYebf-SFTI then delivered to the cell culture. A 1:4 (vol:vol) mixture of supernatant containing exotoxin A and either YebF or YebF-SFTI was prepared and delivered to the cell culture. A seven hour in vitro digest (IVD) at 37° C. utilizing trypsin at a final concentration of 0.1 mg/ml containing exotoxin A and either YebF or YebF-SFTI (1:4) was conducted to test if the secreted protein maintained measurable activity.

See: Forbes, N. S., 2010. Engineering the perfect (bacterial) cancer therapy. Nature Reviews Cancer 10, 785-794; Swofford, C., St. Jean, A. T., Panteli, J. T., Brentzel, Z. J., Forbes, N. S. 2014. Identification of *Staphylococcus aureus* $\alpha$-hemolysin as a Protein Drug that is Secreted by Anticancer Bacteria and Rapidly kills Cancer Cells. Biotech. Bioeng. 111, 1233-1245; Siegall, C., Yong-Hua, X., Vijay, K. C., Sankar, A., Fitzgerald, D., and Pastin, I. 1989. Cytotoxic activities of a fusion protein comprised of TGFα and *Pseudomonas* exotoxin. FASEB. J. 3, 2547-2652; Quintero, D. and Bermudes, D. 2014. A culture-based method for determining the production of secreted protease inhibitors. J. Micro. Methods. 100, 105-110.

See also Examples 12-14.

Figure 8A:
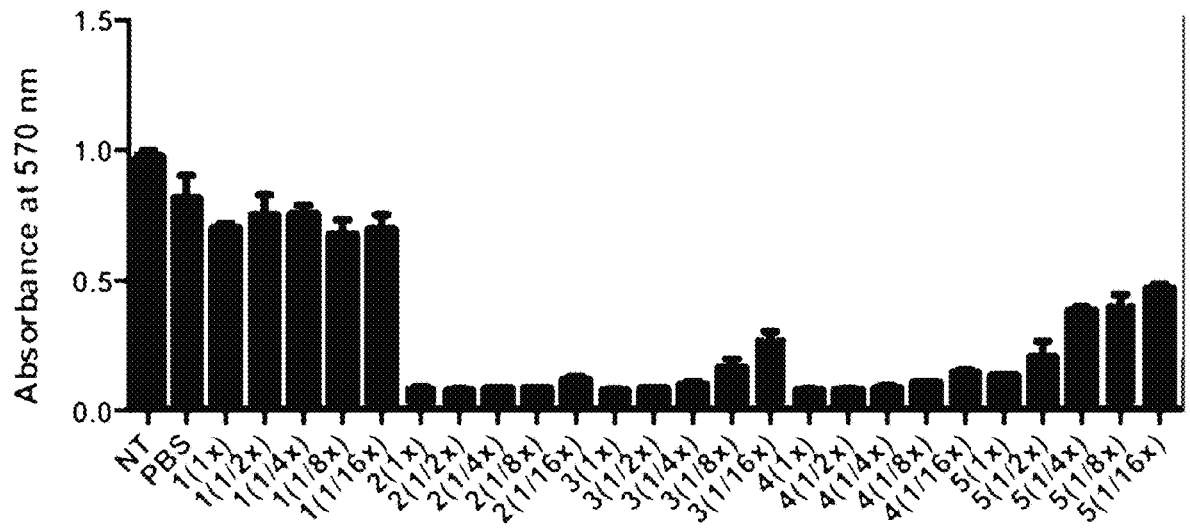
FIGS. 8A and 8B show results of a cytotoxicity (anticancer cell killing) assay of cytolethal distending toxin and cytolethal distending toxin:apoptin fusions.
Figure 8B:
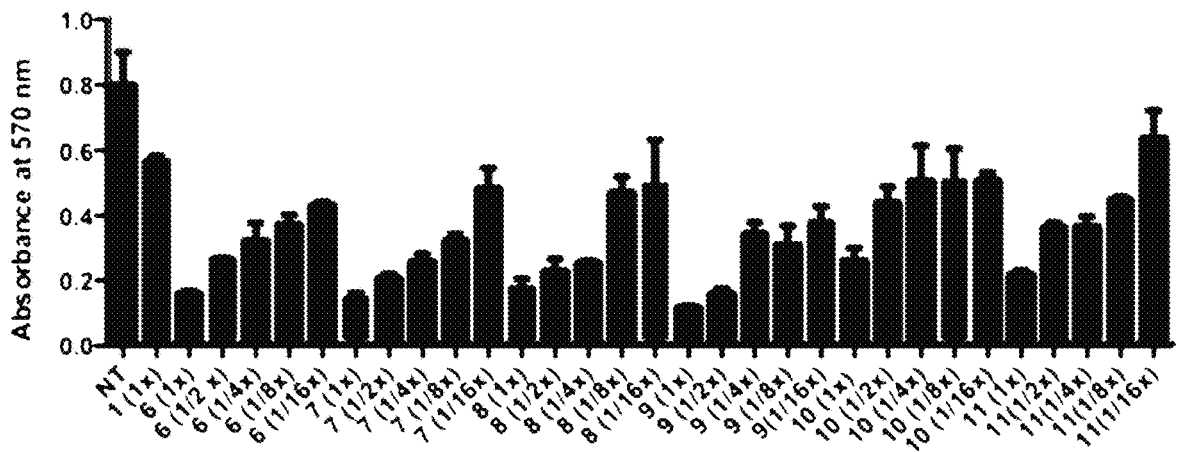
Figure 9:
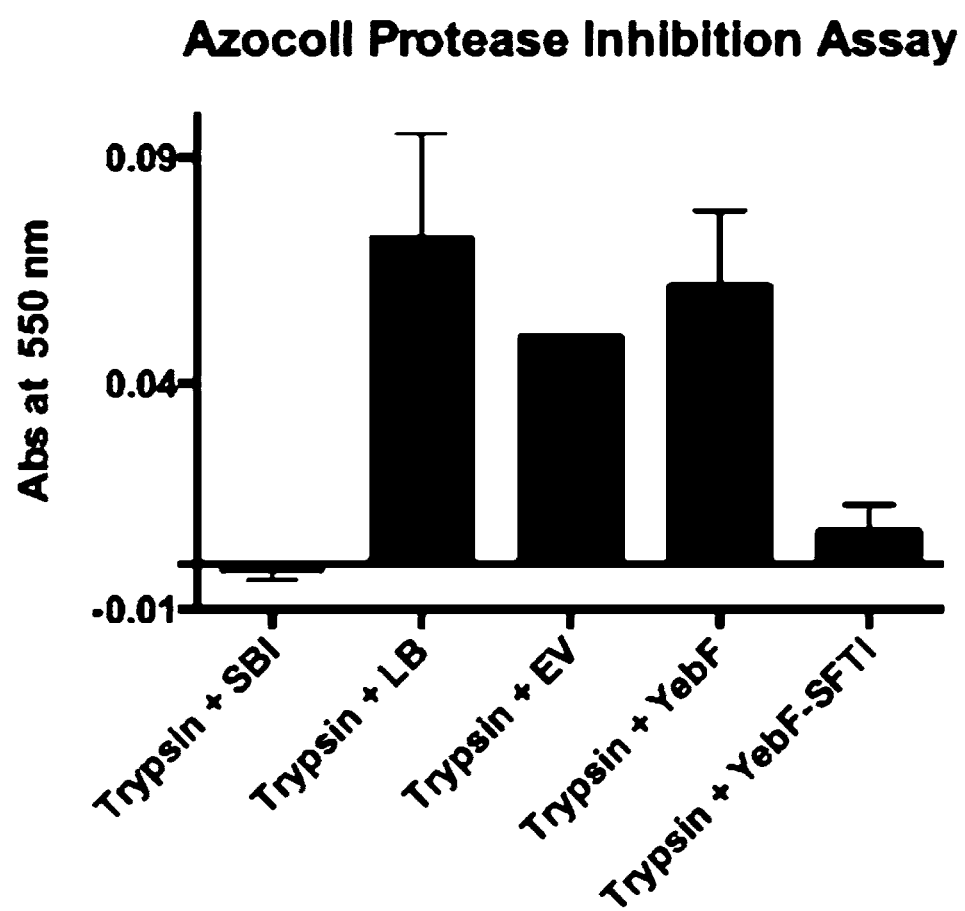
FIG. 9 shows results of an Azocoll protease inhibition assay.
Figure 10A:
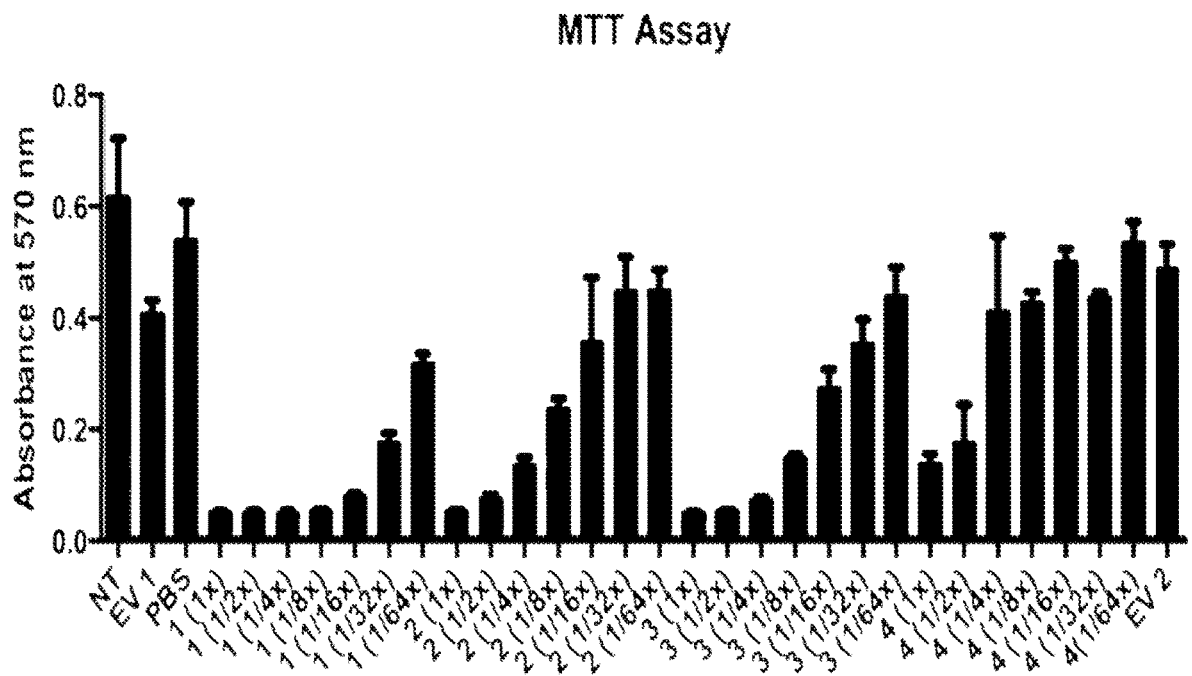
FIGS. 10A and 10B show a cytotoxicity (anticancer cell killing) assay of Exotoxin A (ToxA) and chimeric TGFα-ToxA fusions.
Figure 10B:
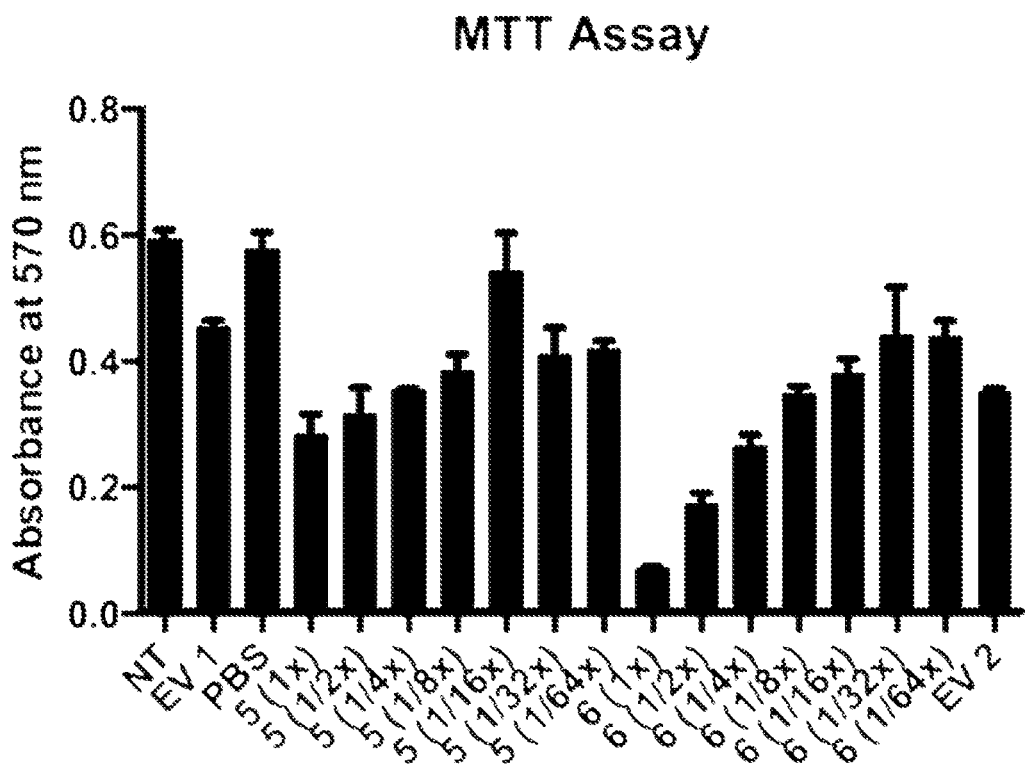
Figure 11A:
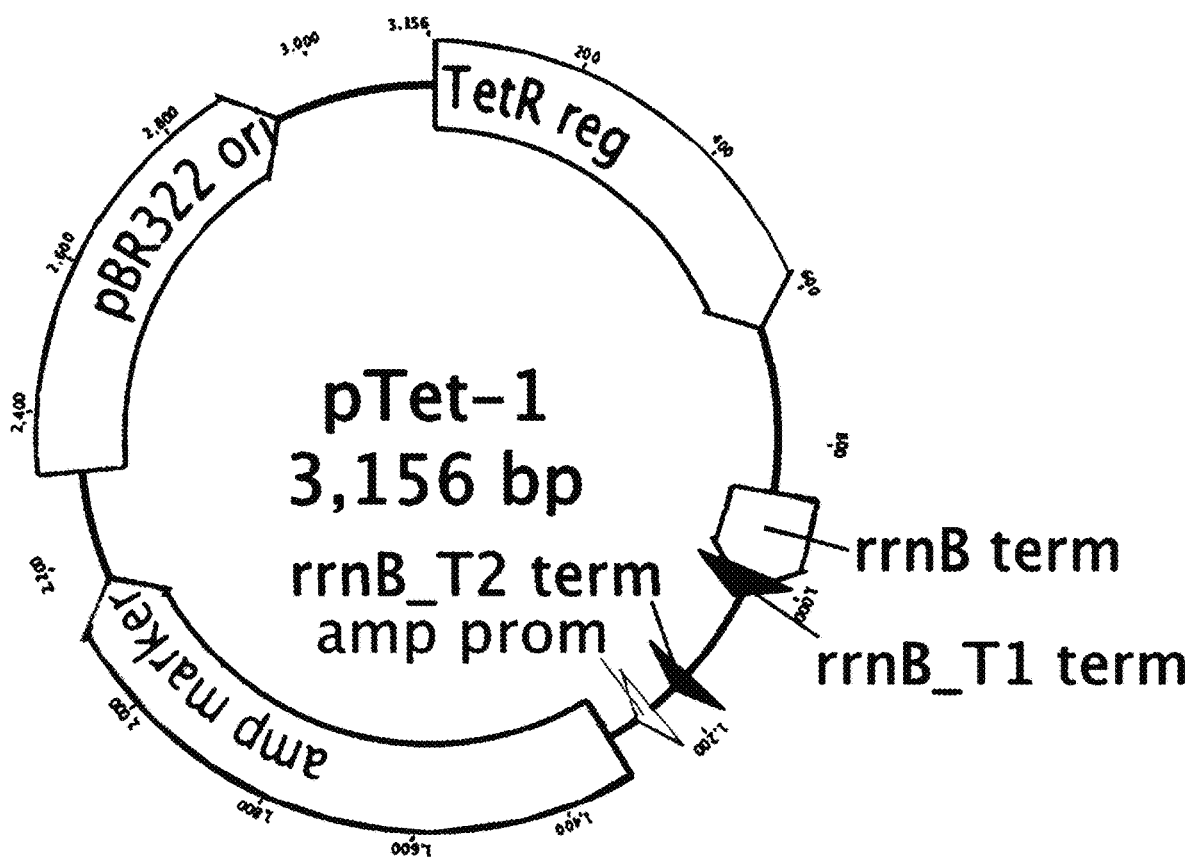
FIGS. 11A and 11B shows a pTet-1 3,156 plasmid, and pTet-1 under tetracycline controlled transcriptional activation.
Figure 11B:
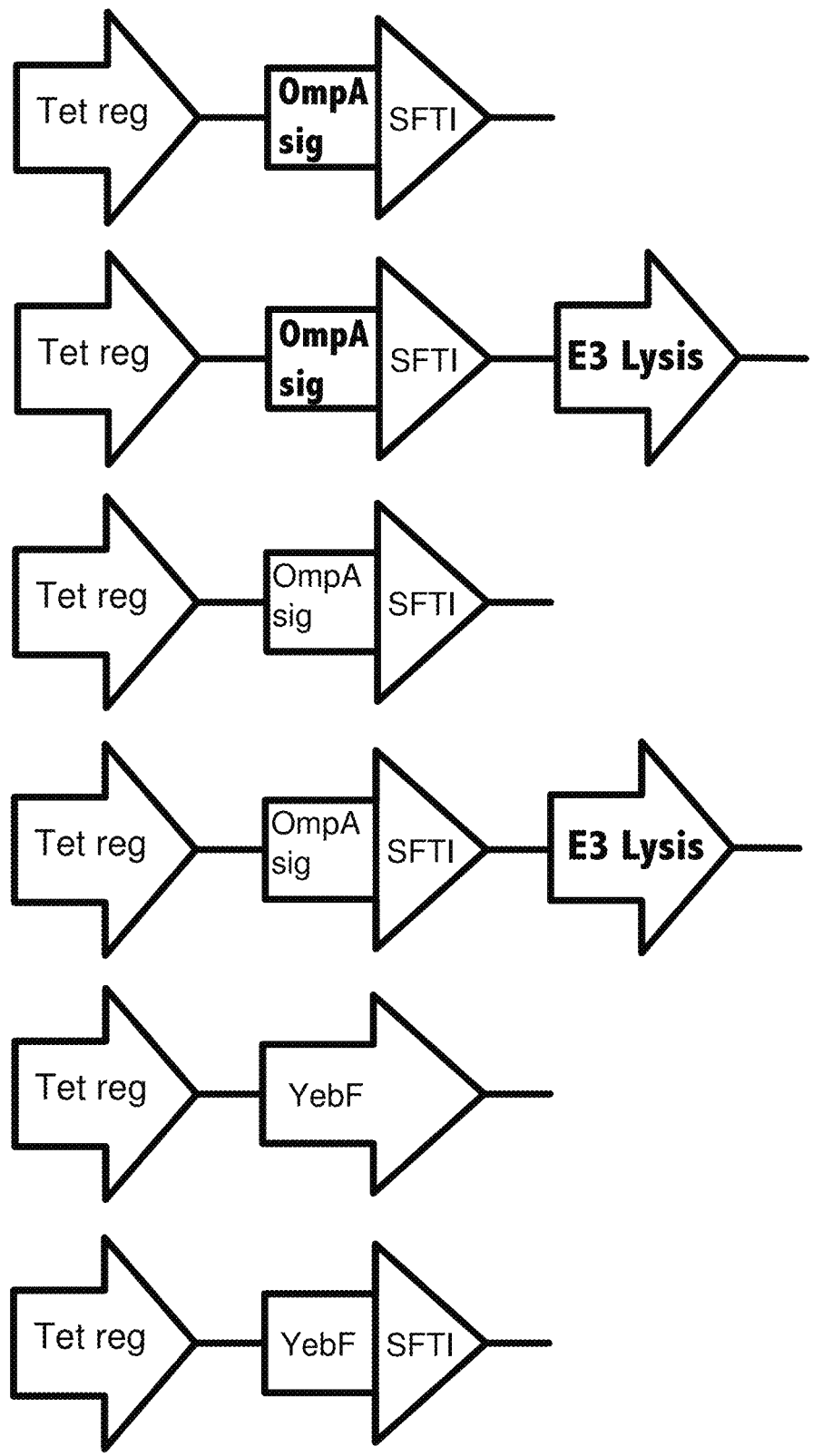
Figure 12:
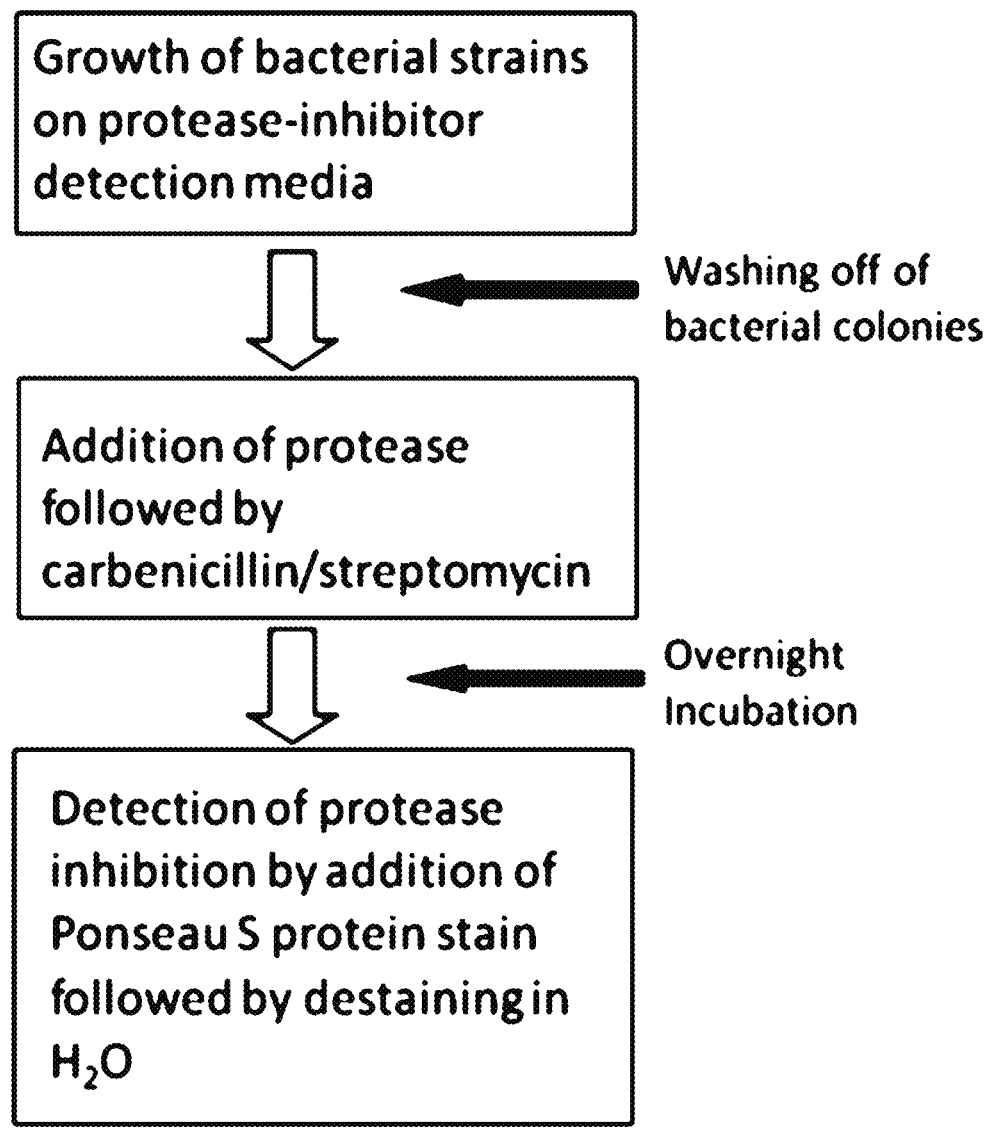
FIG. 12 shows a flowchart of a method for detection of protease inhibitory activity on protein based plates.
Figure 13:
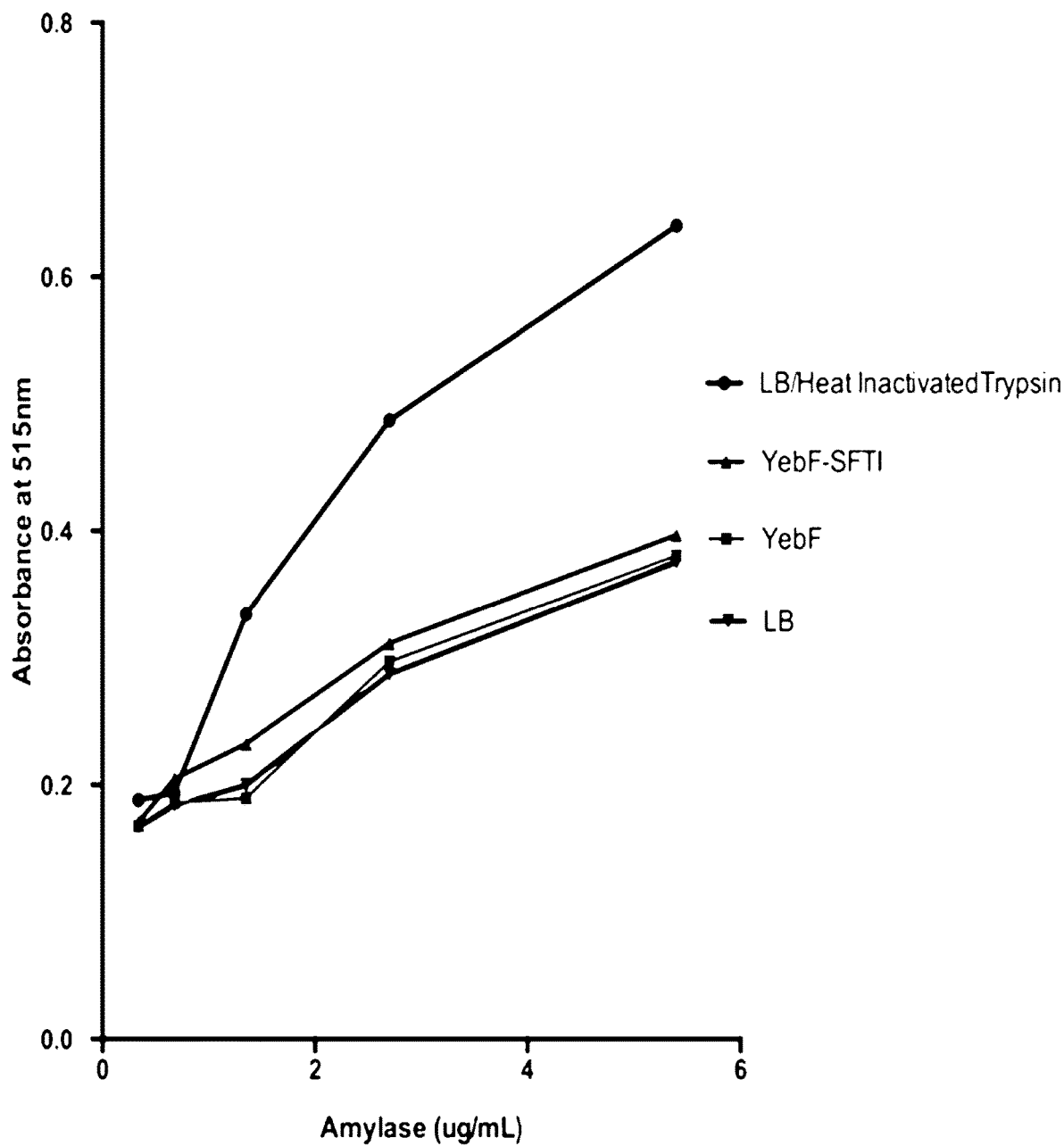
FIG. 13 shows Dinitrosalicylic Acid (DNS) assay for the detection of reducing sugars produced by active amylase under a trypsin challenge.

FIGS. 8A and 8B show results of a cytotoxicity (anticancer cell killing) assay of *Salmonella paratyphi* A cytolethal distending toxin and cytolethal distending toxin:apoptin fusions toward MDA-MB-468 breast cancer cells.

NT: no treatment.

PBS: phosphate buffered saline.

1: treatment with 10 μL of a bacterial culture supernatant carrying an empty vector plasmid into a 100 μL tissue culture wells, with dilutions of 1, ½, ¼, ⅛ and 1/16.

2: the cloned wild type *S. paratyphi* A cytolethal distending operon (as shown in FIGS. 2A-2E), with dilutions of ½, ¼, ⅛ and 1/16.

3: the reorganized polycistronic *S. paratyphi* A cytolethal distending operon containing a polylinker in cldtB C-terminus with dilutions of ½, ¼, ⅛, and 1/16.

4: the reorganized polycistronic *S. paratyphi* A cytolethal distending operon without a polylinker in cldtB C-terminus with dilutions of ½ ¼ ⅛ and 1/16. Absorbance at 570 nm indicates the relative number of live cells.

5: the reorganized polycistronic *S. paratyphi* A cytolethal distending operon containing a polylinker in cldtB C-terminus and a flexible linker GGGGS(3) SEQ ID NO.: 008 with dilutions of ½, ¼, ⅛, and 1/16.

6: the reorganized polycistronic *S. paratyphi* A cytolethal distending operon containing a polylinker in cldtB C-terminus and a fusion of apoptin 1-121 with dilutions of ½, ¼, ⅛, and 1/16.

7: the reorganized polycistronic *S. paratyphi* A cytolethal distending operon containing a polylinker in cldtB C-terminus and a fusion of apoptin 82-121 with dilutions of ½, ¼, ⅛ and 1/16.

8: the reorganized polycistronic *S. paratyphi* A cytolethal distending operon containing a polylinker in cldtB C-terminus and a fusion of apoptin 111-121 with dilutions of ½, ¼, ⅛ and 1/16.

9: the reorganized polycistronic *S. paratyphi* A cytolethal distending operon containing a polylinker in cldtB C-terminus and a fusion of apoptin 97-121 with dilutions of ½, ¼, ⅛ and 1/16.

10: the reorganized polycistronic *S. paratyphi* A cytolethal distending operon containing a polylinker in cldtB C-terminus and a fusion of apoptin 33-121 with dilutions of ½, ¼, ⅛ and 1/16.

11: the reorganized polycistronic *S. paratyphi* A cytolethal distending operon containing a polylinker in cldtB C-terminus and a fusion of TAT:apoptin 1-121 with dilutions of ½, ¼, ⅛ and 1/16.

FIG. 9 shows results of an assay using Azo dye impregnated collagen (Azocoll) protease substrate. *E. coli* harboring pTet-1 (EV), pTetYebF, or pTetYebF-SFTI, were induced overnight. 500 μL of filter sterile supernatant was incubated with 10 mL of 6.25 mg/mL trypsin solution for 1 hour at room temperature to allow binding. Soybean inhibitor (SBI) and LB served as controls. After equilibration, 400 mL of a 1.5 mg/mL Azocoll suspension was mixed with each sample and incubated at 37° C. for a 2 hour digestion. Proteolytic degradation of Azocoll was measured with a spectrophotometer at Abs 550 nm. After subtracting background, the absorbance values were plotted using Prism version 6.

FIGS. 10A and 10B show the cytotoxicity of *Pseudomonas aeruginosa* Exotoxin A (ToxA) and chimeric derivatives toward MDA-MB-468 breast cancer cells.

FIG. 10A:

NT: no treatment. PBS, phosphate buffered saline.

EV 1: treatment with 10 μL of a bacterial culture supernatant carrying an empty vector plasmid into a 100 μL tissue culture wells.

1: the cloned wild type *Pseudomonas aeruginosa* Exotoxin A (ToxA) with dilutions of 1, ½, ¼, ⅛, 1/16, 1/32, 1/64.

2: A chimeric toxin composed of N-terminal TGFα fused to domains Ib and III of ToxA with a C-terminal KDEL sequence with dilutions of 1, ½, ¼, ⅛, 1/16, 1/32, 1/64.

3: A chimeric toxin composed of N-terminal TGFα fused to domains Ib and III of ToxA with a C-terminal KDEL sequence co-expressed with the RBS E3 Lysis protein with dilutions of 1, ½, ¼, ⅛, 1/16, 1/32, 1/64.

4: A chimeric toxin composed of N-terminal TGFα fused to domains Ib and III of ToxA with the native C-terminal REDLK SEQ ID NO.: 023 ToxA sequence with dilutions of 1, ½, ¼, ⅛, 1/16, 1/32, 1/64.

EV 2: empty vector plasmid.

FIG. 10B:

NT: no treatment. PBS, phosphate buffered saline.

EV 1: treatment with 10 μL of a bacterial culture supernatant carrying an empty vector plasmid into a 100 μL tissue culture wells.

1: the cloned wild type *Pseudomonas aeruginosa* Exotoxin A (ToxA) with dilutions of 1, ½, ¼, ⅛, 1/16, 1/32, 1/64.

2: A chimeric toxin composed of N-terminal TGFα fused to domain III of ToxA with a C-terminal KDEL sequence with dilutions of 1, ½, ¼, ⅛, 1/16, 1/32, 1/64.

3: A chimeric toxin composed of N-terminal TGFα fused to domain III of ToxA with a C-terminal KDEL sequence co-expressed with the RBS E3 Lysis protein with dilutions of 1, ½, ¼, ⅛, 1/16, 1/32, 1/64.

4: A chimeric toxin composed of N-terminal TGFα fused to domains Ib and III of ToxA with the native C-terminal REDLK SEQ ID NO.: 023 ToxA sequence with dilutions of 1, ½, ¼, ⅛, 1/16, 1/32, 1/64.

EV 2: empty vector plasmid.

FIGS. 11A and 11B show pTet-1 under tetracycline controlled transcriptional activation (FIG. 11A), and insertion sequences downstream from the tetracycline repressor sequence (FIG. 11B). The sunflower trypsin inhibitor DNA sequence was fused to the signal peptide sequences derived from OmpA and Exotoxin A and ligated to pTet-1. The pColE3 lysis sequence, including its Shine-Delgarno sequence was cloned into pTetOmpA-SFTI and pTetTxA-SFTI. The YebF sequence was cloned into pTet-1 to create pTet-YebF. The SFTI sequence was fused in frame with YebF to produce pTetYebF-SFTI. All constructs were verified by sequencing then transformed into electrocompetent *E. coli* str. JW2197-1 lacking the periplasmic trypsin inhibitor, ecotin.

FIG. 12 shows a flowchart of a method for detection of protease inhibitory activity on protein based plates.

FIG. 13 shows Dinitrosalicylic Acid (DNS) assay for the detection of reducing sugars produced by active amylase under a trypsin challenge. 200 mL of the YebF and YebF-SFTI supernatants or LB was mixed with 10 mL of a 1.25 mg/mL trypsin solution and allowed to equilibrate for 30 minutes. Heat inactivated trypsin served as a control. 10 mL amylase at 1 mg/mL was considered a 1× concentration and two-fold dilutions to 1/16× were conducted. The amylase was then added to the mixtures and incubated at 37° C. for five hours to allow digestion. 100 mL of 1% starch solution was then added and the reaction allowed to proceed for fifteen minutes. DNS was added and the mixture was boiled for 5 minutes, diluted with 500 mL H2O, and absorbance was read at 515 nm.

EXAMPLES

In order to more fully illustrate the technology, the following examples are provided.

Example 1

A *Salmonella* expression vector.

Inducible expression vectors for *E. coli* and *Salmonella*, such as arabinose inducible expression vectors, are widely available and known to those skilled in the art. By way of example, an expression vector typically contains a promoter which functions to generate an mRNA from the DNA, such as an inducible arabinose promoter with a functional ribosomal binding site (RBS) an initiation codon (ATG) and suitable cloning sites for operable insertion of the functional DNA encoding the effector proteins described below into the vector, followed by a transcriptional termination site, plasmid origin of replication, and an antibiotic resistance factor that allows selection for the plasmid. Vectors that lack antibiotic resistance such as asd(−) balanced lethal vectors (Galan et al., 1990 cloning and characterization of the asd gene of *Salmonella Typhimurium*: use in stable maintenance of recombinant *Salmonella* vaccine strains, Gene 94: 29-35) may also be used, or insertion into the chromosome.

Example 2

Modified TGFα-GIII-KDEL (A. Kihara and I. Pastan. Small Chimeric Toxins Containing Only Transforming Growth Factor α and Domain III of *Pseudomonas* Exotoxin with Good Antitumor Activity in Mice. Cancer Res 1994: 54:5154-5159). A modified form with an added OmpA signal sequence, extended flexible linker and presence of domain Ib with enhanced activity functionally expressed, secreted, surface displayed and/or released is shown in FIG. 1A. The construct contains an OmpA secretion signal, TGFα targeting domain, a GGGGS(×3) SEQ ID NO.: 008 linker, ToxA domain Ib (containing cysteine bonding), ToxA domain III followed by, optionally KDEL retrograde trafficking signal; without KDEL the native signal REDLK SEQ ID NO.: 023 is used. The complete sequence of the arabinose inducible plasmid capable of expressing the construct with a start codon at 351 and a stop codon at 1364 is:

```
                                        SEQ ID NO.: 001
gggGGCGGCCGCaagaaaccaattgtccatattgcatcagacattgccgt cactgcgtcttttactggctcttctcgctaaccaaaccggtaaccccgct tattaaaagcattctgtaacaaagcgggaccaaagccatgacaaaaacgc gtaacaaaagtgtctataatcacggcagaaaagtccacattgattatttg cacggcgtcacactttgctatgccatagcatttttatccataagattagc ggatcctacctgacgcttttatcgcaactctctactgtttctccatacc cgttttttgggctagcgaattcgagctCGGTACCCAGGAGGAATTCACC

ATGGCTAAAAAGACAGCTATCGCGATTGCAGTGGCACTGGCTGGTTTCGC

TACCGTAGCGCAGGCAGctGTGGTGAGCCATTTTAACGATTGCCCGGATA
```

```
                                           -continued
GCCATACCCAGTTTTGCTTTCATGGCACCTGCCGCTTTCTGGTGCAGGAA

GATAAACCGGCGTGCGTGTGCCATAGCGGTTATGTGGGCGCTCGCTGCGA

ACATGCGGATCTGCTGGCcCATCAACTAGTGGGCGGTGGTGGCAGTGGTG

GCGGCGGCTCTGGTGGTGGCGGGTCCCGGGGTctgacctgcccggtcgcc gccggtgaatgcgcgggcccggcggacagcggcgacgccctgctggagcg caactatcccactggcgcggagttcctcggcgacggcggcgacgtcagct tcagcacccgcggcacgcagaactggacggtggagcggctgctccaggcg caccgccaactggaggagcgcggctatgtgttcgtcggctaccacggcac cttcctcgaagcggcgcaaagcatcgtcttcggcggggtgcgcgcgcgca gccaggacctcgacgcgatctggcgcggtttctatatcgccggcgatccg gcgctggcctacggctacgcccaggaccaggaacccgacgcacgcggccg gatccgcaacggtgccctgctgcgggtctatgtgccgcgctcgagcctgc cgggcttctaccgcaccagcctgaccctggccgcgccggaggcggcgggc gaggtcgaacggctgatcggccatccgctgccgctgcgcctggacgccat caccggccccgaggaggaaggcgggcgcctggagaccattctcggctggc cgctggccgagcgcaccgtggtgattccctcggcgatccccaccgacccg cgcaacgtcggcggcgacctcgaccgtccagcatcccgacaaggaaca ggcgatcagcgccctgccggactacgccagccagcccggcaaaccgccga aagatgaactgtaaCTCGAGTagatctgtactCTAGAGTCGACCTGCAGG

CATGCAAGCTTGGCTGTTTTGGCGGATGAGAGAAGATTTTCAGCCTGATA

CAGATTAAATCAGAACGCAGAAGCGGTCTGATAAAACAGAATTTGCCTGG

CGGCAGTAGCGCGGTGGTCCCACCTGACCCCATGCCGAACTCAGAAGTGA

AACGCCGTAGCGCCGATGGTAGTGTGGGGTCTCCCCATGCGAGAGTAGGG

AACTGCCAGGCATCAAATAAAACGAAAGGCTCAGTCGAAAGACTGGGCCT

TTCGTTTTATCTGTTGTTTGTCGGTGAACGCTCTCCTGAGTAGGACAAAT

CCGCCGGGAGCGGATTTGAACGTTGCGAAGCAACGGCCCGGAGGGTGGCG

GGCAGGACGCCCGCCATAAACTGCCAGGCATCAAATTAAGCAGAAGGCCA

TCCTGACGGATGGCCTTTTTGCGTTTCTACAAACTCTTTTTGTTTATTTT

TCTAAATACATTCAAATATGTATCCGCTCATGAGACAATAACCCTGATAA

ATGCTTCAATAATATTGAAAAAGGAAGAGTATGAGTATTCAACATTTCCG

TGTCGCCCTTATTCCCTTTTTTGCGGCATTTTGCCTTCCTGTTTTTGCTC

ACCCAGAAACGCTGGTGAAAGTAAAAGATGCTGAAGATCAGTTGGGTGCA

CGAGTGGGTTACATCGAACTGGATCTCAACAGCGGTAAGATCCTTGAGAG

TTTTCGCCCCGAAGAACGTTTTCCAATGATGAGCACTTTTAAAGTTCTGC

TATGTGGCGCGGTATTATCCCGTGTTGACGCCGGGCAAGAGCAACTCGGT

CGCCGCATACACTATTCTCAGAATGACTTGGTTGAGTACTCACCAGTCAC

AGAAAAGCATCTTACGGATGGCATGACAGTAAGAGAATTATGCAGTGCTG

CCATAACCATGAGTGATAACACTGCGGCCAACTTACTTCTGACAACGATC

GGAGGACCGAAGGAGCTAACCGCTTTTTTGCACAACATGGGGGATCATGT

AACTCGCCTTGATCGTTGGGAACCGGAGCTGAATGAAGCCATACCAAACG

ACGAGCGTGACACCACGATGCCTACAGCAATGGCAACAACGTTGCGCAAA
```

-continued

```
CTATTAACTGGCGAACTACTTACTCTAGCTTCCCGGCAACAATTAATAGA

CTGGATGGAGGCGGATAAAGTTGCAGGACCACTTCTGCGCTCGGCCCTTC

CGGCTGGCTGGTTTATTGCTGATAAATCTGGAGCCGGTGAGCGTGGGTCT

CGCGGTATCATTGCAGCACTGGGGCCAGATGGTAAGCCCTCCCGTATCGT

AGTTATCTACACGACGGGGAGTCAGGCAACTATGGATGAACGAAATAGAC

AGATCGCTGAGATAGGTGCCTCACTGATTAAGCATTGGTAACTGTCAGAC

CAAGTTTACTCATATATACTTTAGATTGATTTAAAACTTCATTTTTAATT

TAAAAGGATCTAGGTGAAGATCCTTTTTGATAATCTCATGACCAAAATCC

CTTAACGTGAGTTTTCGTTCCACTGAGCGTCAGACCCCGTAGAAAAGATC

AAAGGATCTTCTTGAGATCCTTTTTTTTCTGCGCGTAATCTGCTGCTTGCA

AACAAAAAAACCACCGCTACCAGCGGTGGTTTGTTTGCCGGATCAAGAGC

TACCAACTCTTTTTCCGAAGGTAACTGGCTTCAGCAGAGCGCAGATACCA

AATACTGTCCTTCTAGTGTAGCCGTAGTTAGGCCACCACTTCAAGAACTC

TGTAGCACCGCCTACATACCTCGCTCTGCTAATCCTGTTACCAGTGGCTG

CTGCCAGTGGCGATAAGTCGTGTCTTACCGGGTTGGACTCAAGACGATAG

TTACCGGATAAGGCGCAGCGGTCGGGCTGAACGGGGGGTTCGTGCACACA

GCCCAGCTTGGAGCGAACGACCTACACCGAACTGAGATACCTACAGCGTG

AGCTATGAGAAAGCGCCACGCTTCCCGAAGGGAGAAAGGCGGACAGGTAT

CCGGTAAGCGGCAGGGTCGGAACAGGAGAGCGCACGAGGGAGCTTCCAGG

GGGAAACGCCTGGTATCTTTATAGTCCTGTCGGGTTTCGCCACCTCTGAC

TTGAGCGTCGATTTTTGTGATGCTCGTCAGGGGGCGGAGCCTATGGAAA

AACGCCAGCAACGCGGCCTTTTTACGGTTCCTGGCCTTTTGCTGGCCTTT

TGCTCACATGTTCTTTCCTGCGTTATCCCCTGATTCTGTGGATAACCGTA

TTACCGCCTTTGAGTGAGCTGATACCGCTCGCCGCAGCCGAACGACCGAG

CGCAGCGAGTCAGTGAGCGAGGAAGCGGAAGAGCGCCTGATGCGGTATTT

TCTCCTTACGCATCTGTGCGGTATTTCACACCGCATATG
```

The complete sequence of the arabinose inducible plasmid capable of expressing the construct with a start codon at 351 and a stop codon at 1364 together with the colicin E3 lysis protein from 1399 to 1542 is:

```
                                      SEQ ID NO.: 002
gggGGCGGCCGCaagaaaccaattgtccatattgcatcagacattgccgt cactgcgtcttttactggctcttctcgctaaccaaaccggtaaccccgct tattaaaagcattctgtaacaaagcgggaccaaagccatgacaaaaacgc gtaacaaaagtgtctataatcacggcagaaaagtccacattgattatttg cacggcgtcacactttgctatgccatagcattttttatccataagattagc ggatcctacctgacgctttttatcgcaactctctactgtttctccatacc cgttttttgggctagcgaattcgagctCGGTACCCAGGAGGAATTCACC

ATGGCTAAAAAGACAGCTATCGCGATTGCAGTGGCACTGGCTGGTTTCGC

TACCGTAGCGCAGGCAGctGTGGTGAGCCATTTTAACGATTGCCCGGATA

GCCATACCCAGTTTTGCTTTCATGGCACCTGCCGCTTTCTGGTGCAGGAA

GATAAACCGGCGTGCGTGTGCCATAGCGGTTATGTGGGCGCTCGCTGCGA

ACATGCGGATCTGCTGGCcATCAACTAGTGGGCGGTGGTGGCAGTGGTG

GCGGCGGCTCTGGTGGTGGCGGGTCCCGGGGTctgacctgcccggtcgcc gccggtgaatgcgcgggcccggcggacagcggcgacgccctgctggagcg caactatcccactggcgcggagttcctcggcgacggcggcgacgtcagct tcagcaccgcggcacgcagaactggacggtggagcggctgctccaggcg caccgccaactggaggagcgcggctatgtgttcgtcggctaccacggcac cttcctcgaagcggcgcaaagcatcgtcttcggcggggtgcgcgcgcgca gccaggacctcgacgcgatctggcgcggtttctatatcgccggcgatccg gcgctggcctacggctacgcccaggaccaggaacccgacgcacgcggccg gatccgcaacggtgccctgctgcgggtctatgtgccgcgctcgagcctgc cgggcttctaccgcaccagcctgaccctggccgcgccggaggcggcgggc gaggtcgaacggctgatcggccatccgctgccgctgcgcctggacgccat caccggccccgaggaggaaggcgggcgcctggagaccattctcggctggc cgctggccgagcgcaccgtggtgattccctcggcgatccccaccgacccg cgcaacgtcggcggcgacctcgacccgtccagcatccccgacaaggaaca ggcgatcagcgccctgccggactacgccagccagcccggcaaaccgccga agatgaactgtaaCTCGAGtagatctgtactCTAGAAAGGAGTCGTTAT

GAAAAAAATAACAGGGATTATTTTATTGCTTCTTGCAGTCATTATTCTGT

CTGCATGTCAGGCAAACTATATCCGGGATGTTCAGGGCGGGACCGTATCT

CCGTCATCAACAGCTGAAGTGACCGGATTAGCAACGCAGTAACTGCAGGC

ATGCAAGCTTGGCTGTTTTGGCGGATGAGAGAAGATTTTCAGCCTGATAC

AGATTAAATCAGAACGCAGAAGCGGTCTGATAAAACAGAATTTGCCTGGC

GGCAGTAGCGCGGTGGTCCCACCTGACCCCATGCCGAACTCAGAAGTGAA

ACGCCGTAGCGCCGATGGTAGTGTGGGGTCTCCCCATGCGAGAGTAGGGA

ACTGCCAGGCATCAAATAAAACGAAAGGCTCAGTCGAAAGACTGGGCCTT

TCGTTTTATCTGTTGTTTGTCGGTGAACGCTCTCCTGAGTAGGACAAATC

CGCCGGGAGCGGATTTGAACGTTGCGAAGCAACGGCCCGGAGGGTGGCGG

GCAGGACGCCCGCCATAAACTGCCAGGCATCAAATTAAGCAGAAGGCCAT

CCTGACGGATGGCCTTTTTGCGTTTCTACAAACTCTTTTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTGTTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA
```

```
ACTCGCCTTGATCGTTGGGAACCGGAGCTGAATGAAGCCATACCAAACGA
CGAGCGTGACACCACGATGCCTACAGCAATGCAACAACGTTGCGCAAAC
TATTAACTGGCGAACTACTTACTCTAGCTTCCCGGCAACAATTAATAGAC
TGGATGGAGGCGGATAAAGTTGCAGGACCACTTCTGCGCTCGGCCCTTCC
GGCTGGCTGGTTTATTGCTGATAAATCTGGAGCCGGTGAGCGTGGGTCTC
GCGGTATCATTGCAGCACTGGGGCCAGATGGTAAGCCCTCCCGTATCGTA
GTTATCTACACGACGGGGAGTCAGGCAACTATGGATGAACGAAATAGACA
GATCGCTGAGATAGGTGCCTCACTGATTAAGCATTGGTAACTGTCAGACC
AAGTTTACTCATATATACTTTAGATTGATTTAAAACTTCATTTTTAATTT
AAAAGGATCTAGGTGAAGATCCTTTTTGATAATCTCATGACCAAAATCCC
TTAACGTGAGTTTTCGTTCCACTGAGCGTCAGACCCCGTAGAAAAGATCA
AAGGATCTTCTTGAGATCCTTTTTTTCTGCGCGTAATCTGCTGCTTGCAA
ACAAAAAAACCACCGCTACCAGCGGTGGTTTGTTTGCCGGATCAAGAGCT
ACCAACTCTTTTTCCGAAGGTAACTGGCTTCAGCAGAGCGCAGATACCAA
ATACTGTCCTTCTAGTGTAGCCGTAGTTAGGCCACCACTTCAAGAACTCT
GTAGCACCGCCTACATACCTCGCTCTGCTAATCCTGTTACCAGTGGCTGC
TGCCAGTGGCGATAAGTCGTGTCTTACCGGGTTGGACTCAAGACGATAGT
TACCGGATAAGGCGCAGCGGTCGGGCTGAACGGGGGGTTCGTGCACACAG
CCCAGCTTGGAGCGAACGACCTACACCGAACTGAGATACCTACAGCGTGA
GCTATGAGAAAGCGCCACGCTTCCCGAAGGGAGAAAGGCGGACAGGTATC
CGGTAAGCGGCAGGGTCGGAACAGGAGAGCGCACGAGGGAGCTTCCAGGG
GGAAACGCCTGGTATCTTTATAGTCCTGTCGGGTTTCGCCACCTCTGACT
TGAGCGTCGATTTTTGTGATGCTCGTCAGGGGGCGGAGCCTATGGAAAA
ACGCCAGCAACGCGGCCTTTTTACGGTTCCTGGCCTTTTGCTGGCCTTTT
GCTCACATGTTCTTTCCTGCGTTATCCCCTGATTCTGTGGATAACCGTAT
TACCGCCTTTGAGTGAGCTGATACCGCTCGCCGCAGCCGAACGACCGAGC
GCAGCGAGTCAGTGAGCGAGGAAGCGGAAGAGCGCCTGATGCGGTATTTT
CTCCTTACGCATCTGTGCGGTATTTCACACCGCATATG
```

Example 3

Modified TGFα-GIII-KDEL (A. Kihara and I. Pastan. Small Chimeric Toxins Containing Only Transforming Growth Factor α and Domain III of *Pseudomonas* Exotoxin with Good Antitumor Activity in Mice. Cancer Res 1994: 54:5154-5159). A modified form with an added OmpA signal sequence and extended flexible linker with enhanced activity functionally expressed, secreted, surface displayed and/or released is shown in FIG. 1B. The construct contains an OmpA secretion signal, TGFα targeting domain, a GGGGS(×3), SEQ ID NO.: 008 linker, ToxA domain III followed by, optionally KDEL retrograde trafficking signal; without KDEL the native signal REDLK SEQ ID NO.: 023 is used. The complete sequence of the arabinose inducible plasmid capable of expressing the construct with a start codon at 351 and a stop codon at 1286 is:

SEQ ID NO.: 003 gggGGCGGCCGCaagaaaccaattgtccatattgcatcagacattgccgt
cactgcgtcttttactggctcttctcgctaaccaaaccggtaaccccgct
tattaaaagcattctgtaacaaagcgggaccaaagccatgacaaaaacgc
gtaacaaaagtgtctataatcacggcagaaaagtccacattgattatttg
cacggcgtcacactttgctatgccatagcatttttatccataagattagc
ggatcctacctgacgctttttatcgcaactctctactgtttctccatacc
cgtttttttgggctagcgaattcgagctCGGTACCCAGGAGGAATTCACC
ATGGCTAAAAAGACAGCTATCGCGATTGCAGTGGCACTGGCTGGTTTCGC
TACCGTAGCGCAGGCAGctGTGGTGAGCCATTTTAACGATTGCCCGGATA
GCCATACCCAGTTTTGCTTTCATGGCACCTGCCGCTTTCTGGTGCAGGAA
GATAAACCGGCGTGCGTGTGCCATAGCGGTTATGTGGGCGCTCGCTGCGA
ACATGCGGATCTGCTGGCccATCAACTAGTGGGCGGTGGTGGCAGTGGTG
GCGGCGGCTCTGGTGGTGGCGGGTCCCGGGGTactggcgcggagttcctc
ggcgacggcggcgacgtcagcttcagcacccgcggcacgcagaactggac
ggtggagcggctgctccaggcgcaccgccaactggaggagcgcggctatg
tgttcgtcggctaccacggcaccttcctcgaagcggcgcaaagcatcgtc
ttcggcggggtgcgcgcgcgcagccaggacctcgacgcgatctggcgcgg
tttctatatcgccggcgatccggcgctggcctacggctacgcccaggacc
aggaacccgacgcacgcggccggatccgcaacggtgccctgctgcgggtc
tatgtgccgcgctcgagcctgccgggcttctaccgcaccagcctgaccct
ggccgcgccggaggcggcgggcgaggtcgaacggctgatcggccatccgc
tgccgctgcgcctggacgccatcaccggccccgaggaggaaggcgggcgc
ctggagaccattctcggctggccgctggccgagcgcaccgtggtgattcc
ctcggcgatccccaccgacccgcgcaacgtcggcggcgacctcgacccgt
ccagcatccccgacaaggaacaggcgatcagcgccctgccggactacgcc
agccagcccggcaaaccgccgaaagatgaactgtaaCTCGAGTagatctg
tactCTAGAGTCGACCTGCAGGCATGCAAGCTTGGCTGTTTTGGCGGATG
AGAGAAGATTTTCAGCCTGATACAGATTAAATCAGAACGCAGAAGCGGTC
TGATAAAACAGAATTTGCCTGGCGGCAGTAGCGCGGTGGTCCCACCTGAC
CCCATGCCGAACTCAGAAGTGAAACGCCGTAGCGCCGATGGTAGTGTGGG
GTCTCCCCATGCGAGAGTAGGGAACTGCCAGGCATCAAATAAAACGAAAG
GCTCAGTCGAAAGACTGGGCCTTTCGTTTTATCTGTTGTTTGTCGGTGAA
CGCTCTCCTGAGTAGGACAAATCCGCCGGGAGCGGATTTGAACGTTGCGA
AGCAACGGCCCGGAGGGTGGCGGGCAGGACGCCCGCCATAAACTGCCAGG
CATCAAATTAAGCAGAAGGCCATCCTGACGGATGGCCTTTTTGCGTTTCT
ACAAACTCTTTTTGTTTATTTTTCTAAATACATTCAAATATGTATCCGCT
CATGAGACAATAACCCTGATAAATGCTTCAATAATATTGAAAAAGGAAGA
GTATGAGTATTCAACATTTCCGTGTCGCCCTTATTCCCTTTTTTGCGGCA
TTTTGCCTTCCTGTTTTTGCTCACCCAGAAACGCTGGTGAAAGTAAAAGA
TGCTGAAGATCAGTTGGGTGCACGAGTGGGTTACATCGAACTGGATCTCA ACAGCGGTAAGATCCTTGAGAGTTTTCGCCCCGAAGAACGTTTTCCAATG
ATGAGCACTTTTAAAGTTCTGCTATGTGGCGCGGTATTATCCCGTGTTGA
CGCCGGGCAAGAGCAACTCGGTCGCCGCATACACTATTCTCAGAATGACT
TGGTTGAGTACTCACCAGTCACAGAAAAGCATCTTACGGATGGCATGACA
GTAAGAGAATTATGCAGTGCTGCCATAACCATGAGTGATAACACTGCGGC
CAACTTACTTCTGACAACGATCGGAGGACCGAAGGAGCTAACCGCTTTTT
TGCACAACATGGGGGATCATGTAACTCGCCTTGATCGTTGGGAACCGGAG
CTGAATGAAGCCATACCAAACGACGAGCGTGACACCACGATGCCTACAGC
AATGGCAACAACGTTGCGCAAACTATTAACTGGCGAACTACTTACTCTAG
CTTCCCGGCAACAATTAATAGACTGGATGGAGGCGGATAAAGTTGCAGGA
CCACTTCTGCGCTCGGCCCTTCCGGCTGGCTGGTTTATTGCTGATAAATC
TGGAGCCGGTGAGCGTGGGTCTCGCGGTATCATTGCAGCACTGGGGCCAG
ATGGTAAGCCCTCCCGTATCGTAGTTATCTACACGACGGGGAGTCAGGCA
ACTATGGATGAACGAAATAGACAGATCGCTGAGATAGGTGCCTCACTGAT
TAAGCATTGGTAACTGTCAGACCAAGTTTACTCATATATACTTTAGATTG
ATTTAAAACTTCATTTTTAATTTAAAAGGATCTAGGTGAAGATCCTTTTT
GATAATCTCATGACCAAAATCCCTTAACGTGAGTTTTCGTTCCACTGAGC
GTCAGACCCCGTAGAAAAGATCAAAGGATCTTCTTGAGATCCTTTTTTTC
TGCGCGTAATCTGCTGCTTGCAAACAAAAAAACCACCGCTACCAGCGGTG
GTTTGTTTGCCGGATCAAGAGCTACCAACTCTTTTTCCGAAGGTAACTGG
CTTCAGCAGAGCGCAGATACCAAATACTGTCCTTCTAGTGTAGCCGTAGT
TAGGCCACCACTTCAAGAACTCTGTAGCACCGCCTACATACCTCGCTCTG
CTAATCCTGTTACCAGTGGCTGCTGCCAGTGGCGATAAGTCGTGTCTTAC
CGGGTTGGACTCAAGACGATAGTTACCGGATAAGGCGCAGCGGTCGGGCT
GAACGGGGGGTTCGTGCACACAGCCCAGCTTGGAGCGAACGACCTACACC
GAACTGAGATACCTACAGCGTGAGCTATGAGAAAGCGCCACGCTTCCCGA
AGGGAGAAAGGCGGACAGGTATCCGGTAAGCGGCAGGGTCGGAACAGGAG
AGCGCACGAGGGAGCTTCCAGGGGGAAACGCCTGGTATCTTTATAGTCCT
GTCGGGTTTCGCCACCTCTGACTTGAGCGTCGATTTTTGTGATGCTCGTC
AGGGGGGCGGAGCCTATGGAAAAACGCCAGCAACGCGGCCTTTTTACGGT
TCCTGGCCTTTTGCTGGCCTTTTGCTCACATGTTCTTTCCTGCGTTATCC
CCTGATTCTGTGGATAACCGTATTACCGCCTTTGAGTGAGCTGATACCGC
TCGCCGCAGCCGAACGACCGAGCGCAGCGAGTCAGTGAGCGAGGAAGCGG
AAGAGCGCCTGATGCGGTATTTTCTCCTTACGCATCTGTGCGGTATTTCA
CACCGCATATG The complete sequence of the arabinose inducible plasmid capable of expressing the construct with a start codon at 351 and a stop codon at 1286 together with the colicin E3 lysis protein from 1321 to 1464 is:

SEQ ID NO.: 004
gggGGCGGCCGCaagaaaccaattgtccatattgcatcagacattgccgt
cactgcgtcttttactggctcttctcgctaaccaaaccggtaaccccgct
tattaaaagcattctgtaacaaagcgggaccaaagccatgacaaaaacgc
gtaacaaaagtgtctataatcacggcagaaaagtccacattgattatttg
cacggcgtcacactttgctatgccatagcatttttatccataagattagc
ggatcctacctgacgcttttatcgcaactctctactgtttctccatacc
cgttttttgggctagcgaattcgagctCGGTACCCAGGAGGAATTCACC
ATGGCTAAAAAGACAGCTATCGCGATTGCAGTGGCACTGGCTGGTTTCGC
TACCGTAGCGCAGGCAGctGTGGTGAGCCATTTTAACGATTGCCCGGATA
GCCATACCCAGTTTTGCTTTCATGGCACCTGCCGCTTTCTGGTGCAGGAA
GATAAACCGGCGTGCGTGTGCCATAGCGGTTATGTGGGCGCTCGCTGCGA
ACATGCGGATCTGCTGGCcCATCAACTAGTGGGCGGTGGTGGCAGTGGTG
GCGGCGGCTCTGGTGGTGGCGGGTCCCGGGGTctgacctgcccggtcgcc
gccggtgaatgcgcgggcccggcggacagcggcgacgccctgctggagcg
caactatcccactggcgcggagttcctcggcgacggcggcgacgtcagct
tcagcaccgcggcacgcagaactggacggtggagcggctgctccaggcg
caccgccaactggaggagcgcggctatgtgttcgtcggctaccacggcac
cttcctcgaagcggcgcaaagcatcgtcttcggcggggtgcgcgcgcgca
gccaggacctcgacgcgatctggcgcggtttctatatcgccggcgatccg
gcgctggcctacggctacgcccaggaccaggaacccgacgcacgcggccg
gatccgcaacggtgccctgctgcgggtctatgtgccgcgctcgagcctgc
cgggcttctaccgcaccagcctgaccctggccgcgccggaggcggcgggc
gaggtcgaacggctgatcggccatccgctgccgctgcgcctggacgccat
caccggccccgaggaggaaggcgggcgcctggagaccattctcggctggc
cgctggccgagcgcaccgtggtgattccctcggcgatccccaccgacccg
cgcaacgtcggcggcgacctcgacccgtccagcatccccgacaaggaaca
ggcgatcagcgccctgccggactacgccagccagcccggcaaaccgccga
aagatgaactgtaaCTCGAGTagatctgtactCTAGAAAGGAGTCGTTAT
GAAAAAAATAACAGGGATTATTTTATTGCTTCTTGCAGTCATTATTCTGT
CTGCATGTCAGGCAAACTATATCCGGGATGTTCAGGGCGGGACCGTATCT
CCGTCATCAACAGCTGAAGTGACCGGATTAGCAACGCAGTAACTGCAGGC
ATGCAAGCTTGGCTGTTTTGGCGGATGAGAGAAGATTTTCAGCCTGATAC
AGATTAAATCAGAACGCAGAAGCGGTCTGATAAAACAGAATTTGCCTGGC
GGCAGTAGCGCGGTGGTCCCACCTGACCCCATGCCGAACTCAGAAGTGAA
ACGCCGTAGCGCCGATGGTAGTGTGGGGTCTCCCCATGCGAGAGTAGGGA
ACTGCCAGGCATCAAATAAAACGAAAGGCTCAGTCGAAAGACTGGGCCTT
TCGTTTTATCTGTTGTTTGTCGGTGAACGCTCTCCTGAGTAGGACAAATC
CGCCGGGAGCGGATTTGAACGTTGCGAAGCAACGGCCCGGAGGGTGGCGG
GCAGGACGCCCGCCATAAACTGCCAGGCATCAAATTAAGCAGAAGGCCAT
CCTGACGGATGGCCTTTTTGCGTTTCTACAAACTCTTTTTGTTTATTTTT
CTAAATACATTCAAATATGTATCCGCTCATGAGACAATAACCCTGATAAA
TGCTTCAATAATATTGAAAAAGGAAGAGTATGAGTATTCAACATTTCCGT

```
GTCGCCCTTATTCCCTTTTTTGCGGCATTTTGCCTTCCTGTTTTTGCTCA
CCCAGAAACGCTGGTGAAAGTAAAAGATGCTGAAGATCAGTTGGGTGCAC
GAGTGGGTTACATCGAACTGGATCTCAACAGCGGTAAGATCCTTGAGAGT
TTTCGCCCCGAAGAACGTTTTCCAATGATGAGCACTTTTAAAGTTCTGCT
ATGTGGCGCGGTATTATCCCGTGTTGACGCCGGGCAAGAGCAACTCGGTC
GCCGCATACACTATTCTCAGAATGACTTGGTTGAGTACTCACCAGTCACA
GAAAAGCATCTTACGGATGGCATGACAGTAAGAGAATTATGCAGTGCTGC
CATAACCATGAGTGATAACACTGCGGCCAACTTACTTCTGACAACGATCG
GAGGACCGAAGGAGCTAACCGCTTTTTTGCACAACATGGGGGATCATGTA
ACTCGCCTTGATCGTTGGGAACCGGAGCTGAATGAAGCCATACCAAACGA
CGAGCGTGACACCACGATGCCTACAGCAATGGCAACAACGTTGCGCAAAC
TATTAACTGGCGAACTACTTACTCTAGCTTCCCGGCAACAATTAATAGAC
TGGATGGAGGCGGATAAAGTTGCAGGACCACTTCTGCGCTCGGCCCTTCC
GGCTGGCTGGTTTATTGCTGATAAATCTGGAGCCGGTGAGCGTGGGTCTC
GCGGTATCATTGCAGCACTGGGGCCAGATGGTAAGCCCTCCCGTATCGTA
GTTATCTACACGACGGGGAGTCAGGCAACTATGGATGAACGAAATAGACA
GATCGCTGAGATAGGTGCCTCACTGATTAAGCATTGGTAACTGTCAGACC
AAGTTTACTCATATATACTTTAGATTGATTTAAAACTTCATTTTTAATTT
AAAAGGATCTAGGTGAAGATCCTTTTTGATAATCTCATGACCAAAATCCC
TTAACGTGAGTTTTCGTTCCACTGAGCGTCAGACCCCGTAGAAAAGATCA
AAGGATCTTCTTGAGATCCTTTTTTTCTGCGCGTAATCTGCTGCTTGCAA
ACAAAAAAACCACCGCTACCAGCGGTGGTTTGTTTGCCGGATCAAGAGCT
ACCAACTCTTTTTCCGAAGGTAACTGGCTTCAGCAGAGCGCAGATACCAA
ATACTGTCCTTCTAGTGTAGCCGTAGTTAGGCCACCACTTCAAGAACTCT
GTAGCACCGCCTACATACCTCGCTCTGCTAATCCTGTTACCAGTGGCTGC
TGCCAGTGGCGATAAGTCGTGTCTTACCGGGTTGGACTCAAGACGATAGT
TACCGGATAAGGCGCAGCGGTCGGGCTGAACGGGGGGTTCGTGCACACAG
CCCAGCTTGGAGCGAACGACCTACACCGAACTGAGATACCTACAGCGTGA
GCTATGAGAAAGCGCCACGCTTCCCGAAGGGAGAAAGGCGGACAGGTATC
CGGTAAGCGGCAGGGTCGGAACAGGAGAGCGCACGAGGGAGCTTCCAGGG
GGAAACGCCTGGTATCTTTATAGTCCTGTCGGGTTTCGCCACCTCTGACT
TGAGCGTCGATTTTTGTGATGCTCGTCAGGGGGCGGAGCCTATGGAAAA
ACGCCAGCAACGCGGCCTTTTTACGGTTCCTGGCCTTTTGCTGGCCTTTT
GCTCACATGTTCTTTCCTGCGTTATCCCCTGATTCTGTGGATAACCGTAT
TACCGCCTTTGAGTGAGCTGATACCGCTCGCCGCAGCCGAACGACCGAGC
GCAGCGAGTCAGTGAGCGAGGAAGCGGAAGAGCGCCTGATGCGGTATTTT
CTCCTTACGCATCTGTGCGGTATTTCACACCGCATATG
```

Example 4

Modified TGFα-PE38 (Kreitman, R. J., Siegall, C. B., Chaudhary, V. K, Fitzgerald, D. J., and Pastan. I. Properties of Chimeric Toxins with Two Recognition Domains: Interleukin 6 and Transforming Growth Factor α at Different Locations in *Pseudomonas* Exotoxin. Bioconjugate Chem. 1992, 3, 63-68.)

The original form of this product represents a deletion of amino acids 365-380 of ToxA domain I. The modified form is a chimera containing an OmpA secretion signal, TGFα targeting domain, a GGGGS(×3), SEQ ID NO.: 008 linker, ToxA PE38 (contains Domain II, partial Ib (Δ365-380 amino acids) domain III followed by, optionally KDEL retrograde trafficking signal; without KDEL the native signal REDLK SEQ ID NO.: 023 is used. Optionally, the colicin E3 lysis protein with a separate ribosomal binding site may be added. The modified form with an added extended flexible linker with enhanced activity functionally expressed, secreted, surface displayed and/or released is shown in FIG. 1C. The complete sequence of the arabinose inducible plasmid capable of expressing the construct with a start codon at 351 and a stop codon at 1664 is:

SEQ ID NO.: 005
```
gggGGCGGCCGCaagaaaccaattgtccatattgcatcagacattgccgt
cactgcgtcttttactggctcttctcgctaaccaaaccggtaacccgct
tattaaaagcattctgtaacaaagcgggaccaaagccatgacaaaaacgc
gtaacaaaagtgtctataatcacggcagaaaagtccacattgattatttg
cacggcgtcacactttgctatgccatagcattttttatccataagattagc
ggatcctacctgacgcttttatcgcaactctctactgtttctccatacc
cgttttttttgggctagcgaattcgagctCGGTACCCAGGAGGAATTCACC
ATGGCTAAAAAGACAGCTATCGCGATTGCAGTGGCACTGGCTGGTTTCGC
TACCGTAGCGCAGGCAGctGTGGTGAGCCATTTTAACGATTGCCCGGATA
GCCATACCCAGTTTTGCTTTCATGGCACCTGCCGCTTTCTGGTGCAGGAA
GATAAACCGGCGTGCGTGTGCCATAGCGGTTATGTGGGCGCTCGCTGCGA
ACATGCGGATCTGCTGGCcCATCAACTAGTGGGCGGTGGTGGCAGTGGTG
GCGGCGGCTCTGGTGGTGGCGGGTCCCggggtggcagcctggccgcgctg
accgcgcaccaggcttgccacctgccgctggagactttcacccgtcatcg
ccagccgcgcggctgggaacaactggagcagtgcggctatccggtgcagc
ggctggtcgccctctacctggcggcgcggctgtcgtggaaccaggtcgac
caggtgatccgcaacgccctggccagccccggcagcggcggcgacctggg
cgaagcgatccgcgagcagccggagcaggcccgtctggccctgacctgg
ccgccgccgagagcgagcgcttcgtccggcagggcaccggcaacgacgag
gccggcgcggccaacgccccggcggacagcggcgacgccctgctggagcg
caactatcccactggcgcggagttcctcggcgacggcggcgacgtcagct
tcagcacccgcggcacgcagaactggacggtggagcggctgctccaggcg
caccgccaactggaggagcgcggctatgtgttcgtcggctaccacggcac
cttcctcgaagcggcgcaaagcatcgtcttcggcggggtgcgcgcgcgca
gccaggacctcgacgcgatctggcgcggtttctatatcgccggcgatccg
gcgctggcctacgggctacgcccaggaccaggaacccgacgcacgcggccg
gatccgcaacggtgccctgctgcgggtctatgtgccgcgctcgagcctgc
cgggcttctaccgcaccagcctgaccctggccgcgccggaggcggcgggc
``` gaggtcgaacggctgatcggccatccgctgccgctgcgcctggacgccat caccggccccgaggaggaaggcgggcgcctggagaccattctcggctggc cgctggccgagcgcaccgtggtgattccctcggcgatccccaccgacccg cgcaacgtcggcggcgacctcgacccgtccagcatccccgacaaggaaca ggcgatcagcgccctgccggactacgccagccagcccggcaaaccgccga aagatgaactgtaaCTCGAGTagatctgtactCTAGAGTCGACCTGCAGG

CATGCAAGCTTGGCTGTTTTGGCGGATGAGAGAAGATTTTCAGCCTGATA

CAGATTAAATCAGAACGCAGAAGCGGTCTGATAAAACAGAATTTGCCTGG

CGGCAGTAGCGCGGTGGTCCCACCTGACCCCATGCCGAACTCAGAAGTGA

AACGCCGTAGCGCCGATGGTAGTGTGGGGTCTCCCCATGCGAGAGTAGGG

AACTGCCAGGCATCAAATAAAACGAAAGGCTCAGTCGAAAGACTGGGCCT

TTCGTTTTATCTGTTGTTTGTCGGTGAACGCTCTCCTGAGTAGGACAAAT

CCGCCGGGAGCGGATTTGAACGTTGCGAAGCAACGGCCCGGAGGGTGGCG

GGCAGGACGCCCGCCATAAACTGCCAGGCATCAAATTAAGCAGAAGGCCA

TCCTGACGGATGGCCTTTTTGCGTTTCTACAAACTCTTTTTGTTTATTTT

TCTAAATACATTCAAATATGTATCCGCTCATGAGACAATAACCCTGATAA

ATGCTTCAATAATATTGAAAAAGGAAGAGTATGAGTATTCAACATTTCCG

TGTCGCCCTTATTCCCTTTTTTGCGGCATTTTGCCTTCCTGTTTTTGCTC

ACCCAGAAACGCTGGTGAAAGTAAAAGATGCTGAAGATCAGTTGGGTGCA

CGAGTGGGTTACATCGAACTGGATCTCAACAGCGGTAAGATCCTTGAGAG

TTTTCGCCCCGAAGAACGTTTTCCAATGATGAGCACTTTTAAAGTTCTGC

TATGTGGCGCGGTATTATCCCGTGTTGACGCCGGGCAAGAGCAACTCGGT

CGCCGCATACACTATTCTCAGAATGACTTGGTTGAGTACTCACCAGTCAC

AGAAAAGCATCTTACGGATGGCATGACAGTAAGAGAATTATGCAGTGCTG

CCATAACCATGAGTGATAACACTGCGGCCAACTTACTTCTGACAACGATC

GGAGGACCGAAGGAGCTAACCGCTTTTTTGCACAACATGGGGGATCATGT

AACTCGCCTTGATCGTTGGGAACCGGAGCTGAATGAAGCCATACCAAACG

ACGAGCGTGACACCACGATGCCTACAGCAATGGCAACAACGTTGCGCAAA

CTATTAACTGGCGAACTACTTACTCTAGCTTCCCGGCAACAATTAATAGA

CTGGATGGAGGCGGATAAAGTTGCAGGACCACTTCTGCGCTCGGCCCTTC

CGGCTGGCTGGTTTATTGCTGATAAATCTGGAGCCGGTGAGCGTGGGTCT

CGCGGTATCATTGCAGCACTGGGGCCAGATGGTAAGCCCTCCCGTATCGT

AGTTATCTACACGACGGGGAGTCAGGCAACTATGGATGAACGAAATAGAC

AGATCGCTGAGATAGGTGCCTCACTGATTAAGCATTGGTAACTGTCAGAC

CAAGTTTACTCATATATACTTTAGATTGATTTAAAACTTCATTTTTAATT

TAAAAGGATCTAGGTGAAGATCCTTTTTGATAATCTCATGACCAAAATCC

CTTAACGTGAGTTTTCGTTCCACTGAGCGTCAGACCCCGTAGAAAAGATC

AAAGGATCTTCTTGAGATCCTTTTTTTCTGCGCGTAATCTGCTGCTTGCA

AACAAAAAAACCACCGCTACCAGCGGTGGTTTGTTTGCCGGATCAAGAGC

TACCAACTCTTTTTCCGAAGGTAACTGGCTTCAGCAGAGCGCAGATACCA

AATACTGTCCTTCTAGTGTAGCCGTAGTTAGGCCACCACTTCAAGAACTC

TGTAGCACCGCCTACATACCTCGCTCTGCTAATCCTGTTACCAGTGGCTG

CTGCCAGTGGCGATAAGTCGTGTCTTACCGGGTTGGACTCAAGACGATAG

TTACCGGATAAGGCGCAGCGGTCGGGCTGAACGGGGGGTTCGTGCACACA

GCCCAGCTTGGAGCGAACGACCTACACCGAACTGAGATACCTACAGCGTG

AGCTATGAGAAAGCGCCACGCTTCCCGAAGGGAGAAAGGCGGACAGGTAT

CCGGTAAGCGGCAGGGTCGGAACAGGAGAGCGCACGAGGGAGCTTCCAGG

GGGAAACGCCTGGTATCTTTATAGTCCTGTCGGGTTTCGCCACCTCTGAC

TTGAGCGTCGATTTTTGTGATGCTCGTCAGGGGGCGGAGCCTATGGAAA

AACGCCAGCAACGCGGCCTTTTTACGGTTCCTGGCCTTTTGCTGGCCTTT

TGCTCACATGTTCTTTCCTGCGTTATCCCCTGATTCTGTGGATAACCGTA

TTACCGCCTTTGAGTGAGCTGATACCGCTCGCCGCAGCCGAACGACCGAG

CGCAGCGAGTCAGTGAGCGAGGAAGCGGAAGAGCGCCTGATGCGGTATTT

TCTCCTTACGCATCTGTGCGGTATTTCACACCGCATATG

The complete sequence of the arabinose inducible plasmid capable of expressing the construct with a start codon at 351 and a stop codon at 1664 together with the colicin E3 lysis protein from 1699 to 1842 is:

SEQ ID NO.: 006 gggGGCGGCCGCaagaaaccaattgtccatattgcatcagacattgccgt cactgcgtcttttactggctcttctcgctaaccaaaccggtaaccccgct tattaaaagcattctgtaacaaagcgggaccaaagccatgacaaaaacgc gtaacaaaagtgtctataatcacggcagaaaagtccacattgattatttg cacggcgtcacactttgctatgccatagcattttttatccataagattagc ggatcctacctgacgctttttatcgcaactctctactgtttctccatacc cgttttttgggctagcgaattcgagctCGGTACCCAGGAGGAATTCACC

ATGGCTAAAAAGACAGCTATCGCGATTGCAGTGGCACTGGCTGGTTTCGC

TACCGTAGCGCAGGCAGctGTGGTGAGCCATTTTAACGATTGCCCGGATA

GCCATACCCAGTTTTGCTTTCATGGCACCTGCCGCTTTCTGGTGCAGGAA

GATAAACCGGCGTGCGTGTGCCATAGCGGTTATGTGGGCGCTCGCTGCGA

ACATGCGGATCTGCTGGCcCATCAACTAGTGGGCGGTGGTGGCAGTGGTG

GCGGCGGCTCTGGTGGTGGCGGGTCCCggggtggcagcctggccgcgctg accgcgcaccaggcttgccacctgccgctggagactttcacccgtcatcg ccagccgcgcggctgggaacaactggagcagtgcggctatccggtgcagc ggctggtcgccctctacctggcggcgcggctgtcgtggaaccaggtcgac caggtgatccgcaacgccctggccagcccggcagcggcggcgacctggg cgaagcgatccgcgagcagccgggagcaggcccgtctggccctgaccctgg ccgccgccgagagcgagcgcttcgtccggcagggcaccggcaacgacgag gccggcgcggccaacgccccggcggacagcggcgacgccctgctggagcg caactatcccactggcgcggagttcctcggcgacggcggcgacgtcagct tcagcacccgcggcacgcagaactggacggtggagcggctgctccaggcg caccgccaactggaggagcgcggctatgtgttcgtcggctaccacggcac -continued
cttcctcgaagcggcgcaaagcatcgtcttcggcggggtgcgcgcgcga gccaggacctcgacgcgatctggcgcggtttctatatcgccggcgatccg gcgctggcctacggctacgcccaggaccaggaacccgacgcacgcggccg gatccgcaacggtgccctgctgcgggtctatgtgccgcgctcgagcctgc cgggcttctaccgcaccagcctgacccctggccgcgccggaggcggcgggc gaggtcgaacggctgatcggccatccgctgccgctgcgcctggacgccat caccggccccgaggaggaaggcgggcgcctggagaccattctcggctggc cgctggccgagcgcaccgtggtgattccctcggcgatccccaccgacccg cgcaacgtcggcggcgacctcgacccgtccagcatccccgacaaggaaca ggcgatcagcgccctgccggactacgccagccagcccggcaaaccgccga aagatgaactgtaaCTCGAGTagatctgtactCTAGAAAGGAGTCGTTAT

GAAAAAAATAACAGGGATTATTTTATTGCTTCTTGCAGTCATTATTCTGT

CTGCATGTCAGGCAAACTATATCCGGGATGTTCAGGGCGGGACCGTATCT

CCGTCATCAACAGCTGAAGTGACCGGATTAGCAACGCAGTAACTGCAGGC

ATGCAAGCTTGGCTGTTTTGGCGGATGAGAGAAGATTTTCAGCCTGATAC

AGATTAAATCAGAACGCAGAAGCGGTCTGATAAAACAGAATTTGCCTGGC

GGCAGTAGCGCGGTGGTCCCACCTGACCCCATGCCGAACTCAGAAGTGAA

ACGCCGTAGCGCCGATGGTAGTGTGGGGTCTCCCCATGCGAGAGTAGGGA

ACTGCCAGGCATCAAATAAAACGAAAGGCTCAGTCGAAAGACTGGGCCTT

TCGTTTTATCTGTTGTTTGTCGGTGAACGCTCTCCTGAGTAGGACAAATC

CGCCGGGAGCGGATTTGAACGTTGCGAAGCAACGGCCCGGAGGGTGGCGG

GCAGGACGCCCGCCATAAACTGCCAGGCATCAAATTAAGCAGAAGGCCAT

CCTGACGGATGGCCTTTTTGCGTTTCTACAAACTCTTTTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTGTTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTACAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

-continued
GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCTGATGCGGTATTTT

CTCCTTACGCATCTGTGCGGTATTTCACACCGCATATG

Example 5

An artificial typhoid toxin operon lacking sty and ttsA.

An artificial, inducible typhoid toxin operon lacking sty and ttsA as shown in FIG. 2B, is generated by multiple PCR and restriction endonuclease cloning steps known to those skilled in the art. The operon is capable of being induced with an inducing agent, in the present instance, arabinose. As compared with FIG. 1B, the artificial operon lacks the sty and ttsA genes. The complete sequence of the arabinose inducible plasmid capable of expressing the construct with a cldtB start codon at 351 and a stop codon at 1163, pltB start at 1197 and stop at 1610 and pltA 1627-2355:

SEQ ID NO.: 007
gggGGCGGCCGCaagaaaccaattgtccatattgcatcagacattgccgt cactgcgtcttttactggctcttctcgctaaccaaaccggtaaccccgct tattaaaagcattctgtaacaaagcgggaccaaagccatgacaaaaacgc gtaacaaaagtgtctataatcacggcagaaaagtccacattgattatttg cacggcgtcacactttgctatgccatagcatttttatccataagattagc ggatcctacctgacgcttttatcgcaactctctactgtttctccatacc cgttttttgggctagcgaattcgagctcggtacccaggaggaattcaCC

ATGGTCAAAAACCTGTTTTTTTCCTTCTGACCATGATCATCTGCAGCTA

TATTTCTTTTGCCTGCGCTAATATCAGTGACTACAAAGTTATGACCTGGA

```
ATCTTCAGGGCTCTTCAGCATCTACAGAAAGTAAATGGAATGTCAATGTC
AGACAGCTTTTAAGCGGTACTGCCGGTGTGGATATTCTTATGGTACAGGA
GGCCGGTGCTGTTCCCACCTCAGCGGTTCCTACCGGACGACATATTCAGC
CTTTTGGAGTGGGTATTCCCATTGATGAATACACCTGGAATCTCGGAACC
ACCAGCCGTCAGGATATAAGATATATCTACTACTCGGCTATTGATGTTGG
AGCACGCCGTGTTAATCTGGCAATAGTTTCCAGACAAAGAGCGGATAATG
TTTATGTCTTGCGTCCGACAACTGTCGCATCTCGCCCCGTCATTGGCATC
GGACTGGGTAATGATGTTTTTCTGACAGCGCACGCACTGGCTAGTGGAGG
TCCGGATGCTGCAGCTATTGTCAGGGTTACCATTAATTTTTTAGACAAC
CTCAGATGCGGCATTTATCCTGGTTTCTTGCCGGGGATTTTAATCGCAGC
CCAGACAGACTTGAAAATGACCTGATGACTGAGCATCTGGAACGAGTTGT
AGCCGTACTCGCACCTACAGAACCCACGCAAATTAGCGGTGGTATTTTAG
ATTATGGGGTCATTGTCGATCGAGCACCTTATTCACAAAGGGTCGAAGCA
TTACGTAATCCACAACTCGCTTCTGATCATTATCCCGTAGCCTTTTTGGC
ACGAAGCTGTTAAtgaTCTAGATAAGTCGACgtacAGGAgagtagtATGT
ATATAAATAAGTTTGTGCCTGTTTATACATTATTAATTCTCATTTATTCT
TTTAATGCCAGCGCTGAGTGGACAGGAGATAATACGAACGCCTATTACTC
AGACGAAGTTATCAGTGAATTACATGTTGGTCAGATAGATACTAGTCCTT
ATTTTTGCATAAAAACGGTTAAAGCTAACGGTAGTGGTACACCAGTTGTT
GCATGTGCGGTATCAAAGCAGAGCATATGGGCGCCCTCCTTTAAAGAACT
TCTTGATCAGGCAAGATATTTTTACAGTACAGGGCAATCCGTAAGGATTC
ATGTTCAAAAAATATCTGGACCTATCCGCTTTTTGTTAATACCTTTTCA
GCAAATGCTCTTGTGGGACTATCATCGTGCAGTGCGACACAATGCTTTGG
ACCCAAGTAAgaggggagaagaaataATGAAAAAGTTAATATTCTTAACC
TTATCTATAGTTAGCTTTAATAACTATGCTGTAGATTTTGTGTATCGTGT
GGACTCAACCCCGCCGGACGTTATTTTTCGCGATGGGTTTTCACTACTTG
GGTATAACCGTAACTTTCAGCAATTTATTAGTGGAAGGTCATGTAGTGGT
GGAAGTAGTGACAGTCGCTATATTGCAACAACCTCAAGTGTTAATCAAAC
ATATGCTATAGCCAGAGCGTACTATTCTCGCTCAACATTCAAAGGTAATT
TATACAGATATCAGATTCGTGCAGATAATAATTTCTACAGCTTGCTCCCA
TCCATCACCTATCTGGAAACGCAAGGTGGTCACTTTAATGCTTATGAAAA
AACGATGATGCGATTGCAAAGAGAGTATGTTTCCACATTATCTATTTTAC
CCGAGAATATTCAAAAGGCCGTGGCGCTAGTTTATGATAGCGCAACCGGT
CTGGTAAAGGATGGTGTAAGCACAATGAATGCCAGTTATTTAGGTTTAAG
CACTACGTCTAATCCTGGTGTGATACCTTTTCTTCCGGAACCGCAGACGT
ATACCCAACAACGAATTGATGCATTCGGCCCATTAATAAGTTCATGCTTT
TCAATAGGTAGCGTATGTCAGTCACATCGAGGGCAAAGAGCTGACGTATA
CAACATGTCTTTTTATGATGCAAGACCTGTAATAGAACTTATACTTTCTA
AATAAatgaaacttacctatgttgccGCATGCAAGCTAGCTTGGCTGTTT
TGGCGGATGAGAGAAGATTTTCAGCCTGATACAGATTAAATCAGAACGCA
GAAGCGGTCTGATAAAACAGAATTTGCCTGGCGGCAGTAGCGCGGTGGTC
CCACCTGACCCCATGCCGAACTCAGAAGTGAAACGCCGTAGCGCCGATGG
TAGTGTGGGGTCTCCCCATGCGAGAGTAGGGAACTGCCAGGCATCAAATA
AAACGAAAGGCTCAGTCGAAAGACTGGGCCTTTCGTTTTATCTGTTGTTT
GTCGGTGAACGCTCTCCTGAGTAGGACAAATCCGCCGGGAGCGGATTTGA
ACGTTGCGAAGCAACGGCCCGGAGGGTGGCGGGCAGGACGCCCGCCATAA
ACTGCCAGGCATCAAATTAAGCAGAAGGCCATCCTGACGGATGGCCTTTT
TGTTTCGCTACAAACTCTTTTTGTTTATTTTTCTAAATACATTCAAATAT
GTATCCGCTCATGAGACAATAACCCTGATAAATGCTTCAATAATATTGAA
AAAGGAAGAGTATGAGTATTCAACATTTCCGTGTCGCCCTTATTCCCTTT
TTTGCGGCATTTTGCCTTCCTGTTTTTGCTCACCCAGAAACGCTGGTGAA
AGTAAAAGATGCTGAAGATCAGTTGGGTGCACGAGTGGGTTACATCGAAC
TGGATCTCAACAGCGGTAAGATCCTTGAGAGTTTTCGCCCCGAAGAACGT
TTTCCAATGATGAGCACTTTTAAAGTTCTGCTATGTGGCGCGGTATTATC
CCGTGTTGACGCCGGGCAAGAGCAACTCGGTCGCCGCATACACTATTCTC
AGAATGACTTGGTTGAGTACTCACCAGTCACAGAAAAGCATCTTACGGAT
GGCATGACAGTAAGAGAATTATGCAGTGCTGCCATAACCATGAGTGATAA
CACTGCGGCCAACTTACTTCTGACAACGATCGGAGGACCGAAGGAGCTAA
CCGCTTTTTTGCACAACATGGGGGATCATGTAACTCGCCTTGATCGTTGG
GAACCGGAGCTGAATGAAGCCATACCAAACGACGAGCGTGACACCACGAT
GCCTACAGCAATGGCAACAACGTTGCGCAAACTATTAACTGGCGAACTAC
TTACTCTAGCTTCCCGGCAACAATTAATAGACTGGATGGAGGCGGATAAA
GTTGCAGGACCACTTCTGCGCTCGGCCCTTCCGGCTGGCTGGTTTATTGC
TGATAAATCTGGAGCCGGTGAGCGTGGGTCTCGCGGTATCATTGCAGCAC
TGGGGCCAGATGGTAAGCCCTCCCGTATCGTAGTTATCTACACGACGGGG
AGTCAGGCAACTATGGATGAACGAAATAGACAGATCGCTGAGATAGGTGC
CTCACTGATTAAGCATTGGTAACTGTCAGACCAAGTTTACTCATATATAC
TTTAGATTGATTTAAAACTTCATTTTTAATTTAAAAGGATCTAGGTGAAG
ATCCTTTTTGATAATCTCATGACCAAAATCCCTTAACGTGAGTTTTCGTT
CCACTGAGCGTCAGACCCCGTAGAAAAGATCAAAGGATCTTCTTGAGATC
CTTTTTTTCTGCGCGTAATCTGCTGCTTGCAAACAAAAAAACCACCGCTA
CCAGCGGTGGTTTGTTTGCCGGATCAAGAGCTACCAACTCTTTTTCCGAA
GGTAACTGGCTTCAGCAGAGCGCAGATACCAAATACTGTCCTTCTAGTGT
AGCCGTAGTTAGGCCACCACTTCAAGAACTCTGTAGCACCGCCTACATAC
CTCGCTCTGCTAATCCTGTTACCAGTGGCTGCTGCCAGTGGCGATAAGTC
GTGTCTTACCGGGTTGGACTCAAGACGATAGTTACCGGATAAGGCGCAGC
GGTCGGGCTGAACGGGGGGTTCGTGCACACAGCCCAGCTTGGAGCGAACG
ACCTACACCGAACTGAGATACCTACAGCGTGAGCTATGAGAAAGCGCCAC
GCTTCCCGAAGGGAGAAAGGCGGACAGGTATCCGGTAAGCGGCAGGGTCG
GAACAGGAGAGCGCACGAGGGAGCTTCCAGGGGGAAACGCCTGGTATCTT
TATAGTCCTGTCGGGTTTCGCCACCTCTGACTTGAGCGTCGATTTTTGTG
```

```
ATGCTCGTCAGGGGGGCGGAGCCTATGGAAAAACGCCAGCAACGCGGCCT

TTTTACGGTTCCTGGCCTTTTGCTGGCCTTTTGCTCACATGTTCTTTCCT

GCGTTATCCCCTGATTCTGTGGATAACCGTATTACCGCCTTTGAGTGAGC

TGATACCGCTCGCCGCAGCCGAACGACCGAGCGCAGCGAGTCAGTGAGCG

AGGAAGCGGAAGAGCGCCTGATGCGGTATTTTCTCCTTACGCATCTGTGC

GGTATTTCACACCGCATATG
```

Example 6

An artificial typhoid toxin operon lacking sty and ttsA with introduced cloning sites FLAG epitope and GGGGS (×3) SEQ ID NO.: 008 linker at the C-terminus of cldtB.

An artificial, inducible typhoid toxin operon lacking sty and ttsA and containing introduced cloning sites FLAG epitope and GGGGS(×3) SEQ ID NO.: 008 linker at the C-terminus as shown in FIG. 2D, is generated by multiple overlapping PCR and restriction endonuclease cloning steps and synthetic biology known to those skilled in the art. The operon is capable of being induced with an inducing agent, in the present instance, arabinose. As compared with FIG. 2B, the artificial operon now contains an artificial, in-frame restriction endonuclease linker containing SexAl, HindIII and Xbal the FLAG epitope and a GGGGS(×3) SEQ ID NO.: 008 flexible linker. The complete sequence of the arabinose inducible plasmid capable of expressing the construct with a cldtB start codon at 351 through codon at 1160 (without a stop), FLAG from 1170-1193, and GGGGS(×3) SEQ ID NO.: 008 from 1194-1238, pltB start at 1278 and stop at 1691 and pltA 1708-2436:

```
                                              SEQ ID NO.: 009
ggggGCGGCCGCaagaaaccaattgtccatattgcatcagacattgccgt cactgcgtcttttactggctcttctcgctaaccaaaccggtaacccgct tattaaaagcattctgtaacaaagcgggaccaaagccatgacaaaaacgc gtaacaaaagtgtctataatcacggcagaaaagtccacattgattatttg cacggcgtcacactttgctatgccatagcattttatccataagattagc ggatcctacctgacgcttttatcgcaactctctactgtttctccatacc cgttttttgggctagcgaattcgagctcggtacccaggaggaattcaCC atgGTCaaaaaacctgttttttccttctgaccatgatcatctgcagcta tatttcttttgcctgcgctaatatcagtgactacaaagttatgacctgga atcttcagggctcttcagcatctacagaaagtaaatggaatgtcaatgtc agacagcttttaagcggtactgccggtgtggatattcttatggtacagga ggccggtgctgttcccacctcagcggttcctaccggacgacatattcagc cttttggagtgggtattcccattgatgaatacacctggaatctcggaacc accagccgtcaggatataagatatatctactactcggctattgatgttgg agcacgccgtgttaatctggcaatagtttccagacaaagagcggataatg tttatgtcttgcgtccgacaactgtcgcatctcgcccgtcattggcatc ggactgggtaatgatgttttttctgacagcgcacgcactggctagtggagg tccggatgctgcagctattgtcagggttaccattaatttttttagacaac ctcagatgcggcatttatcctggtttcttgccggggattttaatcgcagc ccagacagacttgaaaatgacctgatgactgagcatctggaacgagttgt agccgtactcgcacctacagaacccacgcaaattagcggtggtattttag attatgggtcattgtcgatcgagcaccttattcacaaagggtcgaagca ttacgtaatccacaactcgcttctgatcattatcccgtagccttttggc acgaagctgtaTAccaggtgattataaagatgacgatgacaaaggcggtg gcggtagcggcggtggcggttctggcggtggcggtagtaagcttGGGtct agaTAGgtcgacgtacAGGAgagtagtATGTATATAAATAAGTTTGTGCC

TGTTTATACATTATTAATTCTCATTTATTCTTTTAATGCCAGCGCTGAGT

GGACAGGAGATAATACGAACGCCTATTACTCAGACGAAGTTATCAGTGAA

TTACATGTTGGTCAGATAGATACTAGTCCTTATTTTTGCATAAAAACGGT

TAAAGCTAACGGTAGTGGTACACCAGTTGTTGCATGTGCGGTATCAAAGC

AGAGCATATGGGCGCCCTCCTTTAAAGAACTTCTTGATCAGGCAAGATAT

TTTTACAGTACAGGGCAATCCGTAAGGATTCATGTTCAAAAAAATATCTG

GACCTATCCGCTTTTTGTTAATACCTTTTCAGCAAATGCTCTTGTGGGAC

TATCATCGTGCAGTGCGACACAATGCTTTGGACCCAAGTAAgaggggaga agaaataATGAAAAAGTTAATATTCTTAACCTTATCTATAGTTAGCTTTA

ATAACTATGCTGTAGATTTTGTGTATCGTGTGGACTCAACCCCGCCGGAC

GTTATTTTCGCGATGGGTTTTCACTACTTGGGTATAACCGTAACTTTCA

GCAATTTATTAGTGGAAGGTCATGTAGTGGTGGAAGTAGTGACAGTCGCT

ATATTGCAACAACCTCAAGTGTTAATCAAACATATGCTATAGCCAGAGCG

TACTATTCTCGCTCAACATTCAAAGGTAATTTATACAGATATCAGATTCG

TGCAGATAATAATTTCTACAGCTTGCTCCCATCCATCACCTATCTGGAAA

CGCAAGGTGGTCACTTTAATGCTTATGAAAAAACGATGATGCGATTGCAA

AGAGAGTATGTTTCCACATTATCTATTTTACCCGAGAATATTCAAAAGGC

CGTGGCGCTAGTTTATGATAGCGCAACCGGTCTGGTAAAGGATGGTGTAA

GCACAATGAATGCCAGTTATTTAGGTTTAAGCACTACGTCTAATCCTGGT

GTGATACCTTTTCTTCCGGAACCGCAGACGTATACCCAACAACGAATTGA

TGCATTCGGCCCATTAATAAGTTCATGCTTTTCAATAGGTAGCGTATGTC

AGTCACATCGAGGGCAAAGAGCTGACGTATACAACATGTCTTTTTATGAT

GCAAGACCTGTAATAGAACTTATACTTTCTAAATAAatgaaacttaccta tgttgccGCATGCAAGCTAGCTTGGCTGTTTTGGCGGATGAGAGAAGATT

TTCAGCCTGATACAGATTAAATCAGAACGCAGAAGCGGTCTGATAAAACA

GAATTTGCCTGGCGGCAGTAGCGCGGTGGTCCCACCTGACCCCATGCCGA

ACTCAGAAGTGAAACGCCGTAGCGCCGATGGTAGTGTGGGGTCTCCCCAT

GCGAGAGTAGGGAACTGCCAGGCATCAAATAAAACGAAAGGCTCAGTCGA

AAGACTGGGCCTTTCGTTTTATCTGTTGTTTGTCGGTGAACGCTCTCCTG

AGTAGGACAAATCCGCCGGGAGCGGATTTGAACGTTGCGAAGCAACGGCC

CGGAGGGTGGCGGGCAGGACGCCCGCCATAAACTGCCAGGCATCAAATTA

AGCAGAAGGCCATCCTGACGGATGGCCTTTTTGCGTTTCTACAAACTCTT

TTTGTTTATTTTTCTAAATACATTCAAATATGTATCCGCTCATGAGACAA
```

```
TAACCCTGATAAATGCTTCAATAATATTGAAAAAGGAAGAGTATGAGTAT
TCAACATTTCCGTGTCGCCCTTATTCCCTTTTTTGCGGCATTTTGCCTTC
CTGTTTTTGCTCACCCAGAAACGCTGGTGAAAGTAAAAGATGCTGAAGAT
CAGTTGGGTGCACGAGTGGGTTACATCGAACTGGATCTCAACAGCGGTAA
GATCCTTGAGAGTTTTCGCCCCGAAGAACGTTTTCCAATGATGAGCACTT
TTAAAGTTCTGCTATGTGGCGCGGTATTATCCCGTGTTGACGCCGGGCAA
GAGCAACTCGGTCGCCGCATACACTATTCTCAGAATGACTTGGTTGAGTA
CTCACCAGTCACAGAAAAGCATCTTACGGATGGCATGACAGTAAGAGAAT
TATGCAGTGCTGCCATAACCATGAGTGATAACACTGCGGCCAACTTACTT
CTGACAACGATCGGAGGACCGAAGGAGCTAACCGCTTTTTTGCACAACAT
GGGGGATCATGTAACTCGCCTTGATCGTTGGGAACCGGAGCTGAATGAAG
CCATACCAAACGACGAGCGTGACACCACGATGCCTACAGCAATGGCAACA
ACGTTGCGCAAACTATTAACTGGCAACTACTTACTCTAGCTTCCCGGCA
ACAATTAATAGACTGGATGGAGGCGGATAAAGTTGCAGGACCACTTCTGC
GCTCGGCCCTTCCGGCTGGCTGGTTTATTGCTGATAAATCTGGAGCCGGT
GAGCGTGGGTCTCGCGGTATCATTGCAGCACTGGGGCCAGATGGTAAGCC
CTCCCGTATCGTAGTTATCTACACGACGGGGAGTCAGGCAACTATGGATG
AACGAAATAGACAGATCGCTGAGATAGGTGCCTCACTGATTAAGCATTGG
TAACTGTCAGACCAAGTTTACTCATATATACTTTAGATTGATTTAAAACT
TCATTTTTAATTTAAAAGGATCTAGGTGAAGATCCTTTTTGATAATCTCA
TGACCAAAATCCCTTAACGTGAGTTTTCGTTCCACTGAGCGTCAGACCCC
GTAGAAAAGATCAAAGGATCTTCTTGAGATCCTTTTTTTCTGCGCGTAAT
CTGCTGCTTGCAAACAAAAAAACCACCGCTACCAGCGGTGGTTTGTTTGC
CGGATCAAGAGCTACCAACTCTTTTTCCGAAGGTAACTGGCTTCAGCAGA
GCGCAGATACCAAATACTGTCCTTCTAGTGTAGCCGTAGTTAGGCCACCA
CTTCAAGAACTCTGTAGCACCGCCTACATACCTCGCTCTGCTAATCCTGT
TACCAGTGGCTGCTGCCAGTGGCGATAAGTCGTGTCTTACCGGGTTGGAC
TCAAGACGATAGTTACCGGATAAGGCGCAGCGGTCGGGCTGAACGGGGGG
TTCGTGCACACAGCCCAGCTTGGAGCGAACGACCTACACCGAACTGAGAT
ACCTACAGCGTGAGCTATGAGAAAGCGCCACGCTTCCCGAAGGGAGAAAG
GCGGACAGGTATCCGGTAAGCGGCAGGGTCGGAACAGGAGAGCGCACGAG
GGAGCTTCCAGGGGAAACGCCTGGTATCTTTATAGTCCTGTCGGGTTTC
GCCACCTCTGACTTGAGCGTCGATTTTTGTGATGCTCGTCAGGGGGCGG
AGCCTATGGAAAAACGCCAGCAACGCGGCCTTTTTACGGTTCCTGGCCTT
TTGCTGGCCTTTTGCTCACATGTTCTTTCCTGCGTTATCCCCTGATTCTG
TGGATAACCGTATTACCGCCTTTGAGTGAGCTGATACCGCTCGCCGCAGC
CGAACGACCGAGCGCAGCGAGTCAGTGAGCGAGGAAGCGGAAGAGCGCCT
GATGCGGTATTTTCTCCTTACGCATCTGTGCGGTATTTCACACCGCATAT
G
```

Example 7

Apoptin C-terminal fusions with typhoid toxin cldtB.

An artificial, inducible typhoid toxin operon lacking sty and ttsA and containing introduced FLAG epitope, GGGGS (×3) SEQ ID NO.: 008 linker and HindIII and Xbal is used to insert apoptin, TAT-apoptin, and apoptin fragments as shown in FIG. 2E as generated by PCR and restriction endonuclease-based cloning methods and synthetic biology known to those skilled in the art. Fragments consisting of either 1) apoptin 1-121, 2) apoptin 33-121, 3) apoptin 82-121, 4) apoptin 97-121, 5) apoptin 106-121, 6) apoptin 111-121 or 7) apoptin 1-31 linked ot 83-121. By way of example complete sequence of the arabinose inducible plasmid capable of expressing the TAT-apoptin construct as a cldtB fusion, with TAT-apoptin inserted in-frame within the HindIII and Xbal sites introduced into typhoid toxin cldtB, with the TAT-apoptin coding sequence from 1245-1646:

```
                                        SEQ ID NO.: 010
gggGGCGGCCGCaagaaaccaattgtccatattgcatcagacattgccgt
cactgcgtcttttactggctcttctcgctaaccaaaccggtaacccgct
tattaaaagcattctgtaacaaagcgggaccaaagccatgacaaaaacgc
gtaacaaaagtgtctataatcacggcagaaaagtccacattgattatttg
cacggcgtcacactttgctatgccatagcattttttatccataagattagc
ggatcctacctgacgcttttttatcgcaactctctactgtttctccatacc
cgttttttttgggctagcgaattcgagctcggtacccaggaggaattcaCC
atgGTCaaaaaacctgttttttttccttctgaccatgatcatctgcagcta
tatttcttttgcctgcgctaatatcagtgactacaaagttatgacctgga
atcttcagggctcttcagcatctacagaaagtaaatggaatgtcaatgtc
agacagcttttaagcggtactgccggtgtggatattcttatggtacagga
ggccggtgctgttcccacctcagcggttcctaccggacgacatattcagc
cttttggagtgggtattcccattgatgaatacacctggaatctcggaacc
accagccgtcaggatataagatatatctactactcggctattgatgttgg
agcacgccgtgttaatctggcaatagtttccagacaaagagcggataatg
tttatgtcttgcgtccgacaactgtcgcatctcgcccgtcattggcatc
ggactgggtaatgatgttttttctgacagcgcacgcactggctagtggagg
tccggatgctgcagctattgtcagggttaccattaatttttttagacaac
ctcagatgcggcatttatcctggtttcttgccggggattttaatcgcagc
ccagacagacttgaaaatgacctgatgactgagcatctggaacgagttgt
agccgtactcgcacctacagaacccacgcaaattagcggtggtattttag
attatggggtcattgtcgatcgagcaccttattcacaaagggtcgaagca
ttacgtaatccacaactcgcttctgatcattatcccgtagccttttggc
acgaagctgtaTAccaggtgattataaagatgacgatgacaaaggcggtg
gcggtagcggcggtggcggttctggcggtggcggtagtaagcttATGGCA
TACGGTCGCAAGAAACGTCGTCAACGCCGCCGCATGAACGCCCTGCAAGA
AGACACGCCGCCGGGTCCGAGCACGGTTTTTCGTCCGCCGACCAGCTCTC
GCCCGCTGGAAACGCCGCATTGCCGTGAAATTCGCATCGGCATTGCAGGT
```

-continued
```
ATCACCATTACGCTGTCTCTGTGCGGCTGTGCAAACGCACGTGCACCGAC
CCTGCGCTCCGCTACGGCGGATAACAGTGAATCCACCGGTTTTAAAAATG
TGCCGGATCTGCGTACGGACCAGCCGAAGCCGCCGTCAAAAAAGCGTTCG
TGTGACCCGAGCGAATATCGCGTTAGCGAACTGAAAGAATCTCTGATTAC
CACGACCCCGTCCCGTCCGCGCACCGCaaaACGCCGCATCCGTCTGTCTA
GATAGgtcgacgtacAGGAgagtagtATGTATATAAATAAGTTTGTGCCT
GTTTATACATTATTAATTCTCATTTATTCTTTTAATGCCAGCGCTGAGTG
GACAGGAGATAATACGAACGCCTATTACTCAGACGAAGTTATCAGTGAAT
TACATGTTGGTCAGATAGATACTAGTCCTTATTTTTGCATAAAAACGGTT
AAAGCTAACGGTAGTGGTACACCAGTTGTTGCATGTGCGGTATCAAAGCA
GAGCATATGGGCGCCCTCCTTTAAAGAACTTCTTGATCAGGCAAGATATT
TTTACAGTACAGGGCAATCCGTAAGGATTCATGTTCAAAAAAATATCTGG
ACCTATCCGCTTTTTGTTAATACCTTTTCAGCAAATGCTCTTGTGGGACT
ATCATCGTGCAGTGCGACACAATGCTTTGGACCCAAGTAAgaggggagaa
gaaataATGAAAAAGTTAATATTCTTAACCTTATCTATAGTTAGCTTTAA
TAACTATGCTGTAGATTTTGTGTATCGTGTGGACTCAACCCCGCCGGACG
TTATTTTTCGCGATGGGTTTTCACTACTTGGGTATAACCGTAACTTTCAG
CAATTTATTAGTGGAAGGTCATGTAGTGGTGGAAGTAGTGACAGTCGCTA
TATTGCAACAACCTCAAGTGTTAATCAAACATATGCTATAGCCAGAGCGT
ACTATTCTCGCTCAACATTCAAAGGTAATTTATACAGATATCAGATTCGT
GCAGATAATAATTTCTACAGCTTGCTCCCATCCATCACCTATCTGGAAAC
GCAAGGTGGTCACTTTAATGCTTATGAAAAAACGATGATGCGATTGCAAA
GAGAGTATGTTTCCACATTATCTATTTTACCCGAGAATATTCAAAAGGCC
GTGGCGCTAGTTTATGATAGCGCAACCGGTCTGGTAAAGGATGGTGTAAG
CACAATGAATGCCAGTTATTTAGGTTTAAGCACTACGTCTAATCCTGGTG
TGATACCTTTTCTTCCGGAACCGCAGACGTATACCCAACAACGAATTGAT
GCATTCGGCCCATTAATAAGTTCATGCTTTTCAATAGGTAGCGTATGTCA
GTCACATCGAGGGCAAAGAGCTGACGTATACAACATGTCTTTTTATGATG
CAAGACCTGTAATAGAACTTATACTTTCTAAATAAatgaaacttacctat
gttgccGCATGCAAGCTAGCTTGGCTGTTTTGGCGGATGAGAGAAGATTT
TCAGCCTGATACAGATTAAATCAGAACGCAGAAGCGGTCTGATAAAACAG
AATTTGCCTGGCGGCAGTAGCGCGGTGGTCCCACCTGACCCCATGCCGAA
CTCAGAAGTGAAACGCCGTAGCGCCGATGGTAGTGTGGGGTCTCCCCATG
CGAGAGTAGGGAACTGCCAGGCATCAAATAAAACGAAAGGCTCAGTCGAA
AGACTGGGCCTTTCGTTTTATCTGTTGTTTGTCGGTGAACGCTCTCCTGA
GTAGGACAAATCCGCCGGGAGCGGATTTGAACGTTGCGAAGCAACGGCCC
GGAGGGTGGCGGGCAGGACGCCCGCCATAAACTGCCAGGCATCAAATTAA
GCAGAAGGCCATCCTGACGGATGGCCTTTTTGCGTTTCTACAAACTCTTT
TTGTTTATTTTTCTAAATACATTCAAATATGTATCCGCTCATGAGACAAT
AACCCTGATAAATGCTTCAATAATATTGAAAAGGAAGAGTATGAGTATT
CAACATTTCCGTGTCGCCCTTATTCCCTTTTTTGCGGCATTTTGCCTTCC
TGTTTTTGCTCACCCAGAAACGCTGGTGAAAGTAAAAGATGCTGAAGATC
AGTTGGGTGCACGAGTGGGTTACATCGAACTGGATCTCAACAGCGGTAAG
ATCCTTGAGAGTTTTCGCCCCGAAGAACGTTTTCCAATGATGAGCACTTT
TAAAGTTCTGCTATGTGGCGCGGTATTATCCCGTGTTGACGCCGGGCAAG
AGCAACTCGGTCGCCGCATACACTATTCTCAGAATGACTTGGTTGAGTAC
TCACCAGTCACAGAAAAGCATCTTACGGATGGCATGACAGTAAGAGAATT
ATGCAGTGCTGCCATAACCATGAGTGATAACACTGCGGCCAACTTACTTC
TGACAACGATCGGAGGACCGAAGGAGCTAACCGCTTTTTTGCACAACATG
GGGGATCATGTAACTCGCCTTGATCGTTGGGAACCGGAGCTGAATGAAGC
CATACCAAACGACGAGCGTGACACCACGATGCCTACAGCAATGGCAACAA
CGTTGCGCAAACTATTAACTGGCGAACTACTTACTCTAGCTTCCCGGCAA
CAATTAATAGACTGGATGGAGGCGGATAAAGTTGCAGGACCACTTCTGCG
CTCGGCCCTTCCGGCTGGCTGGTTTATTGCTGATAAATCTGGAGCCGGTG
AGCGTGGGTCTCGCGGTATCATTGCAGCACTGGGGCCAGATGGTAAGCCC
TCCCGTATCGTAGTTATCTACACGACGGGGAGTCAGGCAACTATGGATGA
ACGAAATAGACAGATCGCTGAGATAGGTGCCTCACTGATTAAGCATTGGT
AACTGTCAGACCAAGTTTACTCATATATACTTTAGATTGATTTAAAACTT
CATTTTTAATTTAAAAGGATCTAGGTGAAGATCCTTTTTGATAATCTCAT
GACCAAAATCCCTTAACGTGAGTTTTCGTTCCACTGAGCGTCAGACCCCG
TAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCC
GGATCAAGAGCTACCAACTCTTTTTCCGAAGGTAACTGGCTTCAGCAGAG
CGCAGATACCAAATACTGTCCTTCTAGTGTAGCCGTAGTTAGGCCACCAC
TTCAAGAACTCTGTAGCACCGCCTACATACCTCGCTCTGCTAATCCTGTT
ACCAGTGGCTGCTGCCAGTGGCGATAAGTCGTGTCTTACCGGGTTGGACT
CAAGACGATAGTTACCGGATAAGGCGCAGCGGTCGGGCTGAACGGGGGGT
TCGTGCACACAGCCCAGCTTGGAGCGAACGACCTACACCGAACTGAGATA
CCTACAGCGTGAGCTATGAGAAAGCGCCACGCTTCCCGAAGGGAGAAAGG
CGGACAGGTATCCGGTAAGCGGCAGGGTCGGAACAGGAGAGCGCACGAGG
GAGCTTCCAGGGGGAAACGCCTGGTATCTTTATAGTCCTGTCGGGTTTCG
CCACCTCTGACTTGAGCGTCGATTTTTGTGATGCTCGTCAGGGGGCGGA
GCCTATGGAAAAACGCCAGCAACGCGGCCTTTTTACGGTTCCTGGCCTTT
TGCTGGCCTTTTGCTCACATGTTCTTTCCTGCGTTATCCCCTGATTCTGT
GGATAACCGTATTACCGCCTTTGAGTGAGCTGATACCGCTCGCCGCAGCC
GAACGACCGAGCGCAGCGAGTCAGTGAGCGAGGAAGCGGAAGAGCGCCTG
ATGCGGTATTTTCTCCTTACGCATCTGTGCGGTATTTCACACCGCATATG
```

Example 8

N-terminal fusions with typhoid toxin cldtB.

An artificial, inducible typhoid toxin operon lacking sty and ttsA and containing introduced FLAG epitope, GGGGS (×3) SEQ ID NO.: 008 linker and HindIII and XbaI is used to insert functional peptides in frame (e.g., apoptin, TAT-apoptin, and apoptin fragments) as shown in FIG. 3B as generated by PCR and restriction endonuclease-based cloning methods and synthetic biology known to those skilled in the art. For example, two separate PCR primer sets that generate N-terminal restriction sites (HindIII (H3) Xbal and Clal) for cloning typhoid/paratyphoid cldtB are

```
paratyphi A NcoI_F1:
                                        SEQ ID NO.: 011
5'-TACGCCATGGTCAAAAAACCTGTTTTTTTCCTTCTGACC-3'
and HindIII_Xbal_Clal-R1:
                                        SEQ ID NO.: 012
5'-CGATCCCTCTAGACCCAAGCTTGTCACTGATATTAGCGCAGGC-3'
(set 1)
and

HindIII_Xbal_Clal-F1:
                                         SEQ ID NO.: 13
5'-GCTTGGGTCTAGAGGGATCGATTACAAAGTTATGACCTGGAATCTTC AG-3'
and cldtB_stop_Xbal_Sall-R1:
                                         SEQ ID NO.: 14
5'- GATCGTCGACTTATCTAGATCATTAACAGCTTCGTGCCA-3'
(set 2).
```

The two sets are used for separate PCRs (for example, using the DNA of FIG. 2B as a template) followed by overlapping PCR and cloning into the Ncol and Xbal restriction endonuclease sites (13-350=arabinose promoter; 351-1187=cldtB; 1210-1213=RBS pltB; 1221-1634=pltB; 1651-2379=pltA).

```
                                        SEQ ID NO.: 015
gggGGCGGCCGCaagaaaccaattgtccatattgcatcagacattgccgt cactgcgtcttttactggctcttctcgctaaccaaaccggtaaccccgct tattaaaagcattctgtaacaaagcgggaccaaagccatgacaaaaacgc gtaacaaaagtgtctataatcacggcagaaaagtccacattgattatttg cacggcgtcacactttgctatgccatagcatttttatccataagattagc ggatcctacctgacgctttttatcgcaactctctactgtttctccatacc cgtttttttgggctagcgaattcgagctcggtacccaggaggaattcaCC

ATGGTCAAAAAACCTGTTTTTTTCCTTCTGACCATGATCATCTGCAGCTA

TATTTCTTTTGCCTGCGCTAATATCAGTGACaagcttgggtctagaggga tcgatTACAAAGTTATGACCTGGAATCTTCAGGGCTCTTCAGCATCTACA

GAAAGTAAATGGAATGTCAATGTCAGACAGCTTTTAAGCGGTACTGCCGG

TGTGGATATTCTTATGGTACAGGAGGCCGGTGCTGTTCCCACCTCAGCGG

TTCCTACCGGACGACATATTCAGCCTTTTGGAGTGGGTATTCCCATTGAT

GAATACACCTGGAATCTCGGAACCACCAGCCGTCAGGATATAAGATATAT

CTACTACTCGGCTATTGATGTTGGAGCACGCCGTGTTAATCTGGCAATAG

TTTCCAGACAAAGAGCGGATAATGTTTATGTCTTGCGTCCGACAACTGTC

GCATCTCGCCCCGTCATTGGCATCGGACTGGGTAATGATGTTTTTCTGAC

AGCGCACGCACTGGCTAGTGGAGGTCCGGATGCTGCAGCTATTGTCAGGG

TTACCATTAATTTTTTTAGACAACCTCAGATGCGGCATTTATCCTGGTTT
```

-continued

```
CTTGCCGGGGATTTTAATCGCAGCCCAGACAGACTTGAAAATGACCTGAT

GACTGAGCATCTGGAACGAGTTGTAGCCGTACTCGCACCTACAGAACCCA

CGCAAATTAGCGGTGGTATTTTAGATTATGGGGTCATTGTCGATCGAGCA

CCTTATTCACAAAGGGTCGAAGCATTACGTAATCCACAACTCGCTTCTGA

TCATTATCCCGTAGCCTTTTTGGCACGAAGCTGTTAAtgaTCTAGATAAG

TCGACgtacAGGAgagtagtATGTATATAAATAAGTTTGTGCCTGTTTAT

ACATTATTAATTCTCATTTATTCTTTTAATGCCAGCGCTGAGTGGACAGG

AGATAATACGAACGCCTATTACTCAGACGAAGTTATCAGTGAATTACATG

TTGGTCAGATAGATACTAGTCCTTATTTTTGCATAAAAACGGTTAAAGCT

AACGGTAGTGGTACACCAGTTGTTGCATGTGCGGTATCAAAGCAGAGCAT

ATGGGCGCCCTCCTTTAAAGAACTTCTTGATCAGGCAAGATATTTTTACA

GTACAGGGCAATCCGTAAGGATTCATGTTCAAAAAAATATCTGGACCTAT

CCGCTTTTTGTTAATACCTTTTCAGCAAATGCTCTTGTGGGACTATCATC

GTGCAGTGCGACACAATGCTTTGGACCCAAGTAAgaggggagaagaaata

ATGAAAAAGTTAATATTCTTAACCTTATCTATAGTTAGCTTTAATAACTA

TGCTGTAGATTTTGTGTATCGTGTGGACTCAACCCCGCCGGACGTTATTT

TTCGCGATGGGTTTTCACTACTTGGGTATAACCGTAACTTTCAGCAATTT

ATTAGTGGAAGGTCATGTAGTGGTGGAAGTAGTGACAGTCGCTATATTGC

AACAACCTCAAGTGTTAATCAAACATATGCTATAGCCAGAGCGTACTATT

CTCGCTCAACATTCAAAGGTAATTTATACAGATATCAGATTCGTGCAGAT

AATAATTTCTACAGCTTGCTCCCATCCATCACCTATCTGGAAACGCAAGG

TGGTCACTTTAATGCTTATGAAAAAACGATGATGCGATTGCAAAGAGAGT

ATGTTTCCACATTATCTATTTTACCCGAGAATATTCAAAAGGCCGTGGCG

CTAGTTTATGATAGCGCAACCGGTCTGGTAAAGGATGGTGTAAGCACAAT

GAATGCCAGTTATTTAGGTTTAAGCACTACGTCTAATCCTGGTGTGATAC

CTTTTCTTCCGGAACCGCAGACGTATACCCAACAACGAATTGATGCATTC

GGCCCATTAATAAGTTCATGCTTTTCAATAGGTAGCGTATGTCAGTCACA

TCGAGGGCAAAGAGCTGACGTATACAACATGTCTTTTTATGATGCAAGAC

CTGTAATAGAACTTATACTTTCTAAATAAatgaaacttacctatgttgcc

GCATGCAAGCTAGCTTGGCTGTTTTGGCGGATGAGAGAAGATTTTCAGCC

TGATACAGATTAAATCAGAACGCAGAAGCGGTCTGATAAAACAGAATTTG

CCTGGCGGCAGTAGCGCGGTGGTCCCACCTGACCCCATGCCGAACTCAGA

AGTGAAACGCCGTAGCGCCGATGGTAGTGTGGGGTCTCCCCATGCGAGAG

TAGGGAACTGCCAGGCATCAAATAAAACGAAAGGCTCAGTCGAAAGACTG

GGCCTTTCGTTTTATCTGTTGTTTGTCGGTGAACGCTCTCCTGAGTAGGA

CAAATCCGCCGGGAGCGGATTTGAACGTTGCGAAGCAACGGCCCGGAGGG

TGGCGGGCAGGACGCCCGCCATAAACTGCCAGGCATCAAATTAAGCAGAA

GGCCATCCTGACGGATGGCCTTTTTGCGTTTCTACAAACTCTTTTTGTTT

ATTTTTCTAAATACATTCAAATATGTATCCGCTCATGAGACAATAACCCT

GATAAATGCTTCAATAATATTGAAAAAGGAAGAGTATGAGTATTCAACAT
```

-continued
TTCCGTGTCGCCCTTATTCCCTTTTTTGCGGCATTTTGCCTTCCTGTTTT
TGCTCACCCAGAAACGCTGGTGAAAGTAAAAGATGCTGAAGATCAGTTGG
GTGCACGAGTGGGTTACATCGAACTGGATCTCAACAGCGGTAAGATCCTT
GAGAGTTTTCGCCCCGAAGAACGTTTTCCAATGATGAGCACTTTTAAAGT
TCTGCTATGTGGCGCGGTATTATCCCGTGTTGACGCCGGGCAAGAGCAAC
TCGGTCGCCGCATACACTATTCTCAGAATGACTTGGTTGAGTACTCACCA
GTCACAGAAAAGCATCTTACGGATGGCATGACAGTAAGAGAATTATGCAG
TGCTGCCATAACCATGAGTGATAACACTGCGGCCAACTTACTTCTGACAA
CGATCGGAGGACCGAAGGAGCTAACCGCTTTTTTGCACAACATGGGGGAT
CATGTAACTCGCCTTGATCGTTGGGAACCGGAGCTGAATGAAGCCATACC
AAACGACGAGCGTGACACCACGATGCCTACAGCAATGGCAACAACGTTGC
GCAAACTATTAACTGGCGAACTACTTACTCTAGCTTCCCGGCAACAATTA
ATAGACTGGATGGAGGCGGATAAAGTTGCAGGACCACTTCTGCGCTCGGC
CCTTCCGGCTGGCTGGTTTATTGCTGATAAATCTGGAGCCGGTGAGCGTG
GGTCTCGCGGTATCATTGCAGCACTGGGGCCAGATGGTAAGCCCTCCCGT
ATCGTAGTTATCTACACGACGGGGAGTCAGGCAACTATGGATGAACGAAA
TAGACAGATCGCTGAGATAGGTGCCTCACTGATTAAGCATTGGTAACTGT
CAGACCAAGTTTACTCATATATACTTTAGATTGATTTAAAACTTCATTTT
TAATTTAAAAGGATCTAGGTGAAGATCCTTTTTGATAATCTCATGACCAA
AATCCCTTAACGTGAGTTTTCGTTCCACTGAGCGTCAGACCCCGTAGAAA
AGATCAAAGGATCTTCTTGAGATCCTTTTTTTCTGCGCGTAATCTGCTGC
TTGCAAACAAAAAAACCACCGCTACCAGCGGTGGTTTGTTTGCCGGATCA
AGAGCTACCAACTCTTTTTCCGAAGGTAACTGGCTTCAGCAGAGCGCAGA
TACCAAATACTGTCCTTCTAGTGTAGCCGTAGTTAGGCCACCACTTCAAG
AACTCTGTAGCACCGCCTACATACCTCGCTCTGCTAATCCTGTTACCAGT
GGCTGCTGCCAGTGGCGATAAGTCGTGTCTTACCGGGTTGGACTCAAGAC
GATAGTTACCGGATAAGGCGCAGCGGTCGGGCTGAACGGGGGGTTCGTGC
ACACAGCCCAGCTTGGAGCGAACGACCTACACCGAACTGAGATACCTACA
GCGTGAGCTATGAGAAAGCGCCACGCTTCCCGAAGGGAGAAAGGCGGACA
GGTATCCGGTAAGCGGCAGGGTCGGAACAGGAGAGCGCACGAGGGAGCTT
CCAGGGGGAAACGCCTGGTATCTTTATAGTCCTGTCGGGTTTCGCCACCT
CTGACTTGAGCGTCGATTTTTGTGATGCTCGTCAGGGGGCGGAGCCTAT
GGAAAAACGCCAGCAACGCGGCCTTTTTACGGTTCCTGGCCTTTTGCTGG
CCTTTTGCTCACATGTTCTTTCCTGCGTTATCCCCTGATTCTGTGGATAA
CCGTATTACCGCCTTTGAGTGAGCTGATACCGCTCGCCGCAGCCGAACGA
CCGAGCGCAGCGAGTCAGTGAGCGAGGAAGCGGAAGAGCGCCTGATGCGG
TATTTTCTCCTTACGCATCTGTGCGGTATTTCACACCGCATATG

Example 9

N-terminal fusions with typhoid toxin cldtB containing a 3XFLAG epitope and a flexible linker.

The artificial, inducible typhoid toxin operon lacking sty and ttsA and containing introduced HindIII (H3) XbaI and ClaI of Example 8 is used to insert an in-frame 3XFLAG epitope (for immune identification and/or purification) and a flexible linker (GGGGS(×3), SEQ ID NO.: 008 as shown in FIG. 3C as generated by PCR and restriction endonuclease-based cloning methods and synthetic biology known to those skilled in the art (13-350=arabinose promoter; 351-1295=cldtB; 1318-1321=RBS pltB; 1329-1742=pltB; 1759-2487=pltA).

SEQ ID NO.: 016
gggGGCGGCCGCaagaaaccaattgtccatattgcatcagacattgccgt
cactgcgtcttttactggctcttctcgctaaccaaaccggtaaccccgct
tattaaaagcattctgtaacaaagcgggaccaaagccatgacaaaaacgc
gtaacaaaagtgtctataatcacggcagaaaagtccacattgattatttg
cacggcgtcacactttgctatgccatagcattttttatccataagattagc
ggatcctacctgacgcttttatcgcaactctctactgtttctccatacc
cgttttttgggctagcgaattcgagctcggtacccaggaggaattcaCC
ATGGTCAAAAAACCTGTTTTTTTCCTTCTGACCATGATCATCTGCAGCTA
TATTTCTTTTGCCTGCGCTAATATCAGTGACaagcttgggtctagagact
acaaagaccatgacggtgattataaagatcatgatatcgactacaaagat
gacgacgataaaGGCGGTGGCGGATCCGGCGGTGGCGGTTCTGGCGGTGG
CGGTAGTatcgatTACAAAGTTATGACCTGGAATCTTCAGGGCTCTTCAG
CATCTACAGAAAGTAAATGGAATGTCAATGTCAGACAGCTTTTAAGCGGT
ACTGCCGGTGTGGATATTCTTATGGTACAGGAGGCCGGTGCTGTTCCCAC
CTCAGCGGTTCCTACCGGACGACATATTCAGCCTTTTGGAGTGGGTATTC
CCATTGATGAATACACCTGGAATCTCGGAACCACCAGCCGTCAGGATATA
AGATATATCTACTACTCGGCTATTGATGTTGGAGCACGCCGTGTTAATCT
GGCAATAGTTTCCAGACAAAGAGCGGATAATGTTTATGTCTTGCGTCCGA
CAACTGTCGCATCTCGCCCCGTCATTGGCATCGGACTGGGTAATGATGTT
TTTCTGACAGCGCACGCACTGGCTAGTGGAGGTCCGGATGCTGCAGCTAT
TGTCAGGGTTACCATTAATTTTTTTAGACAACCTCAGATGCGGCATTTAT
CCTGGTTTCTTGCCGGGGATTTTAATCGCAGCCCAGACAGACTTGAAAAT
GACCTGATGACTGAGCATCTGGAACGAGTTGTAGCCGTACTCGCACCTAC
AGAACCCACGCAAATTAGCGGTGGTATTTTAGATTATGGGGTCATTGTCG
ATCGAGCACCTTATTCACAAAGGGTCGAAGCATTACGTAATCCACAACTC
GCTTCTGATCATTATCCCGTAGCCTTTTTGGCACGAAGCTGTTAAtgaTC
TAGATAAGTCGACgtacAGGAgagtagtATGTATATAAATAAGTTTGTGC
CTGTTTATACATTATTAATTCTCATTTATTCTTTTAATGCCAGCGCTGAG
TGGACAGGAGATAATACGAACGCCTATTACTCAGACGAAGTTATCAGTGA
ATTACATGTTGGTCAGATAGATACTAGTCCTTATTTTTGCATAAAAACGG
TTAAAGCTAACGGTAGTGGTACACCAGTTGTTGCATGTGCGGTATCAAAG
CAGAGCATATGGGCGCCCTCCTTTAAAGAACTTCTTGATCAGGCAAGATA
TTTTTACAGTACAGGGCAATCCGTAAGGATTCATGTTCAAAAAAATATCT
GGACCTATCCGCTTTTTGTTAATACCTTTTCAGCAAATGCTCTTGTGGGA
CTATCATCGTGCAGTGCGACACAATGCTTTGGACCCAAGTAAgaggggag

```
aagaaataATGAAAAAGTTAATATTCTTAACCTTATCTATAGTTAGCTTT
AATAACTATGCTGTAGATTTTGTGTATCGTGTGGACTCAACCCCGCCGGA
CGTTATTTTTCGCGATGGGTTTTCACTACTTGGGTATAACCGTAACTTTC
AGCAATTTATTAGTGGAAGGTCATGTAGTGGTGGAAGTAGTGACAGTCGC
TATATTGCAACAACCTCAAGTGTTAATCAAACATATGCTATAGCCAGAGC
GTACTATTCTCGCTCAACATTCAAAGGTAATTTATACAGATATCAGATTC
GTGCAGATAATAATTTCTACAGCTTGCTCCCATCCATCACCTATCTGGAA
ACGCAAGGTGGTCACTTTAATGCTTATGAAAAAACGATGATGCGATTGCA
AAGAGAGTATGTTTCCACATTATCTATTTTACCCGAGAATATTCAAAAGG
CCGTGGCGCTAGTTTATGATAGCGCAACCGGTCTGGTAAAGGATGGTGTA
AGCACAATGAATGCCAGTTATTTAGGTTTAAGCACTACGTCTAATCCTGG
TGTGATACCTTTCTTCCGGAACCGCAGACGTATACCCAACAACGAATTG
ATGCATTCGGCCCATTAATAAGTTCATGCTTTTCAATAGGTAGCGTATGT
CAGTCACATCGAGGGCAAAGAGCTGACGTATACAACATGTCTTTTTATGA
TGCAAGACCTGTAATAGAACTTATACTTTCTAAATAAatgaaacttacct
atgttgccGCATGCAAGCTAGCTTGGCTGTTTTGGCGGATGAGAGAAGAT
TTTCAGCCTGATACAGATTAAATCAGAACGCAGAAGCGGTCTGATAAAAC
AGAATTTGCCTGGCGGCAGTAGCGCGGTGGTCCCACCTGACCCCATGCCG
AACTCAGAAGTGAAACGCCGTAGCGCCGATGGTAGTGTGGGGTCTCCCCA
TGCGAGAGTAGGGAACTGCCAGGCATCAAATAAAACGAAAGGCTCAGTCG
AAAGACTGGGCCTTTCGTTTTATCTGTTGTTTGTCGGTGAACGCTCTCCT
GAGTAGGACAAATCCGCCGGGAGCGGATTTGAACGTTGCGAAGCAACGGC
CCGGAGGGTGGCGGGCAGGACGCCCGCCATAAACTGCCAGGCATCAAATT
AAGCAGAAGGCCATCCTGACGGATGGCCTTTTTGCGTTTCTACAAACTCT
TTTTGTTTATTTTTCTAAATACATTCAAATATGTATCCGCTCATGAGACA
ATAACCCTGATAAATGCTTCAATAATATTGAAAAAGGAAGAGTATGAGTA
TTCAACATTTCCGTGTCGCCCTTATTCCCTTTTTTGCGGCATTTTGCCTT
CCTGTTTTTGCTCACCCAGAAACGCTGGTGAAAGTAAAAGATGCTGAAGA
TCAGTTGGGTGCACGAGTGGGTTACATCGAACTGGATCTCAACAGCGGTA
AGATCCTTGAGAGTTTTCGCCCCGAAGAACGTTTTCCAATGATGAGCACT
TTTAAAGTTCTGCTATGTGGCGCGGTATTATCCCGTGTTGACGCCGGGCA
AGAGCAACTCGGTCGCCGCATACACTATTCTCAGAATGACTTGGTTGAGT
ACTCACCAGTCACAGAAAAGCATCTTACGGATGGCATGACAGTAAGAGAA
TTATGCAGTGCTGCCATAACCATGAGTGATAACACTGCGGCCAACTTACT
TCTGACAACGATCGGAGGACCGAAGGAGCTAACCGCTTTTTTGCACAACA
TGGGGGATCATGTAACTCGCCTTGATCGTTGGGAACCGGAGCTGAATGAA
GCCATACCAAACGACGAGCGTGACACCACGATGCCTACAGCAATGGCAAC
AACGTTGCGCAAACTATTAACTGGCGAACTACTTACTCTAGCTTCCCGGC
AACAATTAATAGACTGGATGGAGGCGGATAAAGTTGCAGGACCACTTCTG
CGCTCGGCCCTTCCGGCTGGCTGGTTTATTGCTGATAAATCTGGAGCCGG
TGAGCGTGGGTCTCGCGGTATCATTGCAGCACTGGGGCCAGATGGTAAGC
CCTCCCGTATCGTAGTTATCTACACGACGGGGAGTCAGGCAACTATGGAT
GAACGAAATAGACAGATCGCTGAGATAGGTGCCTCACTGATTAAGCATTG
GTAACTGTCAGACCAAGTTTACTCATATATACTTTAGATTGATTTAAAAC
TTCATTTTTAATTTAAAAGGATCTAGGTGAAGATCCTTTTTGATAATCTC
ATGACCAAAATCCCTTAACGTGAGTTTTCGTTCCACTGAGCGTCAGACCC
CGTAGAAAAGATCAAAGGATCTTCTTGAGATCCTTTTTTTCTGCGCGTAA
TCTGCTGCTTGCAAACAAAAAAACCACCGCTACCAGCGGTGGTTTGTTTG
CCGGATCAAGAGCTACCAACTCTTTTTCCGAAGGTAACTGGCTTCAGCAG
AGCGCAGATACCAAATACTGTCCTTCTAGTGTAGCCGTAGTTAGGCCACC
ACTTCAAGAACTCTGTAGCACCGCCTACATACCTCGCTCTGCTAATCCTG
TTACCAGTGGCTGCTGCCAGTGGCGATAAGTCGTGTCTTACCGGGTTGGA
CTCAAGACGATAGTTACCGGATAAGGCGCAGCGGTCGGGCTGAACGGGGG
GTTCGTGCACACAGCCCAGCTTGGAGCGAACGACCTACACCGAACTGAGA
TACCTACAGCGTGAGCTATGAGAAAGCGCCACGCTTCCCGAAGGGAGAAA
GGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTT
CGCCACCTCTGACTTGAGCGTCGATTTTTGTGATGCTCGTCAGGGGGCG
GAGCCTATGGAAAAACGCCAGCAACGCGGCCTTTTTACGGTTCCTGGCCT
TTTGCTGGCCTTTTGCTCACATGTTCTTTCCTGCGTTATCCCCTGATTCT
GTGGATAACCGTATTACCGCCTTTGAGTGAGCTGATACCGCTCGCCGCAG
CCGAACGACCGAGCGCAGCGAGTCAGTGAGCGAGGAAGCGGAAGAGCGCC
TGATGCGGTATTTTCTCCTTACGCATCTGTGCGGTATTTCACACCGCATA
TG
```

Functional in-frame peptide fragments such as those consisting of either 1) apoptin 1-121, 2) apoptin 33-121, 3) apoptin 82-121, 4) apoptin 97-121, 5) apoptin 106-121, 6) apoptin 111-121 or 7) apoptin 1-31 linked to 83-121 are further constructed by PCR and restriction endonuclease-based cloning methods and synthetic biology known to those skilled in the art as shown in FIG. 3D.

Example 10

Cytotoxicity of the cloned S. paratyphi cytolethal distending toxin wild type and reorganized operon with an inserted polylinker, and apoptin fusions. Cytotoxicity of Salmonella paratyphi A Cytolethal distending toxin toward MDA-MB-468 breast cancer cells is conducted using methods known to those skilled in the art and is measured by the MTT assay where absorbance at 570 nm indicates the relative number of live cells. (FIGS. 8A and 8B). By comparing no treatment control and a bacterial culture supernatant carrying an empty vector plasmid into a 100 µL tissue culture well control with a the reorganized polycistronic S. paratyphi A cytolethal distending operon containing a polylinker in cldtB C-terminus with dilutions of ½, ¼, ⅛, and ¹⁄₁₆ and the reorganized polycistronic S. paratyphi A cytolethal distending operon without a polylinker in cldtB C-terminus, the ability of the CLDT is demonstrated, and the ability to secrete CLDT from the reorganized operon lacking sty and ttsA is demonstrated, as well as the ability to accommodate a polylinker.

Example 11

C-terminal fusions with typhoid toxin cldtB and a modified apoptin wherein the phosphorylation site T108 and the two adjacent threonines 106 and 107 are mutated to alanines does not alter cytotoxicity. The mutations are made by methods known to those skilled in the art. Modification of the phosphorylation sites abrogates the activity of apoptin. The resulting cytotoxicity test shows that there was no change in cytotoxicity, therefore, the cldtB:apoptin fusion does not acquire cell killing ability from the apoptin.

Example 12

A chimeric YebF:SFTI. The chimeric sunflower trypsin inhibitor:YebF fusion is made by methods known to those skilled in the art. The complete sequence of a tetracycline-inducible YebF:SFTI the start codon begins at 724 and the stop codon ends at 1158 is given by:

```
                                               SEQ ID NO.: 017
ATATGGGGCGGCCGCCTAAGACCCACTTTCACATTTAAGTTGTTTTTCT
AATCCGCATATAATCAATTCAAGGCCGAATAAGAAGGCTGGCTCTGCACC
TTGGTGTTCAAATAATTCGATAGCTTGTCGTAATAATGCCGGCATACTAT
CAGTAGTAGGTGTTTCCCTTTCTTCTTTAGCGACTTGATGCTCTTGATCT
TCCAATACGCAACCTAAAGTAAAATGCCCCACAGCGCTGAGTGCATATAA
TGCATTCTCTAGTGAAAAACCTTGTTGGCATAAAAAGGCTAATTGATTTT
CGAGAGTTTCATACTGTTTTTCTGTAGGCCGTGTACCTAAATGTACTTTT
GCTCCATCGCGATGACTTAGTAAAGCACATCTAAAACTTTTAGCGTTATT
ACGTAAAAAATCTTGCCAGCTTTCCCCTTCTAAAGGGCAAAAGTGAGTAT
GGTGCCTATCTAACATCTCAATGGCTAAGGCGTCGAGCAAAGCCCGCTTA
TTTTTTACATGCCAATACAATGTAGGCTGCTCTACACCCAGTTTCTGGGC
GAGTTTACGGGTTTTTAAACCTTCGATTCCGACCTCATTAAGCAGCTCTA
ATGCGCTGTTAATCACTTTACTTTTATCTAATCTGGACATCATAAATTCC
TAATTTTTGTTGACACTCTATCATTGATAGAGTTATTTTACCACTCCCTA
TCAGTGATAGAGAAAAGTGAACCatggctaaaaaagagggggcgttttta
gggctgttgttggtttctgcctgcgcatcagttttcgctgccaataatga
aaccagcaagtcggtcactttcccaaagtgtgaagatctggatgctgccg
gaattgccgcgagcgtaaaacgtgattatcaacaaaatcgcgtggcgcgt
tgggcagatgatcaaaaaattgtcggtcaggccgatcccgtggcttgggt
cagtttgcaggacattcagggtaaagatgataaatggtcagtaccgctaa
ccgtgcgtggtaaaagtgccgatattcattaccaggtcagcgtggactgc
aaagcgggaatggcggaatatcagcggcgtCTCGAGGACGATGACGATAA
GGGTACCCTGAAAGGCCGCTGCACCAAAAGCATTCCGCCGATTTGCTTTC
CGGATTAGTCTAGAGTCGACCTGCAGGCATGCAAGCTTGGCTGTTTTGGC
GGATGAGAGAAGATTTTCAGCCTGATACAGATTAAATCAGAACGCAGAAG
CGGTCTGATAAAACAGAATTTGCCTGGCGGCAGTAGCGCGGTGGTCCCAC
CTGACCCCATGCCGAACTCAGAAGTGAAACGCCGTAGCGCCGATGGTAGT
GTGGGGTCTCCCCATGCGAGAGTAGGGAACTGCCAGGCATCAAATAAAAC
GAAAGGCTCAGTCGAAAGACTGGGCCTTTCGTTTTATCTGTTGTTTGTCG
GTGAACGCTCTCCTGAGTAGGACAAATCCGCGGGAGCGGATTTGAACGT
TGCGAAGCAACGGCCCGGAGGGTGGCGGGCAGGACGCCCGCCATAAACTG
CCAGGCATCAAATTAAGCAGAAGGCCATCCTGACGGATGGCCTTTTTGCG
TTTCTACAAACTCTTTTTGTTTATTTTTCTAAATACATTCAAATATGTAT
CCGCTCATGAGACAATAACCCTGATAAATGCTTCAATAATATTGAAAAAG
GAAGAGTATGAGTATTCAACATTTCCGTGTCGCCCTTATTCCCTTTTTTG
CGGCATTTTGCCTTCCTGTTTTTGCTCACCCAGAAACGCTGGTGAAAGTA
AAAGATGCTGAAGATCAGTTGGGTGCACGAGTGGGTTACATCGAACTGGA
TCTCAACAGCGGTAAGATCCTTGAGAGTTTTCGCCCCGAAGAACGTTTTC
CAATGATGAGCACTTTTAAAGTTCTGCTATGTGGCGCGGTATTATCCCGT
GTTGACGCCGGGCAAGAGCAACTCGGTCGCCGCATACACTATTCTCAGAA
TGACTTGGTTGAGTACTCACCAGTCACAGAAAAGCATCTTACGGATGGCA
TGACAGTAAGAGAATTATGCAGTGCTGCCATAACCATGAGTGATAACACT
GCGGCCAACTTACTTCTGACAACGATCGGAGGACCGAAGGAGCTAACCGC
TTTTTTGCACAACATGGGGGATCATGTAACTCGCCTTGATCGTTGGGAAC
CGGAGCTGAATGAAGCCATACCAAACGACGAGCGTGACACCACGATGCCT
ACAGCAATGGCAACAACGTTGCGCAAACTATTAACTGGCGAACTACTTAC
TCTAGCTTCCCGGCAACAATTAATAGACTGGATGGAGGCGGATAAAGTTG
CAGGACCACTTCTGCGCTCGGCCCTTCCGGCTGGCTGGTTTATTGCTGAT
AAATCTGGAGCCGGTGAGCGTGGGTCTCGCGGTATCATTGCAGCACTGGG
GCCAGATGGTAAGCCCTCCCGTATCGTAGTTATCTACACGACGGGGAGTC
AGGCAACTATGGATGAACGAAATAGACAGATCGCTGAGATAGGTGCCTCA
CTGATTAAGCATTGGTAACTGTCAGACCAAGTTTACTCATATATACTTTA
GATTGATTTAAAACTTCATTTTTAATTTAAAAGGATCTAGGTGAAGATCC
TTTTTGATAATCTCATGACCAAAATCCCTTAACGTGAGTTTTCGTTCCAC
TGAGCGTCAGACCCCGTAGAAAAGATCAAAGGATCTTCTTGAGATCCTTT
TTTTCTGCGCGTAATCTGCTGCTTGCAAACAAAAAAACCACCGCTACCAG
CGGTGGTTTGTTTGCCGGATCAAGAGCTACCAACTCTTTTTCCGAAGGTA
ACTGGCTTCAGCAGAGCGCAGATACCAAATACTGTCCTTCTAGTGTAGCC
GTAGTTAGGCCACCACTTCAAGAACTCTGTAGCACCGCCTACATACCTCG
CTCTGCTAATCCTGTTACCAGTGGCTGCTGCCAGTGGCGATAAGTCGTGT
CTTACCGGGTTGGACTCAAGACGATAGTTACCGGATAAGGCGCAGCGGTC
GGGCTGAACGGGGGGTTCGTGCACACAGCCCAGCTTGGAGCGAACGACCT
ACACCGAACTGAGATACCTACAGCGTGAGCTATGAGAAAGCGCCACGCTT
CCCGAAGGGAGAAAGGCGGACAGGTATCCGGTAAGCGGCAGGGTCGGAAC
AGGAGAGCGCACGAGGGAGCTTCCAGGGGGAAACGCCTGGTATCTTTATA
GTCCTGTCGGGTTTCGCCACCTCTGACTTGAGCGTCGATTTTTGTGATGC
```

Example 13

A chimeric OmpA:SFTI. The chimeric sunflower trypsin inhibitor:OmpA fusion is made by methods known to those skilled in the art. The complete sequence of a tetracycline inducible OmpA:SFTI fusion of which the coding sequence begins with an ATG start codon begins at 725 and the TAG stop codon ends at 1008 that can be inserted into an expression vector is given by:

```
                                                SEQ ID NO.: 018
CATATGGGGGCGGCCGCCTAAGACCCACTTTCACATTTAAGTTGTTTTTC

TAATCCGCATATAATCAATTCAAGGCCGAATAAGAAGGCTGGCTCTGCAC

CTTGGTGTTCAAATAATTCGATAGCTTGTCGTAATAATGCCGGCATACTA

TCAGTAGTAGGTGTTTCCCTTTCTTCTTTAGCGACTTGATGCTCTTGATC

TTCCAATACGCAACCTAAAGTAAAATGCCCCACAGCGCTGAGTGCATATA

ATGCATTCTCTAGTGAAAAACCTTGTTGGCATAAAAAGGCTAATTGATTT

TCGAGAGTTTCATACTGTTTTCTGTAGGCCGTGTACCTAAATGTACTTT

TGCTCCATCGCGATGACTTAGTAAAGCACATCTAAAACTTTTAGCGTTAT

TACGTAAAAAATCTTGCCAGCTTTCCCCTTCTAAAGGGCAAAAGTGAGTA

TGGTGCCTATCTAACATCTCAATGGCTAAGGCGTCGAGCAAAGCCCGCTT

ATTTTTTACATGCCAATACAATGTAGGCTGCTCTACACCCAGTTTCTGGG

CGAGTTTACGGGTTTTTAAACCTTCGATTCCGACCTCATTAAGCAGCTCT

AATGCGCTGTTAATCACTTTACTTTTATCTAATCTGGACATCATAAATTC

CTAATTTTTGTTGACACTCTATCATTGATAGAGTTATTTTACCACTCCCT

ATCAGTGATAGAGAAAAGTGAACCATGGCTAAAAAGACAGCTATCGCGAT

TGCAGTGGCACTGGCTGGTTTCGCTACCGTAGCGCAGGCCGCTCCGAAAG

ATGGCCGCTGCACCAAAAGCATTCCGCCGATTTGCTTTCCGGATTAGTCT

AGAGTCGACCTGCAGGCATGCAAGCTTGGCTGTTTTGGCGGATGAGAGAA

GATTTTCAGCCTGATACAGATTAAATCAGAACGCAGAAGCGGTCTGATAA

AACAGAATTTGCCTGGCGGCAGTAGCGCGGTGGTCCCACCTGACCCCATG

CCGAACTCAGAAGTGAAACGCCGTAGCGCCGATGGTAGTGTGGGGTCTCC

CCATGCGAGAGTAGGGAACTGCCAGGCATCAAATAAAACGAAAGGCTCAG

TCGAAAGACTGGGCCTTTCGTTTTATCTGTTGTTTGTCGGTGAACGCTCT

CCTGAGTAGGACAAATCCGCCGGGAGCGGATTTGAACGTTGCGAAGCAAC

GGCCCGGAGGGTGGCGGGCAGGACGCCCGCCATAAACTGCCAGGCATCAA

ATTAAGCAGAAGGCCATCCTGACGGATGGCCTTTTTGCGTTTCTACAAAC

TCTTTTTGTTTATTTTTCTAAATACATTCAAATATGTATCCGCTCATGAG

ACAATAACCCTGATAAATGCTTCAATAATATTGAAAAAGGAAGAGTATGA

GTATTCAACATTTCCGTGTCGCCCTTATTCCCTTTTTTGCGGCATTTTGC

CTTCCTGTTTTTGCTCACCCAGAAACGCTGGTGAAAGTAAAAGATGCTGA

AGATCAGTTGGGTGCACGAGTGGGTTACATCGAACTGGATCTCAACAGCG

GTAAGATCCTTGAGAGTTTTCGCCCCGAAGAACGTTTTCCAATGATGAGC

ACTTTTAAAGTTCTGCTATGTGGCGCGGTATTATCCCGTGTTGACGCCGG

GCAAGAGCAACTCGGTCGCCGCATACACTATTCTCAGAATGACTTGGTTG

AGTACTCACCAGTCACAGAAAAGCATCTTACGGATGGCATGACAGTAAGA

GAATTATGCAGTGCTGCCATAACCATGAGTGATAACACTGCGGCCAACTT

ACTTCTGACAACGATCGGAGGACCGAAGGAGCTAACCGCTTTTTTGCACA

ACATGGGGGATCATGTAACTCGCCTTGATCGTTGGGAACCGGAGCTGAAT

GAAGCCATACCAAACGACGAGCGTGACACCACGATGCCTACAGCAATGGC

AACAACGTTGCGCAAACTATTAACTGGCGAACTACTTACTCTAGCTTCCC

GGCAACAATTAATAGACTGGATGGAGGCGGATAAAGTTGCAGGACCACTT

CTGCGCTCGGCCCTTCCGGCTGGCTGGTTTATTGCTGATAAATCTGGAGC

CGGTGAGCGTGGGTCTCGCGGTATCATTGCAGCACTGGGGCCAGATGGTA

AGCCCTCCCGTATCGTAGTTATCTACACGACGGGGAGTCAGGCAACTATG

GATGAACGAAATAGACAGATCGCTGAGATAGGTGCCTCACTGATTAAGCA

TTGGTAACTGTCAGACCAAGTTTACTCATATATACTTTAGATTGATTTAA

AACTTCATTTTTAATTTAAAAGGATCTAGGTGAAGATCCTTTTTGATAAT

CTCATGACCAAAATCCCTTAACGTGAGTTTTCGTTCCACTGAGCGTCAGA

CCCCGTAGAAAAGATCAAAGGATCTTCTTGAGATCCTTTTTTTCTGCGCG

TAATCTGCTGCTTGCAAACAAAAAAACCACCGCTACCAGCGGTGGTTTGT

TTGCCGGATCAAGAGCTACCAACTCTTTTTCCGAAGGTAACTGGCTTCAG

CAGAGCGCAGATACCAAATACTGTCCTTCTAGTGTAGCCGTAGTTAGGCC

ACCACTTCAAGAACTCTGTAGCACCGCCTACATACCTCGCTCTGCTAATC

CTGTTACCAGTGGCTGCTGCCAGTGGCGATAAGTCGTGTCTTACCGGGTT

GGACTCAAGACGATAGTTACCGGATAAGGCGCAGCGGTCGGGCTGAACGG

GGGGTTCGTGCACACAGCCCAGCTTGGAGCGAACGACCTACACCGAACTG

AGATACCTACAGCGTGAGCTATGAGAAAGCGCCACGCTTCCCGAAGGGAG

AAAGGCGGACAGGTATCCGGTAAGCGGCAGGGTCGGAACAGGAGAGCGCA

CGAGGGAGCTTCCAGGGGGAAACGCCTGGTATCTTTATAGTCCTGTCGGG

TTTCGCCACCTCTGACTTGAGCGTCGATTTTTGTGATGCTCGTCAGGGGG

GCGGAGCCTATGGAAAAACGCCAGCAACGCGGCCTTTTTACGGTTCCTGG

CCTTTTGCTGGCCTTTTGCTCACATGTTCTTTCCTGCGTTATCCCCTGAT

TCTGTGGATAACCGTATTACCGCCTTTGAGTGAGCTGATACCGCTCGCCG

CAGCCGAACGACCGAGCGCAGCGAGTCAGTGAGCGAGGAAGCGGAAGAGC

GCCTGATGCGGTATTTTCTCCTTACGCATCTGTGCGGTATTTCACACCG
```

Example 14

A chimeric OmpA:SFTI RBS E3 Lysis. The chimeric sunflower trypsin inhibitor:OmpA fusion is made by methods known to those skilled in the art. The complete sequence of a tetracycline inducible OmpA:SFTI fusion of which the coding sequence begins with an ATG start codon that begins at 725 and the TAG stop codon ends at 1008 followed by a Shine Delgarno sequence (RBS) and coding sequence for the E3 Lysis sequence of which begins with an ATG start codon that begins at 865 and ends with a TAA stop codon at 1008 that can be inserted into an expression vector is given by:

SEQ ID NO.: 019

```
CATATGGGGCGGCCGCCTAAGACCCACTTTCACATTTAAGTTGTTTTTC
TAATCCGCATATAATCAATTCAAGGCCGAATAAGAAGGCTGGCTCTGCAC
CTTGGTGTTCAAATAATTCGATAGCTTGTCGTAATAATGCCGGCATACTA
TCAGTAGTAGGTGTTTCCCTTTCTTCTTTAGCGACTTGATGCTCTTGATC
TTCCAATACGCAACCTAAAGTAAAATGCCCCACAGCGCTGAGTGCATATA
ATGCATTCTCTAGTGAAAAACCTTGTTGGCATAAAAAGGCTAATTGATTT
TCGAGAGTTTCATACTGTTTTTCTGTAGGCCGTGTACCTAAATGTACTTT
TGCTCCATCGCGATGACTTAGTAAAGCACATCTAAAACTTTTAGCGTTAT
TACGTAAAAAATCTTGCCAGCTTTCCCCTTCTAAAGGGCAAAAGTGAGTA
TGGTGCCTATCTAACATCTCAATGGCTAAGGCGTCGAGCAAAGCCCGCTT
ATTTTTTACATGCCAATACAATGTAGGCTGCTCTACACCCAGTTTCTGGG
CGAGTTTACGGGTTTTTAAACCTTCGATTCCGACCTCATTAAGCAGCTCT
AATGCGCTGTTAATCACTTTACTTTTATCTAATCTGGACATCATAAATTC
CTAATTTTTGTTGACACTCTATCATTGATAGAGTTATTTTACCACTCCCT
ATCAGTGATAGAGAAAAGTGAACCATGGCTAAAAAGACAGCTATCGCGAT
TGCAGTGGCACTGGCTGGTTTCGCTACCGTAGCGCAGGCCGCTCCGAAAG
ATGGCCGCTGCACCAAAAGCATTCCGCCGATTTGCTTTCCGGATTAGTCT
AGAAAGGAGTCGTTATGAAAAAAATAACAGGGATTATTTTATTGCTTCTT
GCAGTCATTATTCTGTCTGCATGTCAGGCAAACTATATCCGGGATGTTCA
GGGCGGGACCGTATCTCCGTCATCAACAGCTGAAGTGACCGGATTAGCAA
CGCAGTAACTGCAGGCATGCAAGCTTGGCTGTTTTGGCGGATGAGAGAAG
ATTTTCAGCCTGATACAGATTAAATCAGAACGCAGAAGCGGTCTGATAAA
ACAGAATTTGCCTGGCGGCAGTAGCGCGGTGGTCCCACCTGACCCCATGC
CGAACTCAGAAGTGAAACGCCGTAGCGCCGATGGTAGTGTGGGGTCTCCC
CATGCGAGAGTAGGGAACTGCCAGGCATCAAATAAAACGAAAGGCTCAGT
CGAAAGACTGGGCCTTTCGTTTTATCTGTTGTTTGTCGGTGAACGCTCTC
CTGAGTAGGACAAATCCGCCGGGAGCGGATTTGAACGTTGCGAAGCAACG
GCCCGGAGGGTGGCGGGCAGGACGCCCGCCATAAACTGCCAGGCATCAAA
TTAAGCAGAAGGCCATCCTGACGGATGGCCTTTTTGCGTTTCTACAAACT
CTTTTTGTTTATTTTTCTAAATACATTCAAATATGTATCCGCTCATGAGA
CAATAACCCTGATAAATGCTTCAATAATATTGAAAAAGGAAGAGTATGAG
TATTCAACATTTCCGTGTCGCCCTTATTCCCTTTTTTGCGGCATTTTGCC
TTCCTGTTTTTGCTCACCCAGAAACGCTGGTGAAAGTAAAAGATGCTGAA
GATCAGTTGGGTGCACGAGTGGGTTACATCGAACTGGATCTCAACAGCGG
TAAGATCCTTGAGAGTTTTCGCCCCGAAGAACGTTTTCCAATGATGAGCA
CTTTTAAAGTTCTGCTATGTGGCGCGGTATTATCCCGTGTTGACGCCGGG
CAAGAGCAACTCGGTCGCCGCATACACTATTCTCAGAATGACTTGGTTGA
GTACTCACCAGTCACAGAAAAGCATCTTACGGATGGCATGACAGTAAGAG
AATTATGCAGTGCTGCCATAACCATGAGTGATAACACTGCGGCCAACTTA
CTTCTGACAACGATCGGAGGACCGAAGGAGCTAACCGCTTTTTTGCACAA
CATGGGGGATCATGTAACTCGCCTTGATCGTTGGGAACCGGAGCTGAATG
AAGCCATACCAAACGACGAGCGTGACACCACGATGCCTACAGCAATGGCA
ACAACGTTGCGCAAACTATTAACTGGCGAACTACTTACTCTAGCTTCCCG
GCAACAATTAATAGACTGGATGGAGGCGGATAAAGTTGCAGGACCACTTC
TGCGCTCGGCCCTTCCGGCTGGCTGGTTTATTGCTGATAAATCTGGAGCC
GGTGAGCGTGGGTCTCGCGGTATCATTGCAGCACTGGGGCCAGATGGTAA
GCCCTCCCGTATCGTAGTTATCTACACGACGGGGAGTCAGGCAACTATGG
ATGAACGAAATAGACAGATCGCTGAGATAGGTGCCTCACTGATTAAGCAT
TGGTAACTGTCAGACCAAGTTTACTCATATATACTTTAGATTGATTTAAA
ACTTCATTTTTAATTTAAAAGGATCTAGGTGAAGATCCTTTTTGATAATC
TCATGACCAAAATCCCTTAACGTGAGTTTTCGTTCCACTGAGCGTCAGAC
CCCGTAGAAAAGATCAAAGGATCTTCTTGAGATCCTTTTTTTCTGCGCGT
AATCTGCTGCTTGCAAACAAAAAAACCACCGCTACCAGCGGTGGTTTGTT
TGCCGGATCAAGAGCTACCAACTCTTTTTCCGAAGGTAACTGGCTTCAGC
AGAGCGCAGATACCAAATACTGTCCTTCTAGTGTAGCCGTAGTTAGGCCA
CCACTTCAAGAACTCTGTAGCACCGCCTACATACCTCGCTCTGCTAATCC
TGTTACCAGTGGCTGCTGCCAGTGGCGATAAGTCGTGTCTTACCGGGTTG
GACTCAAGACGATAGTTACCGGATAAGGCGCAGCGGTCGGGCTGAACGGG
GGGTTCGTGCACACAGCCCAGCTTGGAGCGAACGACCTACACCGAACTGA
GATACCTACAGCGTGAGCTATGAGAAAGCGCCACGCTTCCCGAAGGGAGA
AAGGCGGACAGGTATCCGGTAAGCGGCAGGGTCGGAACAGGAGAGCGCAC
GAGGGAGCTTCCAGGGGGAAACGCCTGGTATCTTTATAGTCCTGTCGGGT
TTCGCCACCTCTGACTTGAGCGTCGATTTTTGTGATGCTCGTCAGGGGGG
CGGAGCCTATGGAAAAACGCCAGCAACGCGGCCTTTTTACGGTTCCTGGC
CTTTTGCTGGCCTTTTGCTCACATGTTCTTTCCTGCGTTATCCCCTGATT
CTGTGGATAACCGTATTACCGCCTTTGAGTGAGCTGATACCGCTCGCCGC
AGCCGAACGACCGAGCGCAGCGAGTCAGTGAGCGAGGAAGCGGAAGAGCG
CCTGATGCGGTATTTTCTCCTTACGCATCTGTGCGGTATTTCACACCG
```

While the invention is shown by way of various examples and explanations, it should be understood that this specification and the drawings are intended to encompass the various combinations, sub-combinations, and permutations of the various features disclosed, and not limited by the particular combinations and sequences presented by way of example.

What is claimed is:

1. A pharmaceutically acceptable composition in a dosage form for administration to a human or an animal, the composition comprising a live *Salmonella* bacterium, efficacious for antineoplastic treatment of the human or the animal, comprising a genetic construct having a promoter operably linked to coding sequences for a functionally active modified chimeric *Pseudomonas* ToxA therapeutic molecule with antineoplastic activity comprising in operable linkage a secretion signal, a flexible linker comprising GGGGSGGGGSGGGGS, SEQ ID NO.: 008, a targeting domain, the *Pseudomonas* ToxA Domain Ib, containing at least 2 cysteines available for cysteine bonds, and the *Pseudomonas* ToxA Domain III, wherein the modified chimeric *Pseudomonas* ToxA therapeutic molecule with antineoplastic activity is secreted, dependent on the secretion signal, by the live host bacteria wherein the secreted ToxA is functionally active.

2. The pharmaceutically acceptable composition in a dosage form according to claim 1, comprising between about $10^5$ to $10^{12}$ live *Salmonella* bacterium each containing the genetic construct.

3. The pharmaceutically acceptable composition in a dosage form according to claim 1, wherein the *Pseudomonas* ToxA therapeutic molecule comprises an N-terminal fusion.

4. A method for treating neoplastic tumor cells within a living organism, comprising: administering to a human or an animal a pharmaceutically acceptable composition in a dosage form comprising live genetically engineered *Salmonella* bacterium having a genetic construct having a promoter which is operably linked to the coding sequence for a functionally active modified chimeric *Pseudomonas* ToxA therapeutic molecule with antineoplastic activity, having in operable linkage a secretion signal, a flexible linker comprising GGGGSGGGGSGGGGS, SEQ ID NO.: 008, a targeting domain, the *Pseudomonas* ToxA comprising the *Pseudomonas* ToxA Domain Ib containing at least 2 available cysteines for cysteine bonds, and the *Pseudomonas* ToxA Domain III, wherein the administered modified ToxA protein is expressed in the tumor cells and is secreted by said bacterium and wherein the secreted ToxA is functionally active.

5. The method according to claim 4, further comprising treating the human or animal with at least one systemic antibiotic to which the live genetically engineered *Salmonella* bacterium is sensitive.

* * * * *